United States Patent
Mason et al.

(10) Patent No.: US 12,332,179 B2
(45) Date of Patent: Jun. 17, 2025

(54) COLLIDING AND REACTING MOLECULES AND COLLOIDS ELECTROPHORETICALLY

(71) Applicants: Thomas G. Mason, Los Angeles, CA (US); Dimitri Athan Bikos, Manhattan, MT (US)

(72) Inventors: Thomas G. Mason, Los Angeles, CA (US); Dimitri Athan Bikos, Manhattan, MT (US)

(73) Assignee: Thomas G. Mason, Los Angeles, CA (US)

( * ) Notice: Subject to any disclaimer, the term of this patent is extended or adjusted under 35 U.S.C. 154(b) by 874 days.

(21) Appl. No.: 17/373,431

(22) Filed: Jul. 12, 2021

(65) Prior Publication Data
US 2022/0011236 A1 Jan. 13, 2022

Related U.S. Application Data

(60) Provisional application No. 63/050,466, filed on Jul. 10, 2020.

(51) Int. Cl.
*G01N 21/66* (2006.01)
*G01N 21/75* (2006.01)
(Continued)

(52) U.S. Cl.
CPC ............. *G01N 21/66* (2013.01); *G01N 21/75* (2013.01); *G01N 27/44756* (2013.01); *G01N 33/561* (2013.01)

(58) Field of Classification Search
CPC ...... G01N 21/66; G01N 21/75; G01N 27/447; G01N 27/44756; G01N 27/44773; G01N 27/453; G01N 33/561
See application file for complete search history.

(56) References Cited

U.S. PATENT DOCUMENTS 3,674,678 A * 7/1972 Post, Jr. ........... G01N 27/44756
204/616
5,055,415 A * 10/1991 Imai ..................... G01N 33/531
436/538
(Continued)

OTHER PUBLICATIONS

Reiner Westermeier, "Gel Electrophoresis," In: eLS. John Wiley & Sons, Ltd: Chichester. DOI: 10.1002/9780470015902.a0005335.pub2 (Year: 2013).*

(Continued)

*Primary Examiner* — Alexander S Noguerola
(74) *Attorney, Agent, or Firm* — Venable LLP; Henry J. Daley

(57) ABSTRACT

An electrophoretic spectroscopic imaging device for real-time spatially-resolved spectroscopic imaging of reagents and reaction-products resulting from electrophoretic collisions of reagents includes an electrophoresis component; a pair of electrodes; an illumination source; a spectroscopic-imaging device; and a computing device. An electrophoretic gel includes a matrix of porous solid material; and an electrolyte solution disposed within pores of the matrix. A method of electrophoretically colliding reagents includes providing a matrix that is a porous solid material having continuously interconnected pore regions that are filled with an electrolyte solution; loading a first reagent; loading a second reagent; and applying an electric field to the matrix loaded with the first reagent and the second reagent.

22 Claims, 48 Drawing Sheets
(47 of 48 Drawing Sheet(s) Filed in Color)

(51) Int. Cl.
  G01N 27/447 (2006.01)
  G01N 33/561 (2006.01)

(56) References Cited

U.S. PATENT DOCUMENTS

| | | | | |
|---|---|---|---|---|
| 5,217,591 | A * | 6/1993 | Gombocz | G01N 27/44704 204/616 |
| 5,958,202 | A * | 9/1999 | Regnier | G01N 33/78 435/6.12 |
| 7,799,194 | B2 * | 9/2010 | Makuska | C08F 251/00 204/469 |
| 2002/0146726 | A1 | 10/2002 | Matray | G01N 33/561 435/7.1 |
| 2003/0055231 | A1 * | 3/2003 | Ni | C07K 14/47 536/23.1 |
| 2012/0276655 | A1 * | 11/2012 | Cook | G01N 33/564 422/69 |

OTHER PUBLICATIONS

Holmes et al., "Estimation of polyacrylamide gel pore size from Ferguson plots of linear DNA fragments II. Comparison of gels with different crosslinker concentrations, added agarose and added linear polyacrylamide," Electrophoresis Dec. 1991, 612-619 (Year: 1991).*
Third Space Learning website definition of "prism shape" downloaded Jun. 25, 2024 from https://thirdspacelearning.com/us/math-resources/topic-guides/geometry/prism-shape/#:~:text=A%20prism%20shape%20is%20a,lateral%20sides%20connecting%20the%20bases. (Year: 2024).*
Casse et al., "Identification and characterization of large plasmids in Rhizobium meliloti using agarose gel electrophoresis", J. Gen. Microbiol. 113, 229-242 (1979).
Chrambach et al., "Polyacrylamide gel electrophoresis", Science 172, 440-451 (1971).
Lehrach et al., "RNA molecular weight determinations by gel electrophoresis under denaturing conditions, a critical reexamination", Biochemistry 16, 4743-4751 (1977).
Lesnaw et al., "Determination of molecular weights of plant viral protein subunits by polyacrylamide gel electrophoresis", Virology 42, 724-731 (1970).
Noble et al., "Comparison of lipoprotein analysis by agarose gel and paper electrophoresis with analytical ultracentrifugation", Lipids 4, 55-59 (1969).
Schwartz et al., "Separation of yeast chromosome-sized DNAs by pulsed field gradient gel electrophoresis", Cell 37, 67-75 (1984).
Sun et al., "A simple and efficient method for the separation and detection of small DNA fragments by electrophoresis in formamide containing agarose gels and southern blotting to DBM-paper", Nucleic Acids Res. 10, 5753-5763 (1982).
Lee et al., "Agarose gel electrophoresis for the separation of DNA fragments", J. Vis. Exp. 62, (2012) (5 pages).
Herring et al., "Rapid diagnosis of rotavirus infection by direct detection of viral nucleic acid in silver-stained polyacrylamide gels", J. Clin. Microbiol. 16, 473-477 (1982).
Kaufmann et al., "SDS-PAGE strongly overestimates the molecular masses of the neurofilament proteins", FEBS Lett. 170, 81-84 (1984).
Ikeuchi et al., "A new 4.8-kDa polypeptide intrinsic to the PS II reaction center, as revealed by modified SDS-PAGE with improved resolution of low-molecular-weight proteins", Plant Cell Physiol. 29, 1233-1239 (1988).
Carraro et al., "A sensitive SDS-PAGE method separating myosin heavy chain isoforms of rat skeletal muscles reveals the heterogeneous nature of the embryonic myosin", Biochem. Biophys. Res. Commun. 116, 793-802 (1983).
Tenover et al., "Interpreting chromosomal DNA restriction patterns produced by pulsed-field gel electrophoresis—Criteria for bacterial strain typing", J. Clin. Microbiol. 33, 2233-2239 (1995).

Gautom "Rapid pulsed-field gel electrophoresis protocol for typing of *Escherichia coli* O157:H7 and other gram-negative organisms in 1 day" J. Clin. Microbiol. 35, 2977-2980 (1997).
Bannerman et al., "Pulsed-field gel electrophoresis as a replacement for bacteriophage typing of *Staphylococcus aureus*", J. Clin. Microbiol. 33, 551-555 (1995).
Hyrien et al., "Plasmid replication in Xenopus eggs and egg extracts—a 2D gel electrophoretic analysis", Nucleic Acids Res. 20, 1463-1469 (1992).
Celis et al., "2D protein electrophoresis: Can it be perfected?", Curr. Opin. Biotechnol. 10, 16-21 (1999).
Farrell et al., "Analysis of phosphorylation of protein synthesis initiation factor eIF-2 by two-dimensional gel electrophoresis" Eur. J. Biochem. 89, 517-521 (1978).
Nakano et al., "Development of a highly sensitive three-dimensional gel electrophoresis method for characterization of monoclonal protein heterogeneity", Anal. Biochem. 438, 117-123 (2013).
Salimullah et al., "High-throughput three-dimensional gel electrophoresis for versatile utilities: A stacked slice-gel system for separation and reactions (4SR)", Genomics Proteomics Bioinformatics 4, 26-33 (2006).
Mauro et al., "Three-dimensional electrophoresis for quantitative profiling of complex proteomes", Methods Mol. Biol. 1295, 427-440 (2015).
Hellman et al., "Electrophoretic mobility shift assay (EMSA) for detecting protein-nucleic acid interactions", Nat. Protoc. 2, 1849-1861 (2007).
Jing et al., "A sensitive two-color electrophoretic mobility shift assay for detecting both nucleic acids and protein in gels", Proteomics 3, 1172-1180 (2003).
Laurell "Electroimmuno assay", Scand. J. Clin. Lab. Inv. 29, 21-37 (1972).
Georges "Mapping, fine mapping, and molecular dissection of quantitative trait loci in domestic animals", Annu. Rev. Genom. Hum. G. 8, 131-162 (2007).
White et al., "Inhibition of transcription factor-DNA complexes and gene expression by a microgonotropen", Proc. Natl. Acad. Sci. U.S.A. 98, 10590-10595 (2001).
Bellamy et al., "Differences between Ca2+ and Mg2+ in DNA binding and release by the SfiI restriction endonuclease: implications for DNA looping", Nucleic Acids Res. 37, 5443-5453 (2009).
Fried et al., "Equilibria and kinetics of lac repressor-operator interactions by polyacrylamide gel electrophoresis", Nucleic Acids Res. 9, 6505-6525 (1981).
Fried et al., "Factors that affect the stability of protein-DNA complexes during gel electrophoresis", Electrophoresis 18, 6-11 (1997).
Fried et al., "Kinetics and mechanism in the reaction of gene regulatory proteins with DNA", J. Mol. Biol. 172, 263-282 (1984).
Fried et al., "Molecular sequestration stabilizes CAP-DNA complexes during polyacrylamide gel electrophoresis", Nucleic Acids Res. 22, 5054-5059 (1994).
Goodrich et al., "Studying the affinity, kinetic stability, and specificity of RNA/protein interactions: SINE ncRNA/Pol II complexes as a model system", Methods Mol. Biol. 1206, 165-178 (2015).
Ruusala et al., "Sliding and intermolecular transfer of the lac repressor: kinetic perturbation of a reaction intermediate by a distant DNA sequence", Proc. Natl. Acad. Sci. U.S.A. 89, 4903-4907 (1992).
Sidorova et al., "Solution parameters modulating DNA binding specificity of the restriction endonuclease EcoRV", FEBS J. 278, 2713-2727 (2011).
Vossen et al., "Sequestration stabilizes lac repressor-DNA complexes during gel electrophoresis", Anal. Biochem. 245, 85-92 (1997).
Derbyshire et al., "Interaction between Chiorazol Sky Blue FF and Chrysophenine G in aqueous solution", J. Soc. Dyers Colour. 72, 268-277 (1956).
Morita et al., "Studies on mixture dyeing. III. Absorption spectra of direct dye mixtures in an aqueous solution", Bull. Chern. Soc. Jpn. 38, 2041-2044 (1965).

(56) References Cited

OTHER PUBLICATIONS

Quadrifoglio et al., "Interaction of methyl orange and other azo-dyes with polyelectrolytes and with colloidal electrolytes in dilute aqueous solution", J. Colloid Interface Sci. 35, 447-459 (1971).
Sheth "Studies in interaction between polyvinyl pyrrolidone and stilbene fluorescent compounds II. Interaction with mixture of compounds", J. Appl. Polym. Sci. 32, 4333-4342 (1986).
Kobayashi et al., "Absorption spectra of dyes. VII. Some steric effects and auxochrome-effects on complex formation", Bull. Chem. Soc. Jpn. 35, 935-939 (1962).
Inscoe et al., "Relation between the absorption spectra and the chemical constitution of Dyes: XXIX. Interaction of direct azo dyes in aqueous solution", J. Res. Nat. Bur. Stand. 60, 65-83 (1958).
Sabnis, R. W. Handbook of Biological Dyes and Stains: Synthesis and Industrial Applications (Hoboken, NJ, Wiley, 2010).
Gloria et al., "Synthetic Colorants. In: Nollet LML, Toldra F (eds)", Handbook of Food Analysis, 3rd ed. (Boca Raton, CRC Press, 2015), pp. 105-132.
Yeh "Polyacrylamide gel electrophoresis of water-soluble coal-tar dyes", J. Chromatogr. A 132, 566-568 (1977).
Bikos et al., "Influence of ionic constituents and electrical conductivity on the propagation of charged nanoscale objects in passivated gel electrophoresis", Electrophoresis 39, 394-405 (2018).
Hsieh et al., "A stopped-flow continuous-flow method for kinetic determinations", Anal. Chim. Acta 309, 277-282 (1995).
Parker et al., "Kinetics of complexation of V(V), U(VI), and Fe(III) with glutaroimide-dioxime: Studies by stopped-flow and conventional absorption spectroscopy", Dalton Trans. 46, 11084-11096 (2017).
Zhang et al., "Stopped-flow kinetic studies of the formation and disintegration of polyion complex micelles in aqueous solution", Phys. Chem. Chem. Phys. 16, 117-127 (2014).
Phillips et al., "Laser deceleration of an atomic beam", Phys. Rev. Lett. 48, 596-599 (1982).
King et al., "Molecular-beam investigation of adsorption kinetics on bulk metal targets—nitrogen on tungsten", Surf. Sci. 29, 454-482 (1972).
Barker et al., "Gas-surface interactions and dynamics: Thermal energy atomic and molecular beam studies", Surf. Sci. Rep. 4, 1-99 (1984).
Beijerinck et al., "Calibration of a time-of-flight machine for molecular beam studies", J. Phys. E Sci. Instrum. 7, 31-36 (1974).
Smoluchowski "Contribution à la théorie de l'endosmose électrique et de quelques phénomènes corrélatifs", Bull. Int. Acad. Sci. Cracovie. 3, 182-199 (1903).
Pernodet et al., "Pore size of agarose gels by atomic force microscopy", Electrophoresis 18, 55-58 (1997).
Harvey et al., "Colorimetric determination of magnesium with Eriochrome Black T", Anal. Chem. 25, 498-500 (1953).
Durham et al., "A survey of the available colorimetric indicators for Ca2+ and Mg2+ ions in biological experiments", Cell Calcium 4, 47-55 (1983).
Christian, G. D., Dasgupta, P. K. & Schug, K. Analytical Chemistry, 7th ed. (Hoboken, NJ, Wiley, 2014).
Gjems "Stoicheiometry of titration of calcium, magnesium and manganese at low concentration with EDTA, with the metal indicators murexide and Eriochrome Black T", Analyst 85, 738-744 (1960).
Eigen et al., "Kinetics of reactions in solution", Annu. Rev. Phys. Chem. 11, 307-334 (1960).
Moore et al., "Polyanions and their complexes. Part VII. Mechanism of methylene blue-polyanion interactions", J. Chem. Soc. A 1155-1159 (1970).
Zhu et al., "Passivated gel electrophoresis of charged nanospheres by light-scattering video tracking", J. Colloid Interface Sci. 428, 199-207 (2014).

Savenko "Solubility products of strontium carbonate and strontium sulfate in aqueous solution", Russ. J. Inorg. Chem. 46, 1102-1107 (2001).
Bray et al., "Reactions involving hydrogen peroxide, iodine and iodate ion. I. Introduction", J. Am. Chem. Soc. 53, 38-44 (1931).
Whittle et al., "Matrix isolation method for the experimental study of unstable species", J. Chem. Phys. 22, 1943-1943 (1954).
Riedel et al., "Polyfluoride anions, a matrix-isolation and quantum-chemical investigation", Inorg. Chem. 49, 7156-7164 (2010).
Polak et al., "Note on convergence of conjugate direction methods", Rev. Fr. Inform. Rech. O. 3, 35-43 (1969).
Ortega et al., "Prediction of hydrodynamic and other solution properties of rigid proteins from atomic- and residue-level models", Biophys. J. 101, 892-898 (2011).
Kiernan "Classification and naming of dyes, stains and fluorochromes", Biotech. Histochem. 76, 261-278 (2001).
Guthrie "Hydrolysis of esters of oxy acids: pKa values for strong acids; Brønsted relationship for attack of water at methyl; free energies of hydrolysis of esters of oxy acids; and a linear relationship between free energy of hydrolysis and pKa holding over a range of 20 pK units", Can. J. Chem. 56, 2342-2354 (1978).
Pérez-Urquiza et al., "Determination of the dissociation constants of sulfonated azo dyes by capillary zone electrophoresis and spectrophotometry methods", J. Chromatogr. A 917, 331-336 (2001).
Xu "Simultaneous determination of food pigments in mixtures by pH fixed titration", J. Shangqiu Teachers College 15, 79-83 (1999).
Flury et al., "Tracer characteristics of brilliant blue FCF", Soil Sci. Soc. Am. J. 59, 22-27 (1995).
Flury et al., "Brilliant blue FCF as a dye tracer for solute transport studies—A toxicological overview", J. Environ. Qual. 23, 1108-1112 (1994).
Patterson "A simplified method for finding the pKa of an acid-base indicator by spectrophotometry", J. Chem. Ed. 76, 395-398 (1999).
Diamond et al., "Integration of analytical measurements and wireless communications—Current issues and future strategies", Talanta 75, 606-612 (2008).
Lexa et al., "Brönsted basicity of vitamin B12s", J. Chem. Soc. Chem. Commun. 0, 872-874 (1975).
Arbeloa et al., "Molecular forms of rhodamine B", Chem. Phys. Lett. 79, 347-350 (1981).
Iogannsen "Some structural features of vital dyes", Bull. Exp. Bio. Med. 83, 591-595 (1977).
Goldacre et al., "370. The ionization of basic triphenylmethane dyes", J. Chem. Soc. 1724-1732 (1949).
Kim et al., "Heterogeneous oxidation of methylene blue with surface-modified iron-amended activated carbon", Am. J. Analyt. Chem. 4, 115-122 (2013).
Ouyang et al., "Electronic structure and bonding in vitamin B-12, cyanocobalamin", J. Mol. Struc.-Theochem. 622, 221-227 (2003).
Quast "Electroosmotic flow in agarose gels and value of agarose as stabilizing agent in gel electrofocusing", J. Chromatogr. 54, 405-412 (1971).
Maitra et al., "Hydrophobic pockets in a nonpolymeric aqueous gel: Observation of such a gelation process by color change", Angew. Chem. Int. Ed. 40, 2281-2283 (2001).
Ferreira et al., "pH effects on the ohmic properties of bromophenol blue-doped polypyrrole film", J. Brazil Chem. Soc. 21, 312-318 (2010).
Shokrollahi et al., "Determination of the acidity constants of neutral red and bromocresol green by solution scanometric method and comparison with spectrophotometric results", Beni-Suef Univ. J. Appl. Sci. 5, 13-20 (2016).
Bell "15N NMR investigation of azo-hydrazone acid-base equilibria of FD and C yellow No. 5 (tartrazine) and two analogs", Dyes Pigments 11, 93-99 (1989).
Shahir et al., "Comprehensive study of tartrazine/cationic surfactant interaction", J. Phys. Chem. B 115, 14435-14444 (2011).

\* cited by examiner

Tartrazine (TZ) anion
$C_{16}H_9N_4O_9S_2^{3-}$
(-3e; 9.4; 1.13; -3.52)

Allura Red AC (AR) anion
$C_{18}H_{14}N_2O_8S_2^{2-}$
(-2e; 11.4; 0.98; -2.49)

Brilliant Blue FCF (BB) zwitterion
$C_{37}H_{34}N_2O_9S_3^{2-}$
(-2e; 5.83, 6.58; 1.10; -2.15)

Bromophenol Blue (BPB) anion
$C_{19}H_8Br_4O_5S^{2-}$
(-2e; 3.95; 0.80, -2.60)

Bromocresol Green (BCG) anion
$C_{18}H_{14}N_2O_8S_2^{2-}$
(-2e; 4.85; 0.79, -2.57)

Cyanocobalamin (B12) zwitterion
$C_{63}H_{88}CoN_{14}O_{14}P$
(0e; 1, 2.9, 4.7; 1.1; ≈0)

Rhodamine B (RB) zwitterion
$C_{28}H_{30}N_2O_3$
(0e; 3.1; 0.93; ≈0)

Malachite Green (MAL) cation
$C_{23}H_{25}N_2^+$
(+1e; 2.2, 6.90; 0.91; 1.34)

Methylene Blue (MB) cation
$C_{16}H_{18}N_3S^+$
(+1e; 3.8; 0.88; 1.44)

Methyl Green (MG) cation
$C_{27}H_{35}N_3^{2+}$
(+2e; 0.2-1.8; 0.90; 2.54)

Tartrazine (TZ) anion
$C_{16}H_9N_4O_9S_2^{3-}$ 465.39 g mol$^{-1}$ (-3e; 9.4; 1.13; -3.52)

Allura Red AC (AR) anion
$C_{18}H_{14}N_2O_8S_2^{2-}$ 450.44 g mol$^{-1}$ (-2e; 11.4; 0.98; -2.49)

Bromocresol Green (BCG) anion
$C_{18}H_{14}N_2O_8S_2^{2-}$ 698.02 g mol⁻¹

(−2*e*; 4.85; 0.79, −2.57)

Cyanocobalamin (B12) zwitterion
$C_{63}H_{88}CoN_{14}O_{14}P$ 1,355.39 g mol⁻¹

(0*e*; 1, 2.9, 4.7; 1.1; ≈0)

Rhodamine B (RB) zwitterion
$C_{28}H_{30}N_2O_3$ 442.56 g mol$^{-1}$ (0$e$; 3.1; 0.93; ≈0)

Malachite Green (MAL) cation
$C_{23}H_{25}N_2^+$ 329.47 g mol$^{-1}$ (+1$e$; 2.2, 6.90; 0.91; 1.34)

Methylene Blue (MB) cation
$C_{16}H_{18}N_3S^+$ 284.40 g mol$^{-1}$ (+1$e$; 3.8; 0.88; 1.44)

Methyl Green (MG) cation
$C_{27}H_{35}N_3^{2+}$ 387.57 g mol$^{-1}$ (+2$e$; 0.2-1.8; 0.90; 2.54)

COLLIDING AND REACTING MOLECULES AND COLLOIDS ELECTROPHORETICALLY

CROSS-REFERENCE TO RELATED APPLICATIONS

The present patent application claims priority benefit to U.S. Provisional Patent Application No. 63/050,466, filed on Jul. 10, 2020, the entire content of which is incorporated herein by reference. All references cited anywhere in this specification, including the Background and Detailed Description sections, are incorporated by reference as if each had been individually incorporated.

BACKGROUND

1. Technical Field

The field of the currently claimed embodiments of this invention relates to electrophoresis, and more particularly to colliding and reacting molecules and colloids electrophoretically.

2. Discussion of Related Art

Gel electrophoresis (GE) is a powerful technique for characterizing and separating solvated ionic molecular or colloidal species based on their electrophoretic mobilities $\mu_e$. These species are loaded into wells in a nanoporous elastic gel immersed in an electrolyte buffer solution[1-6], and an electric field is then applied between two inert electrodes. For analyzing poly-anionic DNA and RNA, GE is an extremely important technology, providing high-resolution measurements of lengths of poly-nucleic acids[7-9]. Moreover, through sodium dodecyl sulfate-polyacrylamide gel electrophoresis (SDS-PAGE)[10-12], GE can be used with a wide range of proteins. Pulsed[13-15], 2 D[16-18], and 3D[19-21] forms have further broadened GE.

Electrophoretic mobility shift assays (EMSAs)[22-24] have extended GE significantly by probing interactions between macromolecular species, such as proteins and poly-nucleic acids, loaded into the same single well in a gel. After a pre-specified duration of interaction, an electric field is applied to induce separation. EMSAs are typically used to probe equilibrium biomolecular binding, since two bound species would typically propagate differently than either separately, and is therefore important in the field of genomic expression[25,26]. Beyond equilibrium binding, EMSAs have also been used to measure dissociation kinetics[27-35]. In addition, relative binding constants between competing ligands, orders of reactions, rate constants, and Arrhenius parameters can be measured using EMSAs[28]. In some cases, EMSAs have also assisted in deducing reaction mechanisms[30] and the presence of reactive intermediates[33]. Variability in binding efficiencies between certain mutant and wild-type enzymes have been discerned by EMSAs[27]. Certain short-lived transient protein-DNA complexes can persist for hours in a poly-acrylamide gel matrix during EMSAs[31]; this persistence likely arises from cage effects caused by the gel matrix that strongly reduce the rate of decomplexing of such long biomolecules[29]. Thus, EMSAs have been used to study kinetics not only in solution (e.g. within loading wells) but also within the porous gel matrix. EMSAs have also been performed at different pH and ionic strength[34]. While EMSAs have provided useful insights into biomolecular binding, loading reactant species into the same well limits the use of the protocol inherent to EMSAs for other types of reactions. Correspondingly, a 'gel dead time' limits the time resolution of kinetics since after activating the electric field it is typically necessary to wait for any complexes that might have been formed to leave the well and enter the gel before such binding interactions can be monitored[28]. Moreover, reaction kinetics could potentially be explored and visualized using a different GE approach that overcomes certain limitations of EMSAs.

Consequently, there remains a need for improved methods and systems for reacting molecules and colloids electrophoretically.

SUMMARY

A method of electrophoretically colliding reagents according to an embodiment of the current invention includes providing a matrix that is a porous solid material having continuously interconnected pore regions that are filled with an electrolyte solution, the matrix and the electrolyte being suitable for performing electrophoresis; loading a first reagent in a first reagent-loading-region centered at a first spatial location in the matrix; loading a second reagent in a second reagent-loading-region centered at a second spatial location that is displaced from the first spatial location by a first displacement-distance in the matrix; and applying an electric field to the matrix loaded with the first reagent and the second reagent. The applying the electric field causes electrophoretic propagation in the electrolyte solution through the continuously interconnected pore regions of at least one of a portion of the first reagent and a portion of the second reagent. The electric field is applied for a first period of time sufficiently long that at least a portion of the first reagent collides with at least a portion of the second reagent to yield a first collision in a first collision-region centered at a first collision-location within the matrix as a consequence of the electrophoretic propagation. A first electric field line of the electric field passes through the first reagent-loading-region and the second reagent-loading-region. The first displacement-distance is sufficiently large that the first reagent-loading-region is separate from the second reagent-loading-region, and a first electrophoretic mobility of the at least a portion of the first reagent in the matrix of the porous solid material filled with the electrolyte solution is different from a second electrophoretic mobility of the at least a portion of the second reagent in the matrix of the porous solid material filled with the electrolyte solution.

An electrophoretic spectroscopic imaging device for real-time spatially-resolved spectroscopic imaging of reagents and reaction-products resulting from electrophoretic collisions of reagents according to an embodiment of the current invention includes an electrophoresis component that includes an electrophoretic chamber suitable to receive a matrix of a porous solid material filled with an electrolyte solution in which a first reagent and a second reagent are loaded in localized regions during operation that are spatially separate; a pair of electrodes arranged to be proximate opposing ends of the matrix such that the matrix is arranged with at least a portion between the pair of electrodes and the pair of electrodes are structured to be electrically connected to a power supply such that at least a portion of the first and second reagents electrophoretically propagate as an ionic current that flows between the pair of electrodes and to collide as a consequence of applying an electric field between the pair of electrodes; an illumination source arranged to illuminate the matrix loaded with the first and second reagents with electromagnetic radiation such that interaction of the electromagnetic radiation with at least a portion of the first and second reagents yields at least one of absorbed, transmitted, scattered, fluoresced, phosphoresced, and emitted light as a function of spatial position in said matrix; a spectroscopic-imaging device configured to obtain at least one of image data and spectroscopic data from the at least one of absorbed, transmitted, scattered, fluoresced, phosphoresced, and emitted light at imaging times prior to, during, and subsequent to the electrophoretic collision; and a computing device configured to receive and process the at least one of image data and spectroscopic data to provide information concerning at least one of a spatial location of the electrophoretic collision of the at least a portion of the first and second reagents, a change in concentration of at least a portion of the first and second reagents, a detection of the existence of a reaction-product resulting from the electrophoretic collision, a measurement of the concentration of a reaction-product resulting from the electrophoretic collision, a yield of a reaction-product resulting from the electrophoretic collision, an electrophoretic mobility of a reaction-product resulting from the electrophoretic collision, a rate constant associated with a reaction-product resulting from the electrophoretic collision, and a temporal stability of a reaction-product resulting from the electrophoretic collision. The applying an electric field comprises applying a voltage across a first electrode immersed in the electrolyte solution and a second electrode immersed in the electrolyte solution thereby generating an ionic current that flows between the first electrode and the second electrode. The computing device is further configured to measure a space-time plot from the at least one of image data and spectroscopic data.

An electrophoretic gel according to an embodiment of the current invention includes a matrix of porous solid material and an electrolyte solution disposed within pores of the matrix. The matrix defines a plurality of rectangular prismatic wells that are devoid of the porous solid material to be suitable for producing electrophoretic propagation and collision of reagents when loaded in the rectangular prismatic wells that at least one of counter-propagate, co-propagate, and uni-propagate during use. Each of the plurality of rectangular prismatic wells has a same orientation. A first lane of the matrix defines at least a first rectangular prismatic well, a second rectangular prismatic well, and a third rectangular prismatic well out of the plurality of rectangular prismatic wells, and a second lane of the matrix defines at least a fourth rectangular prismatic well, a fifth rectangular prismatic well, and a sixth rectangular prismatic well out of the plurality of rectangular prismatic wells. A first separation distance between the first rectangular prismatic well and the second rectangular prismatic well in the first lane is equal to a second separation distance between said fourth rectangular prismatic well and the fifth rectangular prismatic well in the second lane, and a third separation distance between the second rectangular prismatic well and the third rectangular prismatic well in the first lane is equal to a fourth separation distance between the fifth rectangular prismatic well and the sixth rectangular prismatic well in the second lane. A minimum spatial dimension of the first and second rectangular prismatic wells lies along a line between a first center of the first rectangular prismatic well and a second center of the second rectangular prismatic well in the first lane.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Embodiments of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

Values in parentheses at the upper left represent nearest integer charge q (e); pKa value(s) or range(s) from literature sources (see Supplementary Methods); translational hydrodynamic radius a (in nm); and measured electrophoretic mobility $\mu_{e,meas}$ (in $10^{-8}$ m$^2$ V$^{-1}$ s$^{-1}$). Charges are approximate and have been rounded to the nearest integer (see Supplementary Methods). Estimates of equivalent hydrodynamic sphere radii are made using WinHydroPro and HyperChem (see the Methods section).

Figure 8A:
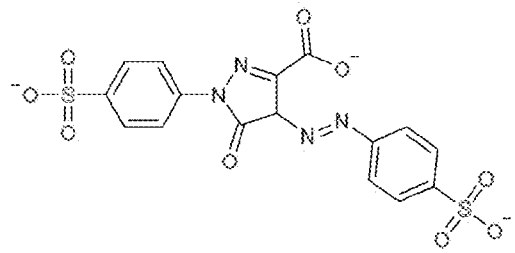
FIG. 8A shows a structural diagram and properties of organic dye Tartrazine (TZ) anion 465.39 g $mol^{-1}$ at pH=9.
Figure 8B:
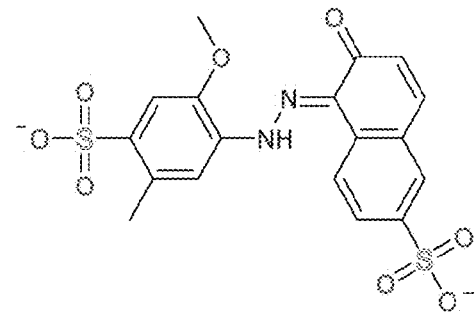

FIG. 8B shows a structural diagram and properties of organic dye Allura Red (AR) anion, 450.44 g mol$^{-1}$ at pH=9. Organization of properties is the same as in FIG. 8A.

Figure 8C:
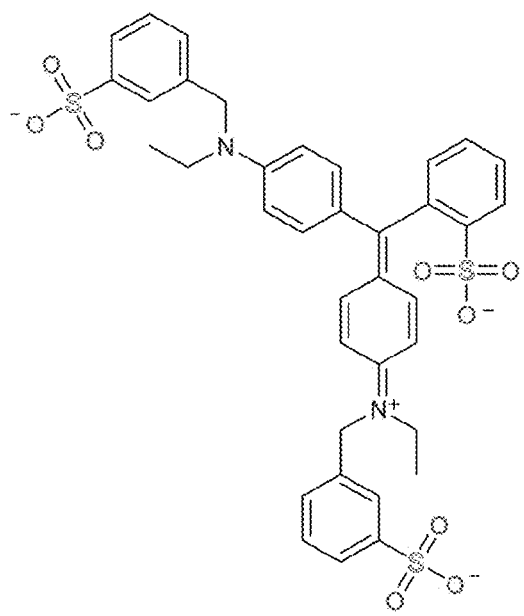

FIG. 8C shows a structural diagram and properties of organic dye Brilliant Blue FCF (BB) zwitterion, 746.87 g mol$^{-1}$ at pH=9. Organization of properties is the same as in FIG. 8A.

Figure 8D:
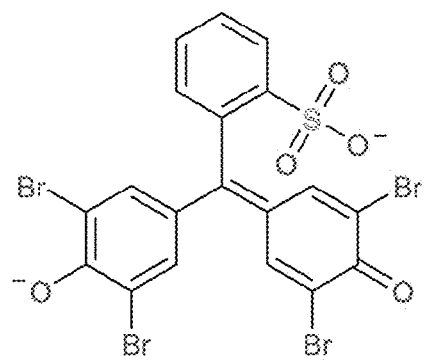

FIG. 8D shows a structural diagram and properties of organic dye Bromophenol Blue (BPB) anion, 667.95 g mol$^{-1}$ at pH=9. Organization of properties is the same as in FIG. 8A.

Figure 8E:
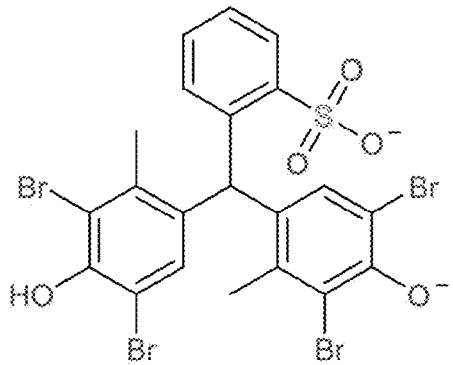

FIG. 8E shows a structural diagram and properties of organic dye Bromocresol Green (BCG) anion, 698.02 g mol$^{-1}$ at pH=9.

Figure 8F:
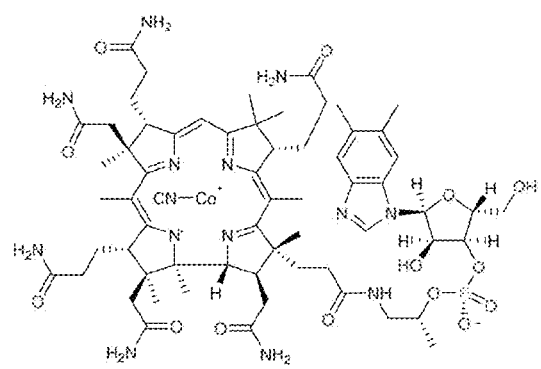

FIG. 8F shows a structural diagram and properties of organic dye Cyanocobalamin FCF (B12) zwitterion, 1,355.39 g mol$^{-1}$ at pH=9.

Figure 8G:
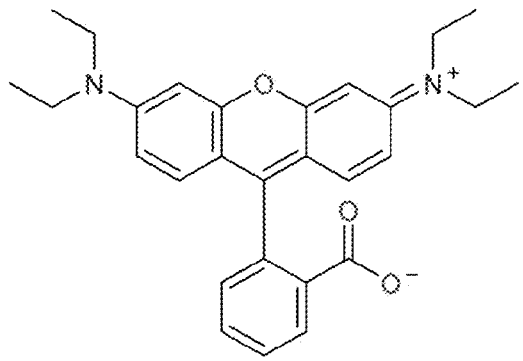

FIG. 8G shows a structural diagram and properties of organic dye Rhodamine B (RB) zwitterion, 442.56 g mol$^{-1}$ at pH=9.

Figure 8H:
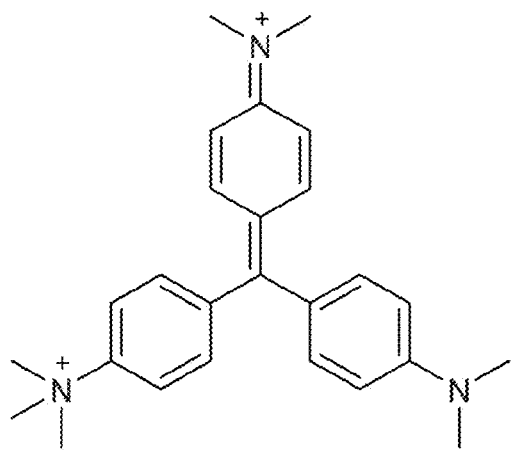

FIG. 8H shows a structural diagram and properties of organic dye Malachite Green (MAL) cation, 329.47 g mol$^{-1}$ at pH=9.

Figure 8I:
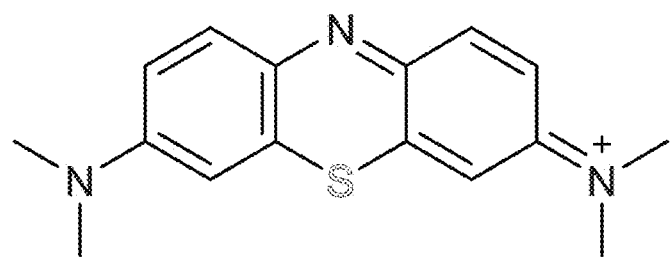

FIG. 8I shows a structural diagram and properties of organic dye Methylene Blue (MB) cation, 284.40 g mol$^{-1}$ at pH=9.

Figure 8J:
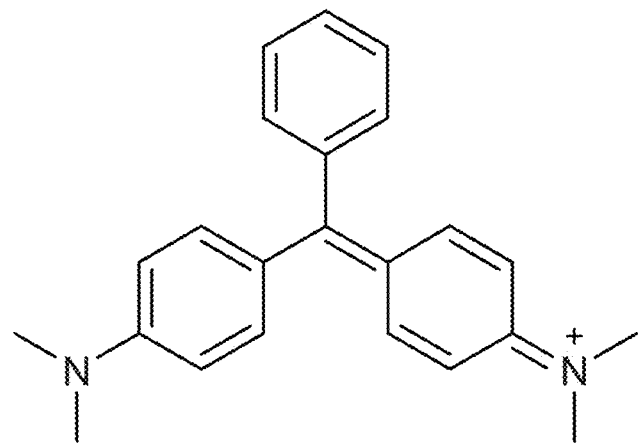

FIG. 8J shows a structural diagram and properties of organic dye Methyl Green (MG) cation, 387.57 g mol$^{-1}$ at pH=9.

Figure 9A:
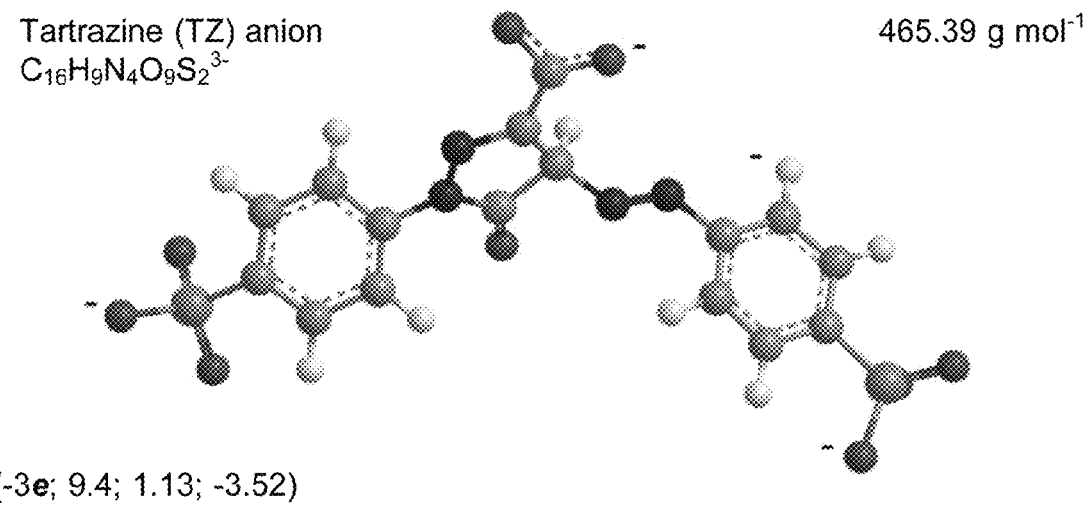

FIG. 9A shows a three-dimensional molecular model of an energy-optimized solvated configuration of the Tartrazine (TZ) anion at pH=9. The molar mass of TZ is in the upper right; values for TZ in the lower left in parentheses represent: charge q (units of e); pK$_a$; translational hydrodynamic radius a (units of nm); and electrophoretic mobility $\mu_e$ (units of $10^{-8}$ m$^2$ V$^{-1}$ s$^{-1}$). Modeling is performed using HyperChem. Estimates of equivalent hydrodynamic sphere radii are made using WinHydroPro and HyperChem (see the Methods section).

Figure 9B:
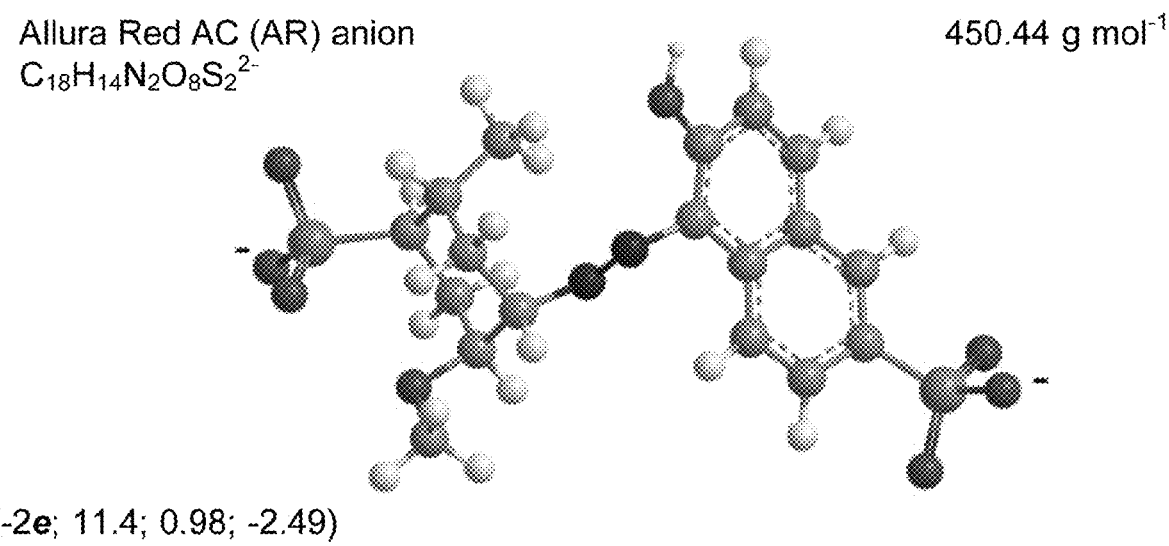

FIG. 9B shows a three-dimensional molecular model of an energy-optimized solvated configuration of the Allura Red AC (AR) anion at pH=9. Organization of properties is the same as in FIG. 9A.

Figure 9C:
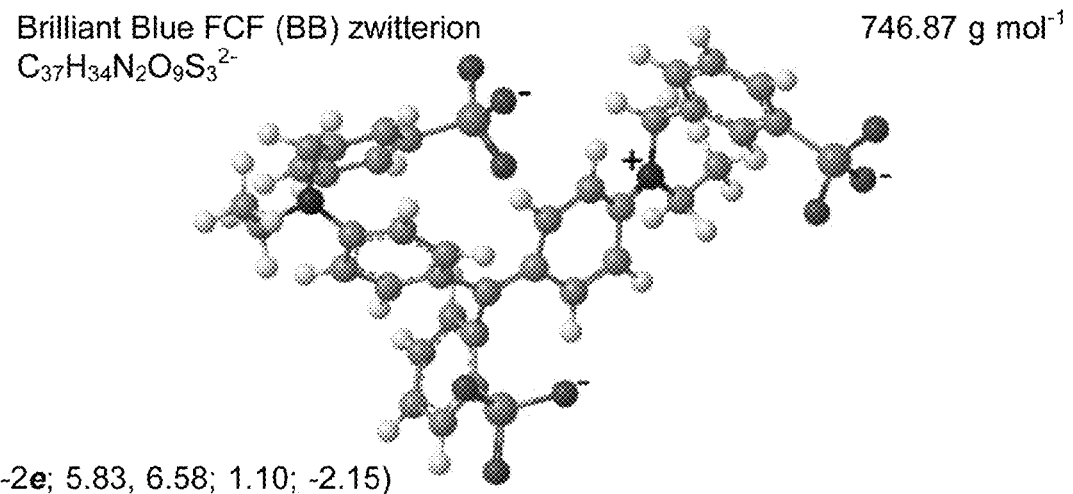

FIG. 9C shows a three-dimensional molecular model of an energy-optimized solvated configuration of the Brilliant Blue FCF (BB) zwitterion at pH=9. Organization of properties is the same as in FIG. 9A. Two values of pK$_a$ are listed.

Figure 9D:
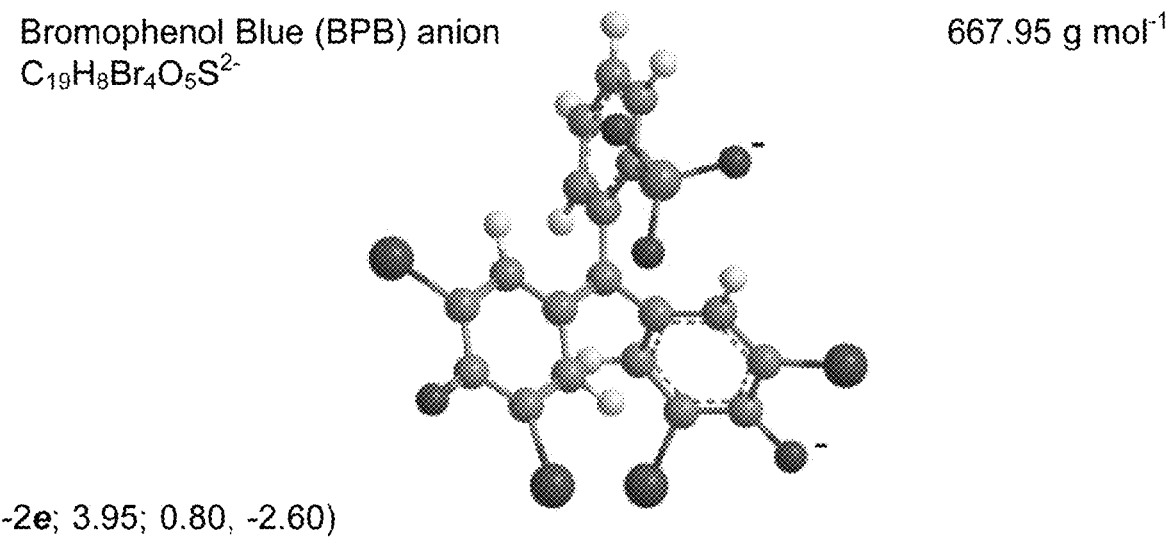

FIG. 9D shows a three-dimensional molecular model of an energy-optimized solvated configuration of the Bromophenol Blue (BPB) anion at pH=9. Organization of properties is the same as in FIG. 9A.

Figure 9E:
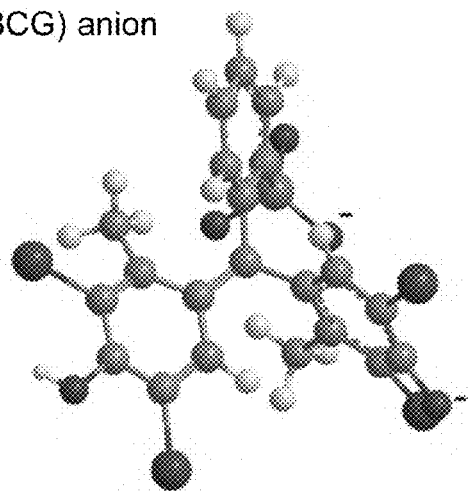

FIG. 9E shows a three-dimensional molecular model of an energy-optimized solvated configuration of the Bromocresol Green (BCG) anion at pH=9.

Figure 9F:
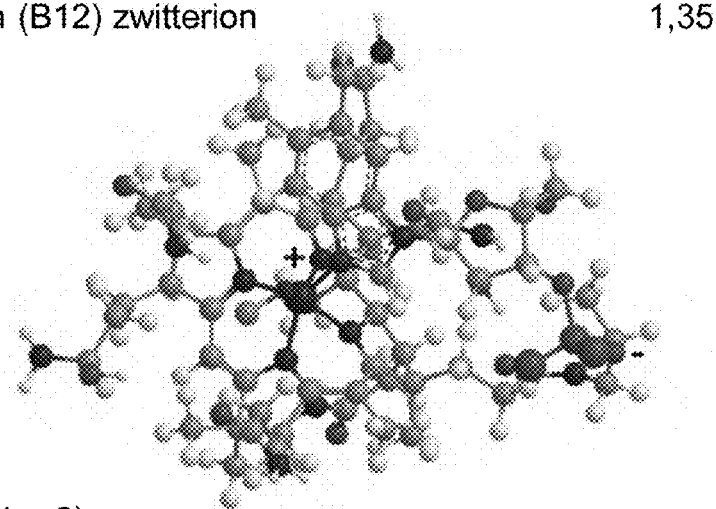

FIG. 9F shows a three-dimensional molecular model of an energy-optimized solvated configuration of the Cyanocobalamin (B12) zwitterion at pH=9. Two values of pK$_a$ are listed.

Figure 9G:
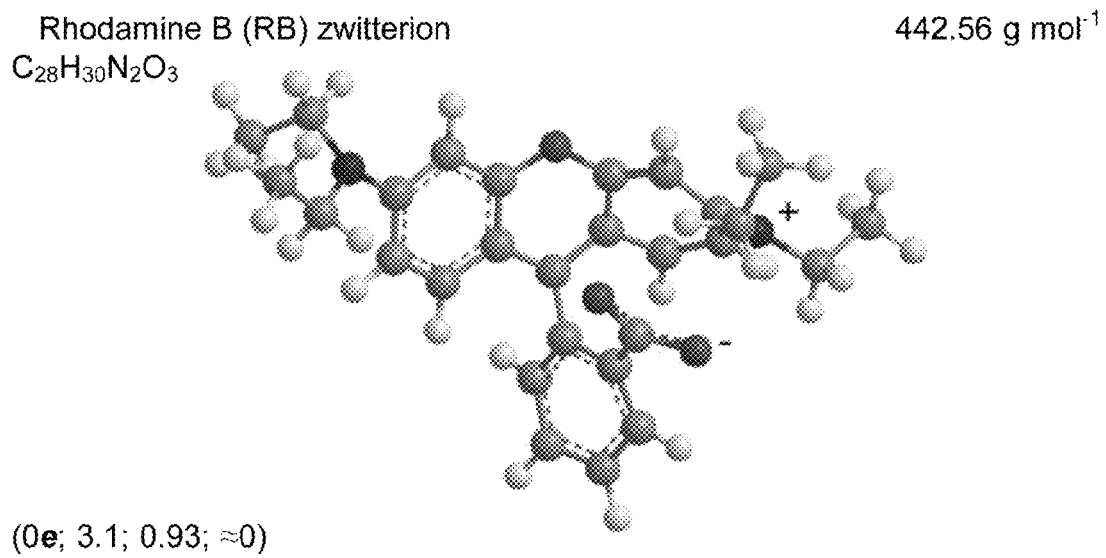

FIG. 9G shows a three-dimensional molecular model of an energy-optimized solvated configuration of the Rhodamine B (RB) zwitterion at pH=9.

Figure 9H:
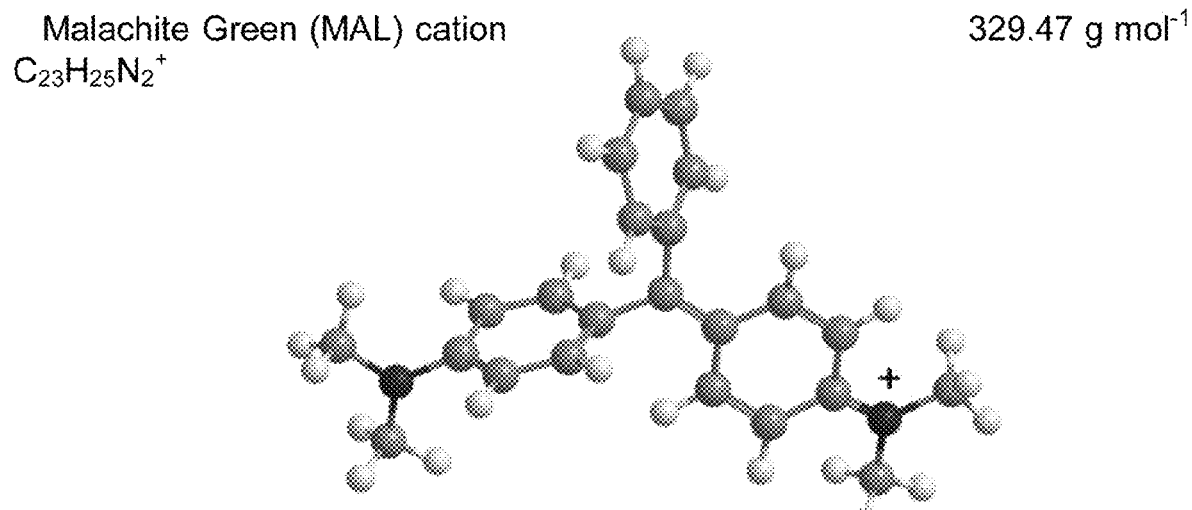

FIG. 9H shows a three-dimensional molecular model of an energy-optimized solvated configuration of the Malachite Green (MAL) cation at pH=9. Two values of pK$_a$ are listed.

Figure 9I:
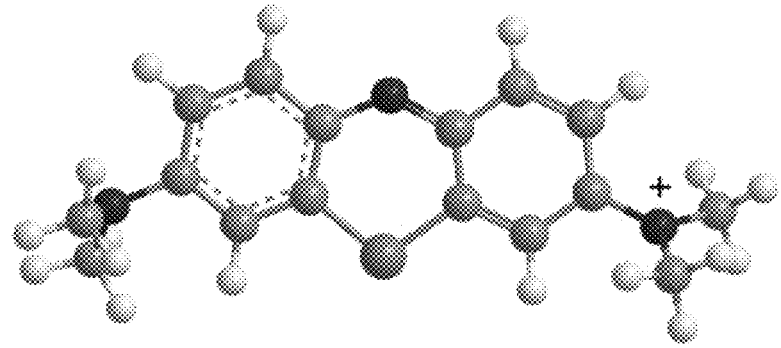

FIG. 9I shows a three-dimensional molecular model of an energy-optimized solvated configuration of the Methylene Blue (MB) cation at pH=9.

Figure 9J:
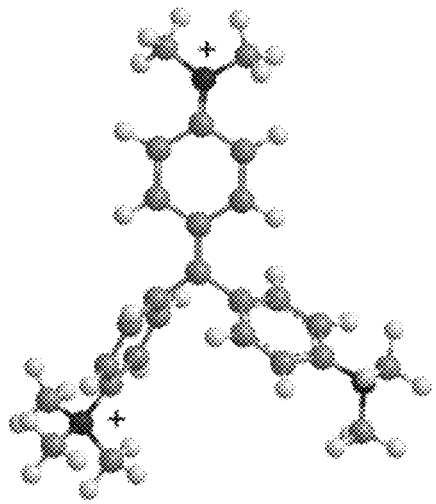

FIG. 9J shows a three-dimensional molecular model of an energy-optimized solvated configuration of the Methyl Green (MG) cation at pH=9. A range of pK$_a$ values is listed based on variations in literature values.

DETAILED DESCRIPTION

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

Electrophoretic mobility shift assays are widely used in gel electrophoresis to study binding interactions between different molecular species loaded into the same well. However, shift assays can access only a subset of reaction possibilities that could be otherwise seen if separate bands of these species might instead be collisionally reacted. Here, we adapt gel electrophoresis by fabricating two or more wells in the same lane, loading each well with different reagent species, and applying an electric field, thereby producing collisional reactions between propagating pulse-like bands of these species, which we image optically. For certain pairs of anionic and cationic dyes, propagating bands pass through each other unperturbed; yet, for other pairs, we observe complexing and precipitation reactions, indicating strong attractive interactions. We generalize this band-collision gel electrophoresis (BCGE) approach to other reaction types, including acid-base, ligand exchange, and redox, as well as to colloidal species in passivated large-pore gels.

Dye molecules can offer many advantages for initially demonstrating such a different GE approach, primarily because many dyes are charged, are typically much smaller than the characteristic pore sizes of gels, and can be readily seen as a consequence of optical absorption. Certain pairs of different dye molecules are known to attract and to form complexes or even precipitates in mixtures of bulk aqueous solutions, as observed decades ago using spectrophotometry[36,37]. The degree of attraction between two different dye molecules can involve electrostatic[38], hydrophobic[39], and pi-stacking interactions[38]; steric effects[40] and internal flexibility of the molecules can also be important. Moreover, short-range screened electrostatic attractions between acidic (anionic) dyes and basic (cationic) dyes[41] can enhance complex formation and precipitation, leading to non-additivity in optical absorption spectra of many anionic-cationic dye mixtures. Thus, dye molecules represent an important subset of potential reagents for readily demonstrating any new reactive GE method that goes beyond EMSAs.

Here, we provide a new GE to control and study the evolution of collisional reactions between two or more reagent species in solution that have different $\mu_e$. We design and fabricate two or more wells in the same lane of the gel, load each of these wells with individual reagent species, and then apply an electric field. To facilitate optical visualization, we first use anionic and cationic organic dye molecules[42] as reagent species, some of which have been previously studied individually in agarose[43] and polyacrylamide[44] gels. We record high resolution time-lapse videos of collisions between pulse-like bands of these species (see FIGS. 1A-1E and Methods), thereby revealing both attractive interactions and also irreversible chemical reactions. We extend this approach, which we call band-collision gel electrophoresis (BCGE), to include invisible (i.e. optically non-absorbing or only very weakly absorbing) molecules as well as colloidal species that scatter visible light, such as polymer nanospheres[45]. We show that a wide range of complex spatio-temporal patterns form and evolve when bands of different species collide. Moreover, we show that BCGE can be used to study not only associative intermolecular interactions, such as complexing and precipitation, but also acid-base, redox, and ligand-exchange reactions. Thus, collisional reactions probed using BCGE go well beyond prior investigations reporting propagation of bands of dye molecules without contact in separate lanes. In addition, using BCGE, sequences of reactions can be effectively programmed by appropriately choosing the location of the wells in the same lane and the types of species that are loaded into each of these wells. Thus, BCGE can provide the electrophoretic equivalent of microfluidic manipulation[46-48] of pulses of solvated and typically charged reagent species which is reminiscent of pulses of atomic and molecular ions that can be reacted through collisions in vacuo[49-52].

Figure 1A:
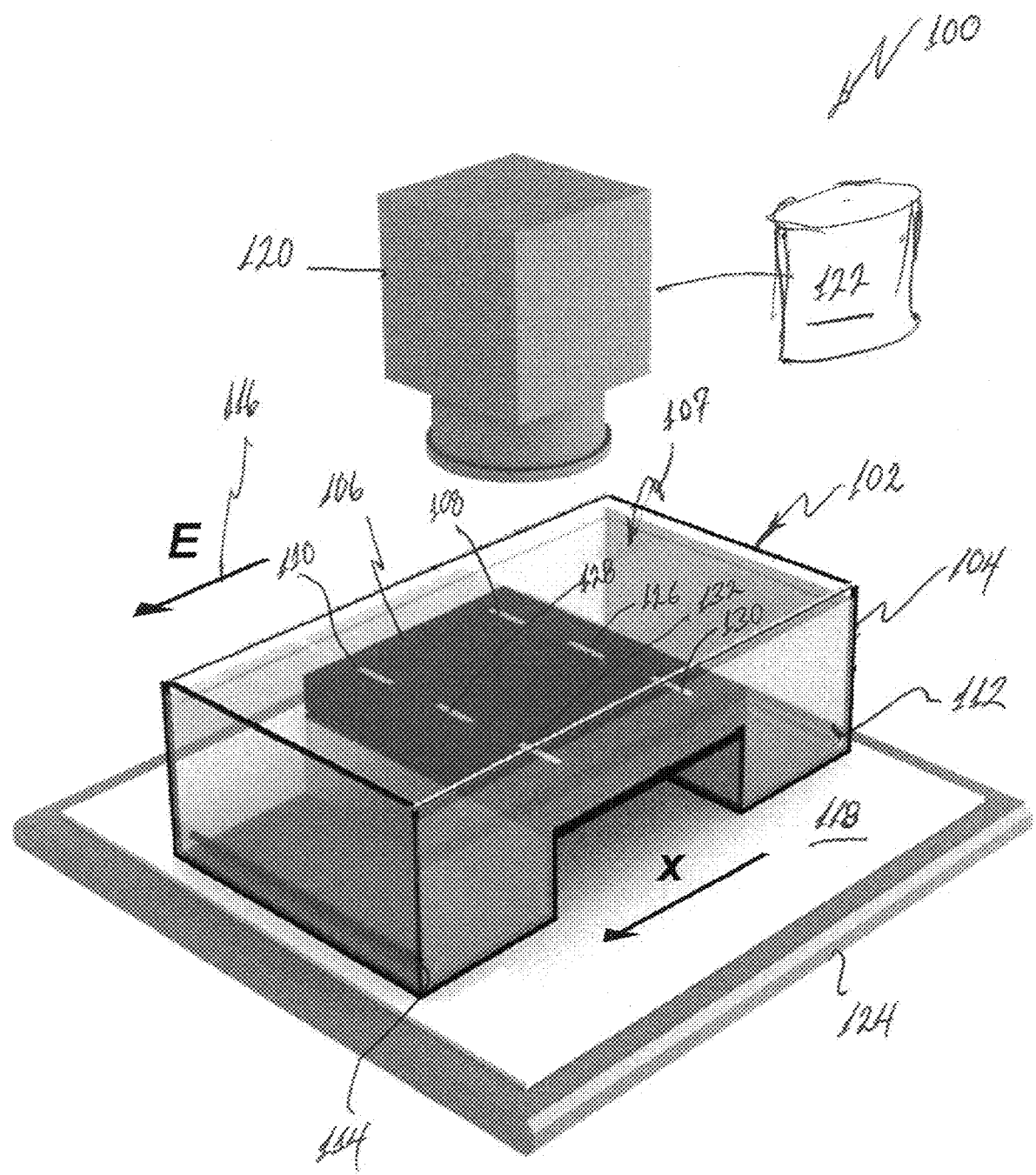
FIG. 1A is a schematic illustration of an apparatus for visualizing collisions and reactions between two different optically absorbing reagent species using band-collision gel electrophoresis (BCGE) according to an embodiment of the current invention. A gel, having two wells per lane, is cast and then transferred into a transparent horizontal gel electrophoresis chamber filled with a buffer solution at a desired pH. Pt-wires near the ends of the chamber are connected to a power supply (not shown). Wells are initially loaded with two different reagent species, and the power supply, which generates an electric field E that lies along the x-direction, is turned on at time t=0. A light box underneath the chamber provides uniform transmission illumination of white visible light, and time-lapse images are captured by an overhead mounted camera with a lens selected to minimize spatial distortion.
Figure 1B:
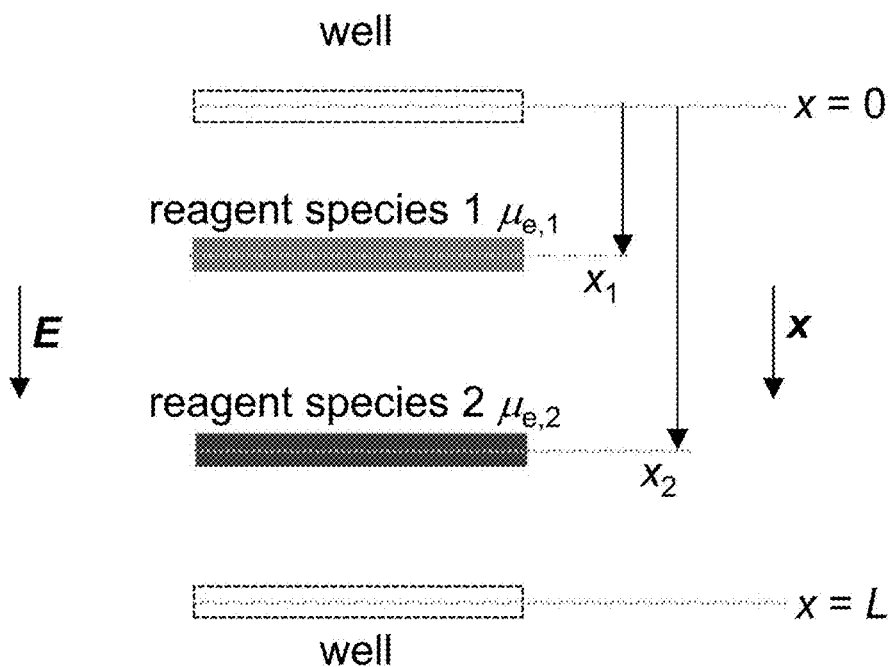
FIG. 1B shows an overhead view depicting the center locations $x_1(t)$ and x2(t) of propagating bands of reagent species 1 and 2, respectively, in a single lane at time t; both $x_1$ and x2 are referenced relative to the well centered at x=0. Reagent species 1 and 2 were initially loaded into the wells centered at x=0 and x=L, respectively. In this example, the electrophoretic mobilities of reagent species 1 and 2 have $\mu_{e,1}>0$ and $\mu_{e,2}<0$, respectively.

Accordingly, FIG. 1A is a schematic illustration of an electrophoretic spectroscopic imaging device 100 for real-time spatially-resolved spectroscopic imaging of reagents and reaction-products resulting from electrophoretic collisions of reagents. The device 100 includes an electrophoresis component 102 that includes an electrophoretic chamber 104 suitable to receive a matrix 106 of a porous solid material filled with an electrolyte solution 107 in which a first reagent and a second reagent are loaded in localized regions such as 108 and 110 during operation that are spatially separate. The device 100 also includes a pair of electrodes 112, 114 arranged to be proximate opposing ends of said matrix 106 such that said matrix 106 is arranged with at least a portion between said pair of electrodes 112, 114 and said pair of electrodes 112, 114 being structured to be electrically connected to a power supply (not shown) such that at least a portion of said first and second reagents electrophoretically propagate as an ionic current that flows between said pair of electrodes 112, 114 and to collide as a consequence of applying an electric field 116 between said pair of electrodes 112, 114. In the embodiment of FIG. 1A, localized regions 108, 110 are electrophoretic wells that are along a common lane. A lane is a path along reagents travel due to the applied electric field 116. FIG. 1A shows an example of a device 100 that has three lanes with two electrophoretic wells along each lane. Other embodiments can include more than two electrophoretic wells along a lane, and/or more or less than three lanes.

The device 100 also includes an illumination source 118 arranged to illuminate said matrix 106 loaded with said first and second reagents with electromagnetic radiation such that interaction of said electromagnetic radiation with at least a portion of said first and second reagents yields at least one of absorbed, transmitted, scattered, fluoresced, phosphoresced, and emitted light as a function of spatial position in said matrix. The term "light" is intended to have a broad meaning which can include light in the visible region of the electromagnetic spectrum as well as light in non-visible regions of the electromagnetic spectrum. For example, in addition to including visible light, the term "light" can include infrared light and ultraviolet light, for example.

The device 100 also includes a spectroscopic-imaging device 120 configured to obtain at least one of image data and spectroscopic data from said at least one of absorbed, transmitted, scattered, fluoresced, phosphoresced, and emitted light at imaging times prior to, during, and subsequent to said electrophoretic collision. The device 100 further includes a computing device 122 configured to receive, from the spectroscopic-imaging device 120, and process the at least one of image data and spectroscopic data to provide information concerning at least one of a spatial location of the electrophoretic collision of the at least a portion of the first and second reagents, a change in concentration of at least a portion of the first and second reagents, a detection of the existence of a reaction-product resulting from the electrophoretic collision, a measurement of the concentration of a reaction-product resulting from the electrophoretic collision, a yield of a reaction-product resulting from the electrophoretic collision, an electrophoretic mobility of a reaction-product resulting from the electrophoretic collision, a rate constant associated with a reaction-product resulting from the electrophoretic collision, and a temporal stability of a reaction-product resulting from the electrophoretic collision. The electric field 116 results from applying a voltage across a first electrode 112 immersed in the electrolyte solution 107 and a second electrode 114 immersed in the electrolyte solution 107 thereby generating an ionic current that flows between the first electrode 112 and the second electrode 114. The computing device 122 is further configured to measure a space-time plot from the at least one of image data and spectroscopic data.

In some embodiments, the pair of electrodes 112, 114 can be two platinum (Pt) wire electrodes mounted in an electrophoretic chamber 104. However, the general concepts of this invention are not limited to only Pt wires and are not limited to only two wires. Other types and configurations of wires that can provide the electric field 116 can be used in alternative embodiments. The electrophoretic chamber 104 can be constructed from acrylic polymer sheets, for example, that are cut and fused together according to some embodiments of the current invention. Since Pt is expensive, these electrodes 112, 114 can be soldered to an electrical connector (e.g. BNC or banana type) and two standard electrical cables can be connected to terminals of the power supply. Materials other than Pt can be used for the electrode wires, but typically these other materials must be inert to redox reactions occurring at the electrodes; otherwise at least one electrode oxidizes and becomes corroded; this can adversely affect the equipment as well as reliability of electrophoretic propagation velocities. Such redox reactions at the Pt electrodes occur when the power supply is turned on to create the electric field by applying a voltage across these electrodes; these reactions at the electrodes can produce gas and therefore bubbles, which we prevent from going into the viewing region by two porous polymer mesh films each placed between an electrode 112, 114 and the gel matrix 106. These bubbles rise to the surface of the electrolyte solution and otherwise disturb the types of images we acquire in the geometry we show in FIG. 1A unless we use the porous mesh film. Typical mesh size of this film is around 0.2 to 1 mm. The chamber we show in FIG. 1A is a horizontal slab gel electrophoresis chamber. There are vertical versions of slab gel electrophoresis chambers (this is common especially for use of polyacrylamide gels), and some embodiments of the current invention can be practiced with those too, although the exact relative locations of the components in FIG. 1A would be somewhat different for a vertical gel electrophoresis chamber.

In some embodiments, the device 100 can also include a temperature regulator 124 configured to control a temperature of the electrophoretic chamber 104, the matrix 106, the electrolyte solution 107, the said first and second reagents. The temperature regulator 124 can include a hot plate, a Peltier device, or other approaches to provide and control heat transfer. The electric field 116 is uniform in the matrix 106. The matrix 106 of a porous solid material filled with an electrolyte solution 107 can be an electrophoretic gel filled with an aqueous buffer solution having a prespecified type, prespecified pH, and pre-specified concentration. The electrophoretic gel according to some embodiments defines a plurality of electrophoretic wells, for example 108, 110 into which the first and second reagents are fluidically injected. The electrophoretic wells 108, 110 containing the first and second reagents lie along an electric field line of the electric field 116. In an embodiment, the electrophoretic wells 108, 110 each have the shape of a rectangular prism. The electrophoretic propagation of the at least a portion of the first and second reagents is at least one of counter-propagating, uni-propagating, and co-propagating, and the reaction-product has at least one of a different spectroscopic property, a different fluorescence property, and a different propagation rate than either of the at least a portion of the first and second reagents.

Another embodiment of the current invention is directed to an electrophoretic gel. In some embodiments, the electrophoretic gel includes a matrix 106 of porous solid material and an electrolyte solution 107 disposed within pores of the matrix 106. The matrix 106 defines a plurality of rectangular prismatic wells 108, 110, 126, 128, 130, 132 devoid of said porous solid material to be suitable for producing electrophoretic propagation and collision of reagents when loaded in said rectangular prismatic wells 108, 110, 126, 128, 130, 132 that at least one of counter-propagate, co-propagate, and uni-propagate during use. Each of the plurality of rectangular prismatic wells 108, 110, 126, 128, 130, 132 has a same orientation. A first lane of the matrix defines at least a first rectangular prismatic well 108, a second rectangular prismatic well 110, and a third rectangular prismatic well (not show in FIG. 1A) out of the plurality of rectangular prismatic wells. (See, for example, FIG. 6F.) A second lane of said matrix defines at least a fourth rectangular prismatic well 126, a fifth rectangular prismatic well 128, and a sixth rectangular prismatic well (not show in FIG. 1A) out of the plurality of rectangular prismatic wells. (See, for example, FIG. 6F.) A first separation distance between the first rectangular prismatic well 108 and the second rectangular prismatic well 110 in the first lane is equal to a second separation distance between the fourth rectangular prismatic well 126 and the fifth rectangular prismatic well 128 in the second lane. A third separation distance between the second rectangular prismatic well and the third rectangular prismatic well in the first lane is equal to a fourth separation distance between the fifth rectangular prismatic well and the sixth rectangular prismatic well in the second lane. A minimum spatial dimension of the first and second rectangular prismatic wells 108, 110 lies along a line between a first center of the first rectangular prismatic well 108 and a second center of the second rectangular prismatic well 110 in the first lane.

Example Results

Figure 7A:
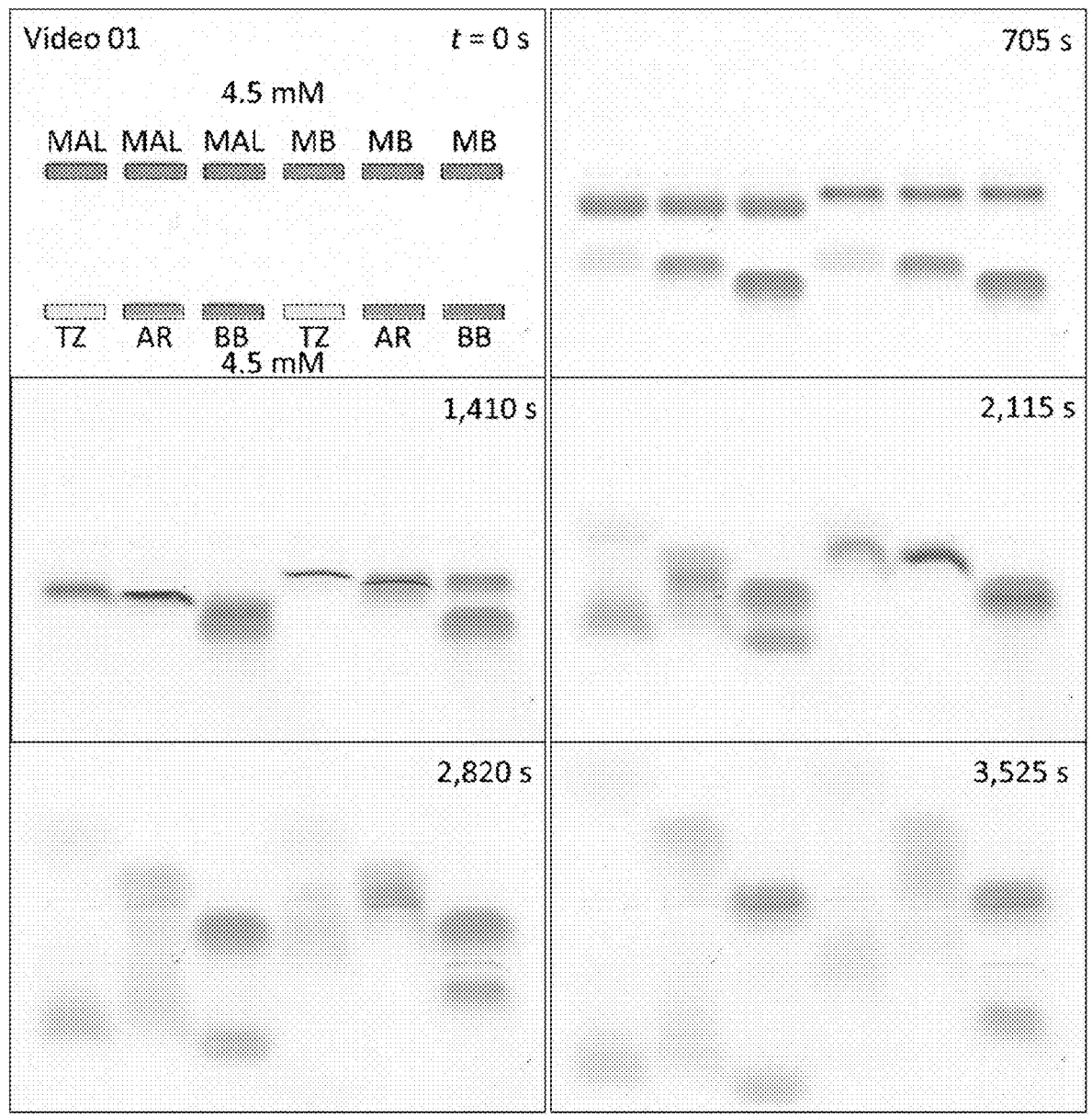
FIG. 7A shows examples of BCGE of oppositely charged dyes in three different lanes, with 2 wells per lane, revealing complex formation. 4.5 mM bands of anionic TZ, AR, and BB collide with cationic MAL and MB as designated. 5 mM SBB at pH=9.0 in a 3% (w/w) agarose gel at an electric field strength $1E1=3.1$ V/cm. Anionic dyes propagate upward; cationic dyes propagate downward. Scale: wells measure 6.5 mm wide. Times after turning on the electric field are shown in the upper right in each panel in seconds.

To facilitate subsequent BCGE experiments, we first measure $\mu_e$ of organic dye molecules in agarose gels and compare these $\mu_e$ to mobilities predicted by the Smoluchowski equation[53] and molecular models (see Methods, Supplementary Methods, FIGS. 8A-8J, FIGS. 9A-9J). Knowing these $\mu_e$, we then design and cast agarose gels having two or more wells in each lane, and we systematically explore complex spatio-temporal patterns that can form when counter-propagating bands of dye molecules collide (see e.g. FIG. 7A). We demonstrate this first for complexing and precipitation reactions, summarizing the videos using space-time plots. We also show examples of acid-base, ligand-exchange, and redox reactions, and we generalize the reagents to include colloidal nanoparticles.

Figure 2A:
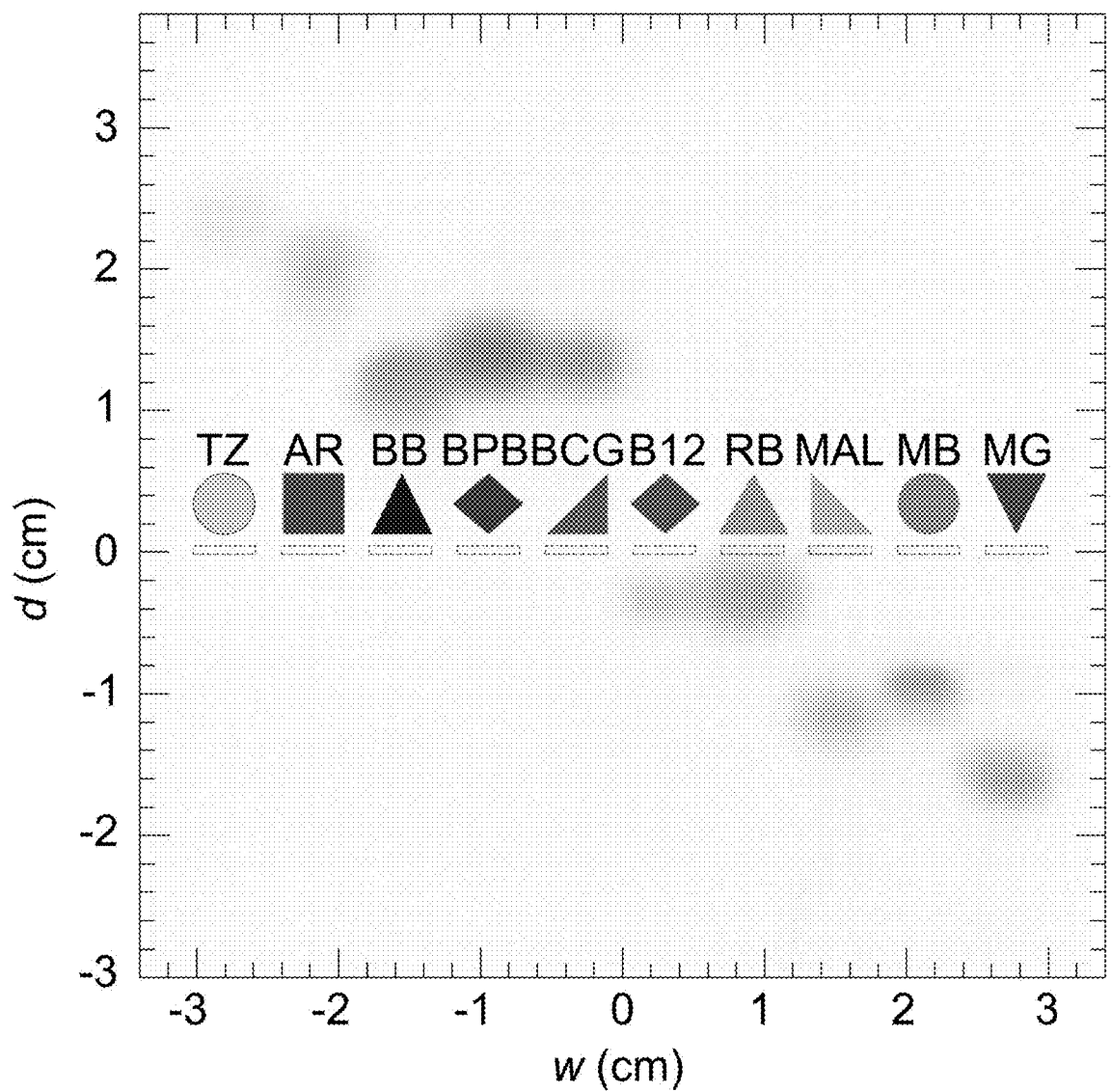
FIG. 2A shows bands of dye molecules after a propagation time t=2,400 s from wells (dashed rectangles at d=0). Propagation distance along the applied field is d; transverse distance between different lanes is w. Dyes are identified by abbreviations (see Table 1) and assigned symbols. Conditions: 3.0% (w/w) agarose gels; 5.0 mM SBB at pH 9.0; applied electric field E=3.1 V/cm. Each lane is labeled with the corresponding dye's abbreviation.
Figure 2B:
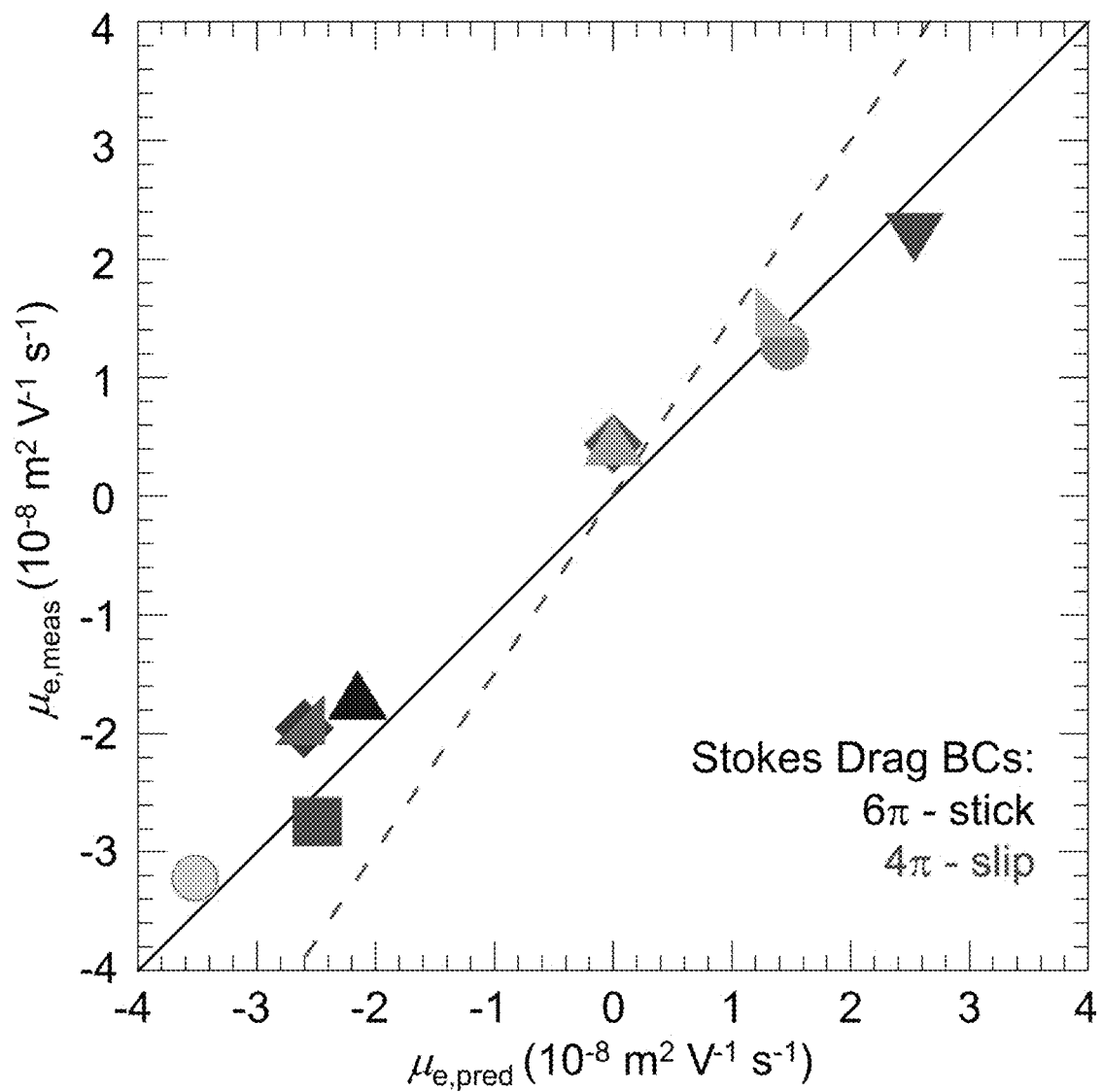
FIG. 2B shows a comparison of measured and predicted electrophoretic mobilities, $\mu_{e,meas}$ and $\mu_{e,pred}$, respectively, of organic dyes using the Smoluchowski equation with stick boundary conditions for Stokes drag and effective hydrodynamic radii from molecular modeling (points). Black solid line: $\mu_{e,meas}=\mu_{e,pred}$ (stick) has ideal slope=1.
Figure 7B:
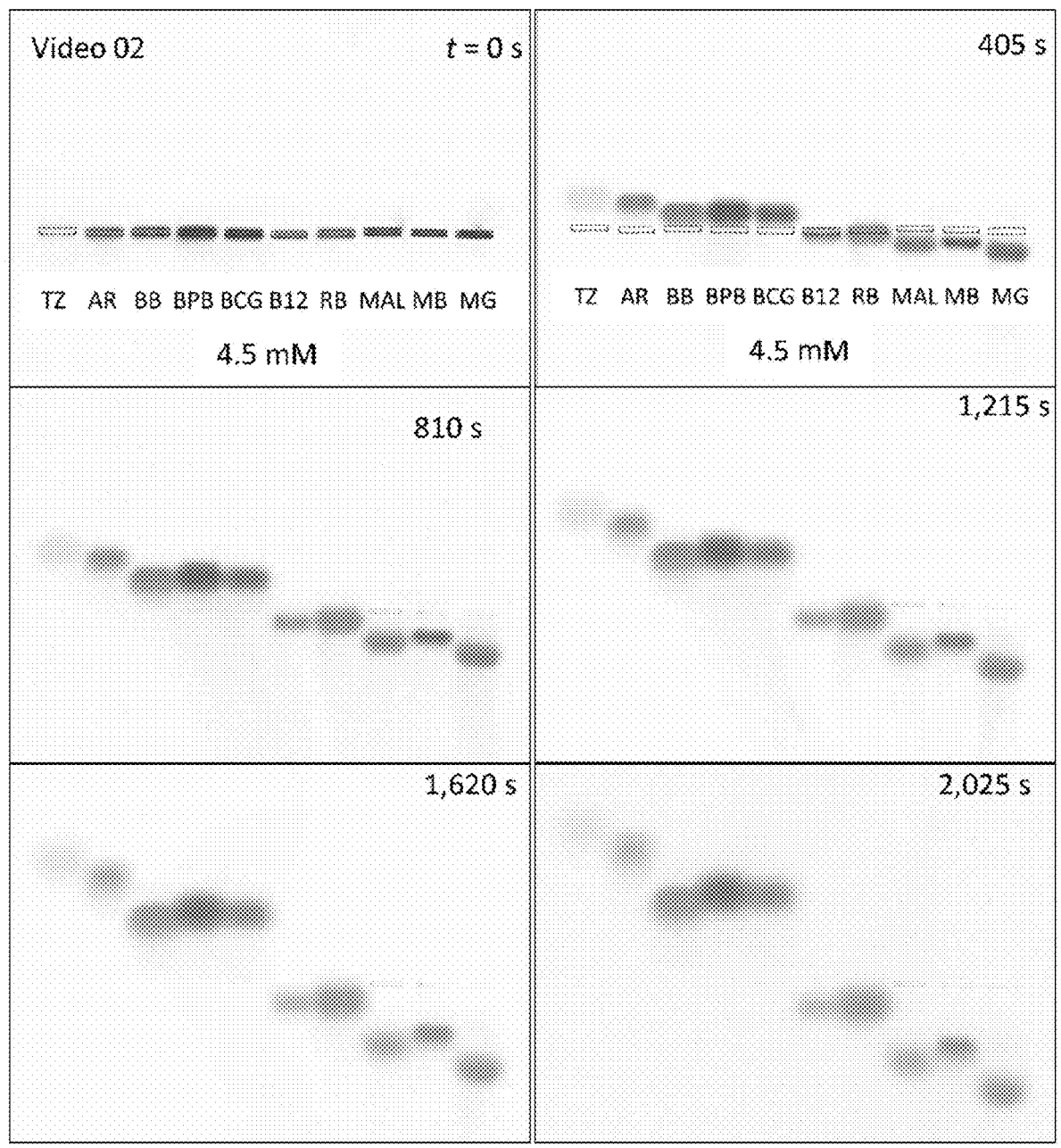
FIG. 7B shows electrophoresis of organic dye molecules to yield measured mobilities. Bands of organic dyes (see Table 1) propagate in a 3.0% (w/w) agarose gel in 5 mM SBB at pH=9.0 at an electric field $|E|=3.1$ V/cm. Left to right, dyes are TZ, AR, BB, BPB, BCG, B12, RB, MAL, MB, and MG (see FIG. 2A). Scale: dashed-line wells are 4.5 mm wide for this and subsequent movies. Times after turning on the electric field are shown in the upper right in each panel in seconds.

Electrophoretic mobilities of dye molecules. Using agarose GE in 5.0 mM sodium borate buffer (SBB) at pH=9.0 at an electric field of E=3.1 V/cm in the linear propagation regime (see Methods), we measure average velocities v of a set of dye molecules (for identifying properties and abbreviations see FIGS. 8A-8J) based on observed propagation distances of bands (FIG. 2A, FIG. 7B), from which we determine $\mu_{e,meas}=v|E_c$. Moreover, in FIG. 2B, we compare these $\mu_{e,meas}$ to predictions given by the Smoluchowski equation using either slip or stick boundary conditions in the Stokes drag factor, $\mu_{e,pred}=q/(C\eta_{eff}a)$, where a is the translational hydrodynamic radius of a given dye (see Methods), $\eta_{eff}$ is the effective viscosity of the liquid outside the molecules in the porous gel, and $C=4\pi$ for slip or $C=6\pi$ for stick boundary conditions. Since the average pore size of the gel[54] is much larger than the size of all dye molecules, we assume $\eta_{eff}\approx 1$ mPa s (i.e. the viscosity of water at room temperature) in $\mu_{e,pred}$, and we find that stick boundary conditions yield better overall agreement with $\mu_{e,meas}$.

Figure 3A:
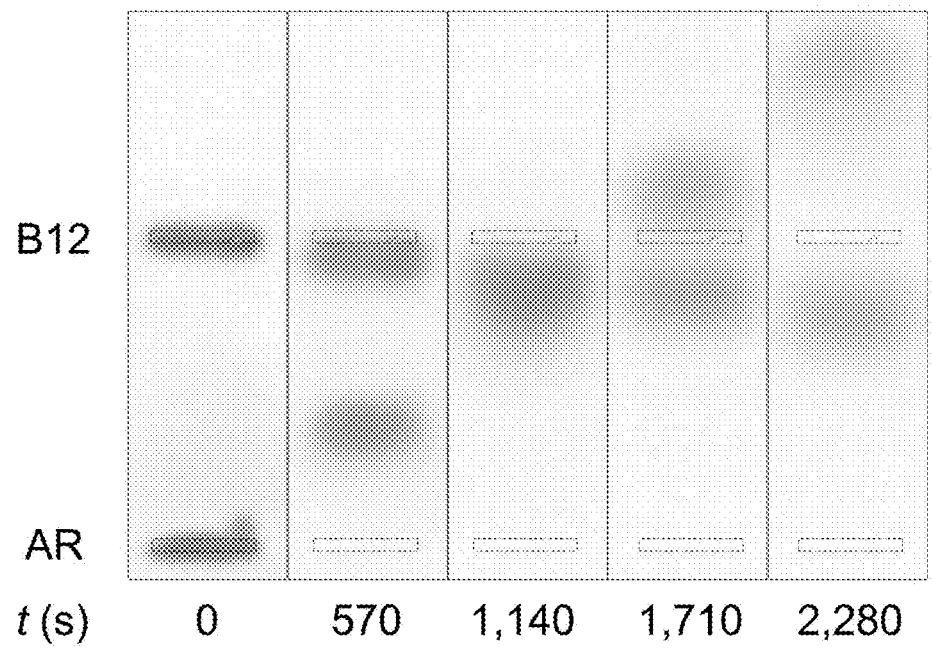
FIG. 3A shows an optical visualization of complexing and decomplexing reactions between counter-propagating bands of the organic dyes B12 and AR using BCGE at different times t after turning on a uniform electric field E. Overhead images are background-subtracted with an image of the unloaded gel to improve clarity. Arrows indicate complex formation. Conditions: 3.0% (w/w) agarose gel concentration, 5.0 mM sodium borate buffer at pH 9.0; electric field strength E=3.1 V/cm; 2 wells per lane. Each well is loaded with 4 µL of a dye solution at 4.5 mM. 12 mm distances between wells in same lane. Each well measures 4 mm wide.
Figure 3B:
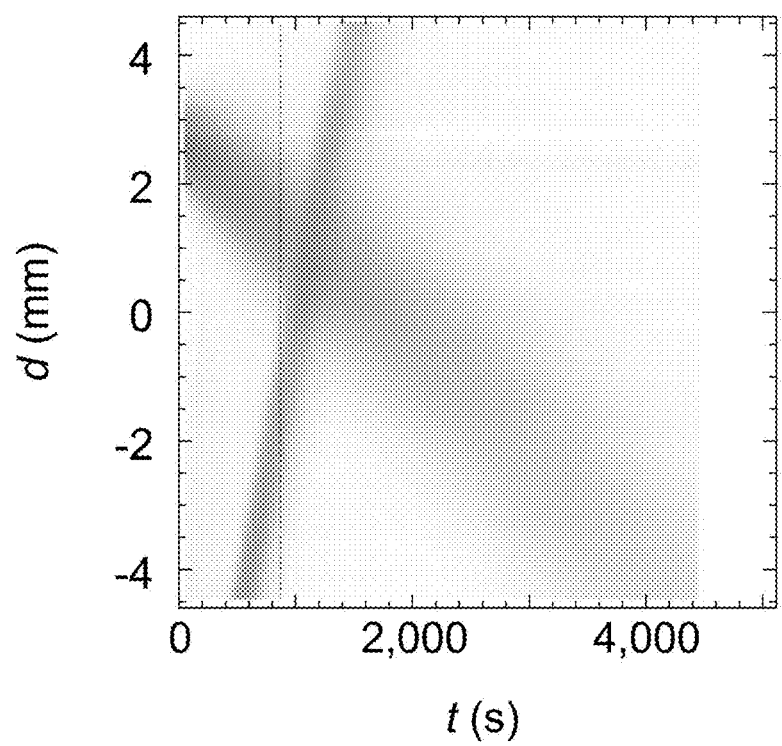
FIG. 3B shows a space-time plot of the center strip of pixels in the lane from FIG. 3A, where the spatial position d along the lane is set to zero at the collision point.
Figure 3C:
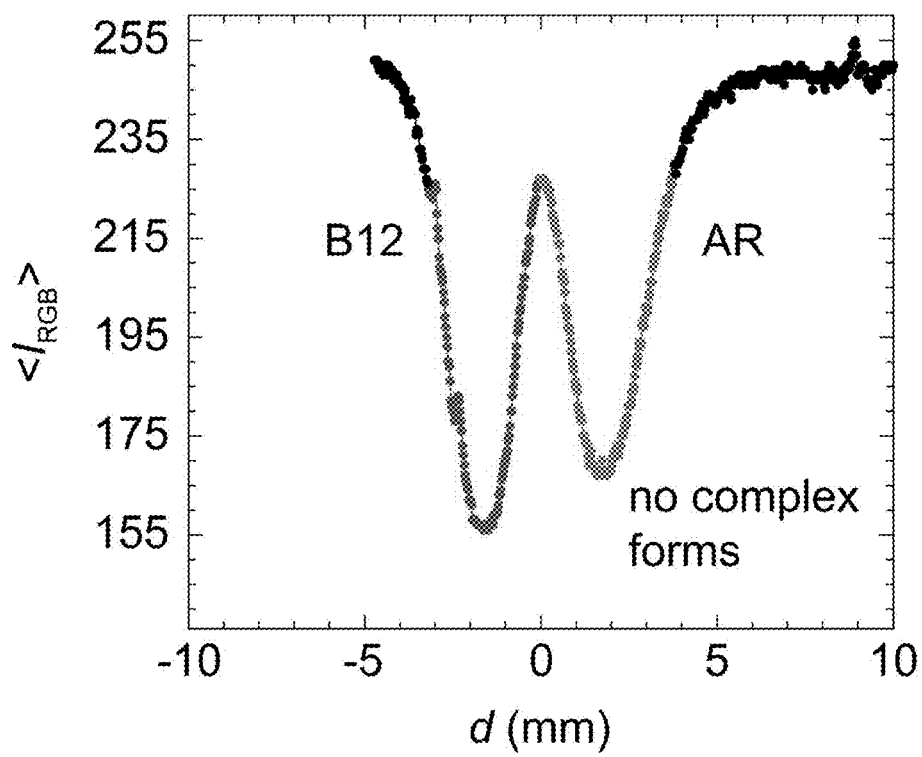
FIG. 3C shows an average red-green-blue (RGB) color image intensity $I_{RGB}$ spatial profile at a particular time (corresponding to red dashed line in FIG. 3B).
Figure 3D:
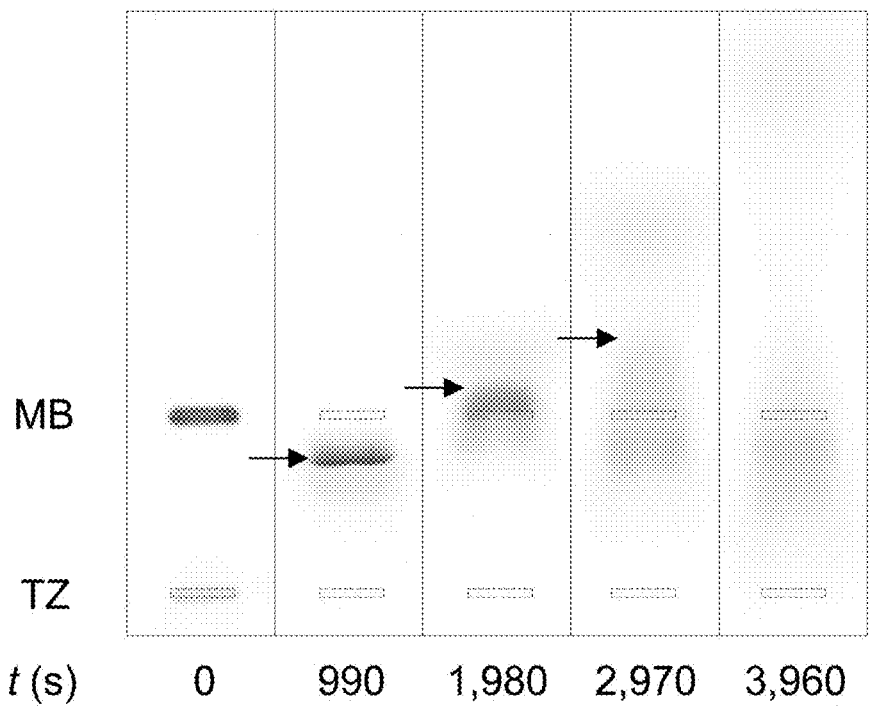
FIG. 3D shows an optical visualization of complexing and decomplexing reactions between counter-propagating bands of organic dyes MB and TZ using BCGE. Conditions and dimensions are the same as in FIG. 3A.
Figure 3E:
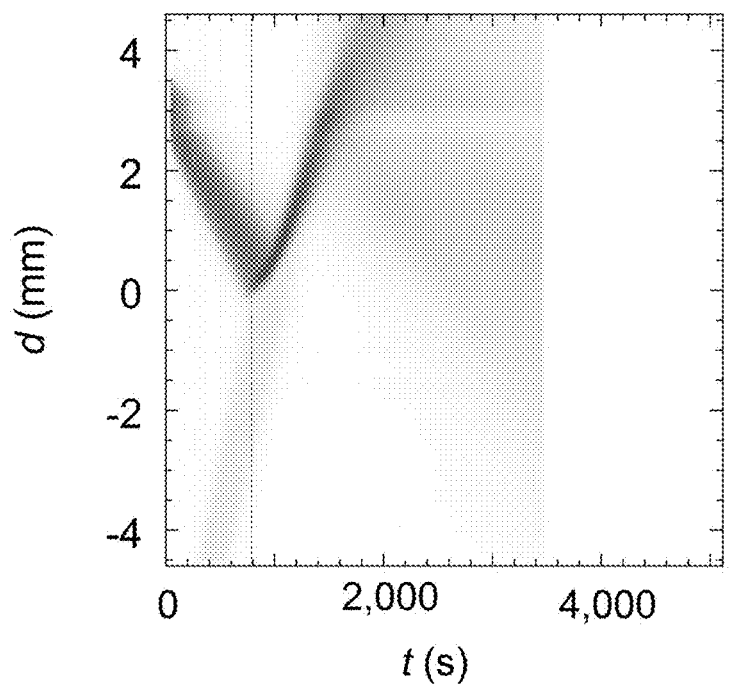
FIG. 3E shows a space-time plot of the center strip of pixels in the lane from FIG. 3D, where the spatial position d along the lane is set to zero at the collision point.
Figure 3F:
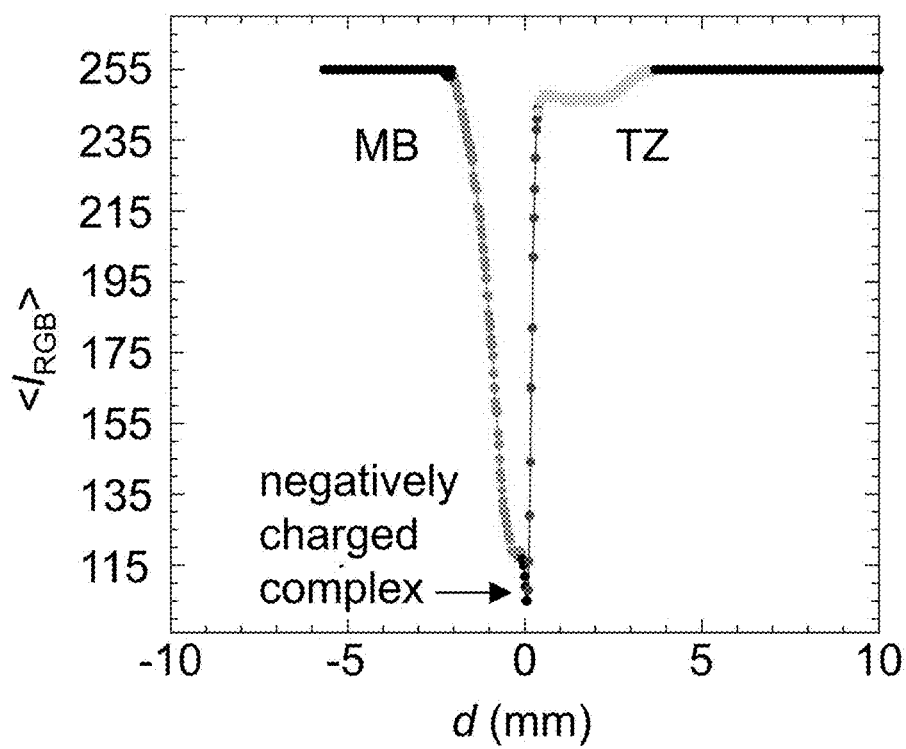
FIG. 3F shows an average RGB color image intensity $I_{RGB}$ spatial profile at a particular time (corresponding to red dashed line in FIG. 3E).
Figure 3G:
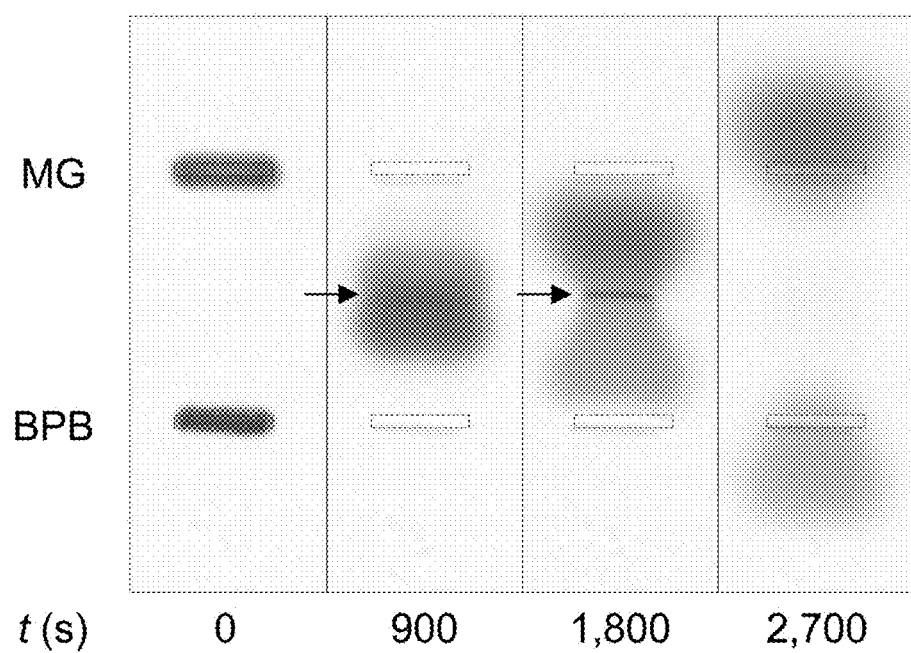
FIG. 3G shows an optical visualization of complexing and decomplexing reactions between counter-propagating bands of organic dyes MG and BPB using BCGE. Conditions and dimensions are the same as in FIG. 3A.
Figure 3H:
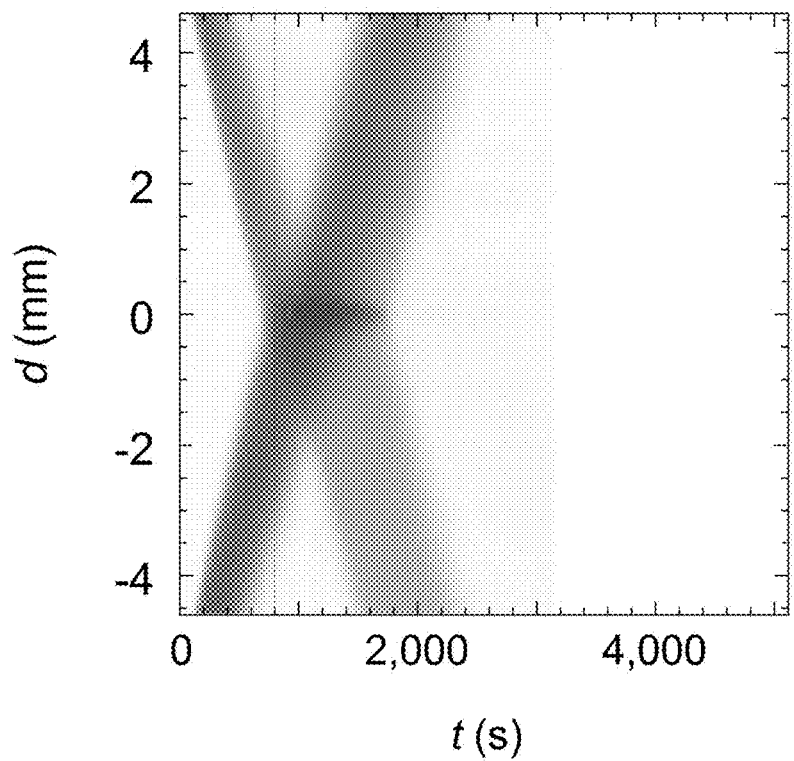
FIG. 3H shows a space-time plot of the center strip of pixels in the lane from FIG. 3G, where the spatial position d along the lane is set to zero at the collision point.
Figure 3I:
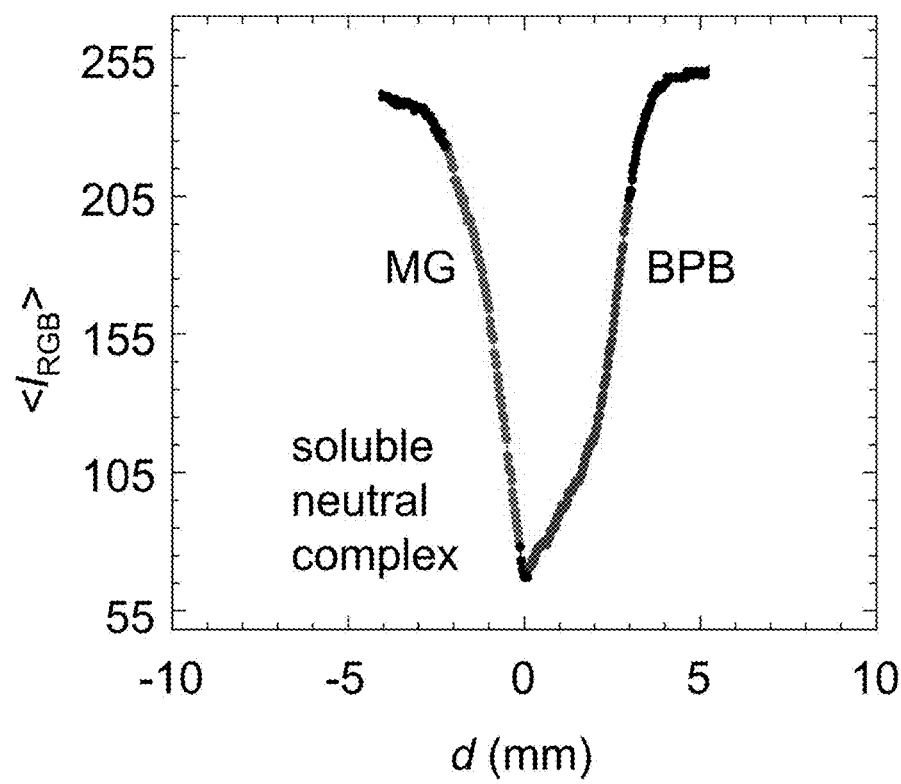
FIG. 3I shows an average RGB color image intensity $I_{RGB}$ spatial profile at a particular time (corresponding to red dashed line in FIG. 3H).
Figure 3J:
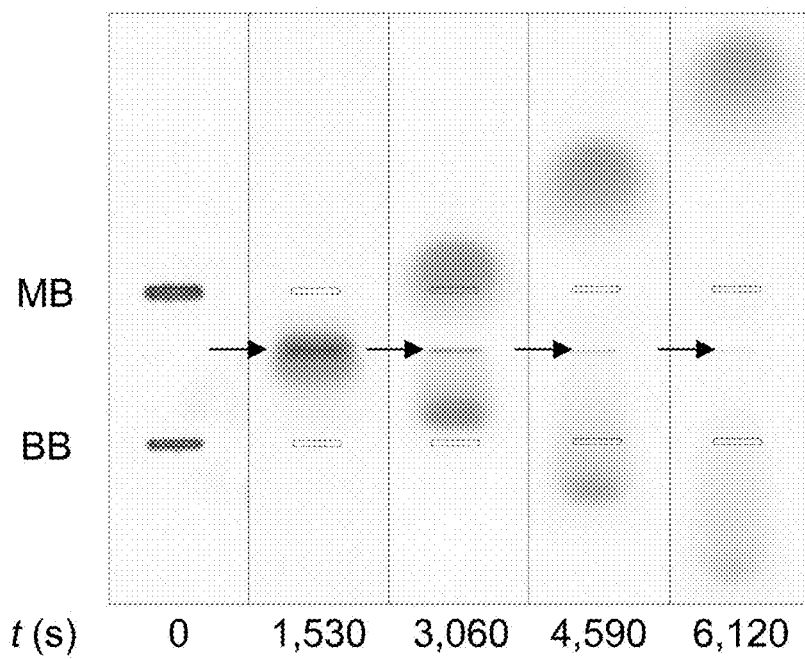
FIG. 3J shows an optical visualization of complexing and decomplexing reactions between counter-propagating bands of organic dyes MB and BB using BCGE. Conditions and dimensions are the same as in FIG. 3A.
Figure 3K:
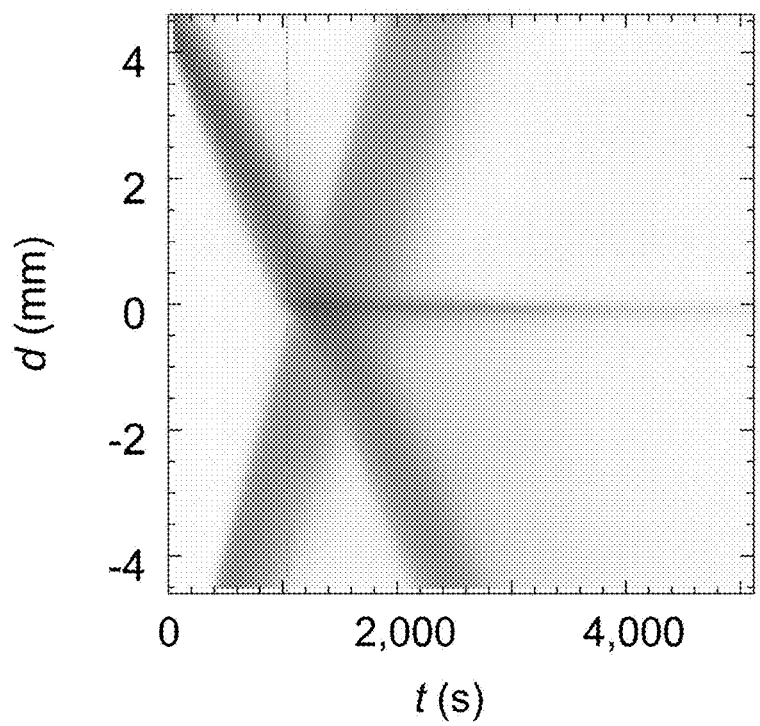
FIG. 3K shows a space-time plot of the center strip of pixels in the lane from FIG. 3J, where the spatial position d along the lane is set to zero at the collision point.
Figure 3L:
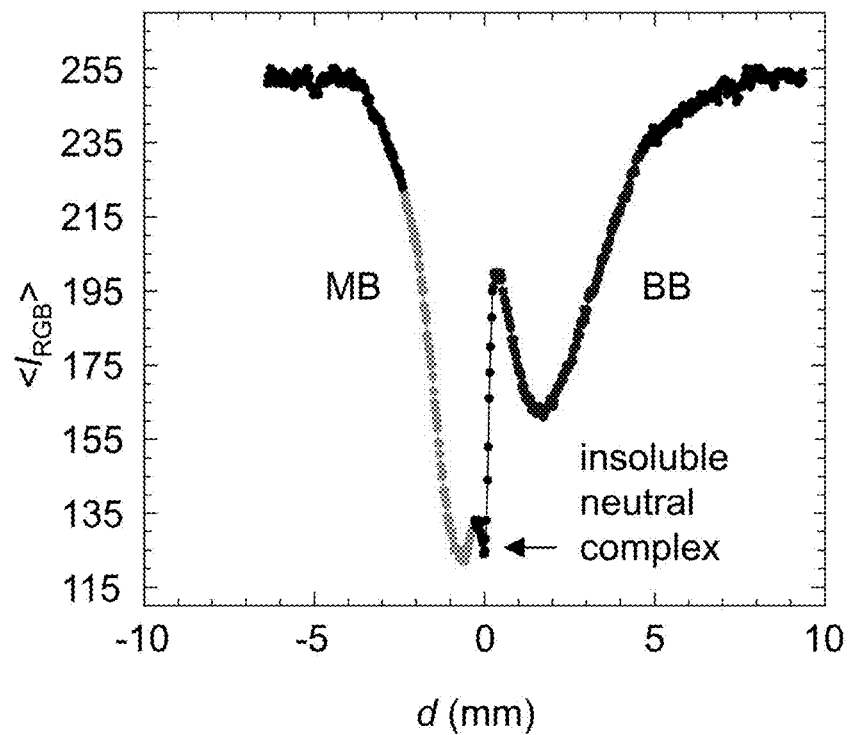
FIG. 3L shows an average RGB color image intensity $I_{RGB}$ spatial profile at a particular time (corresponding to red dashed line in FIG. 3K).
Figure 7C:
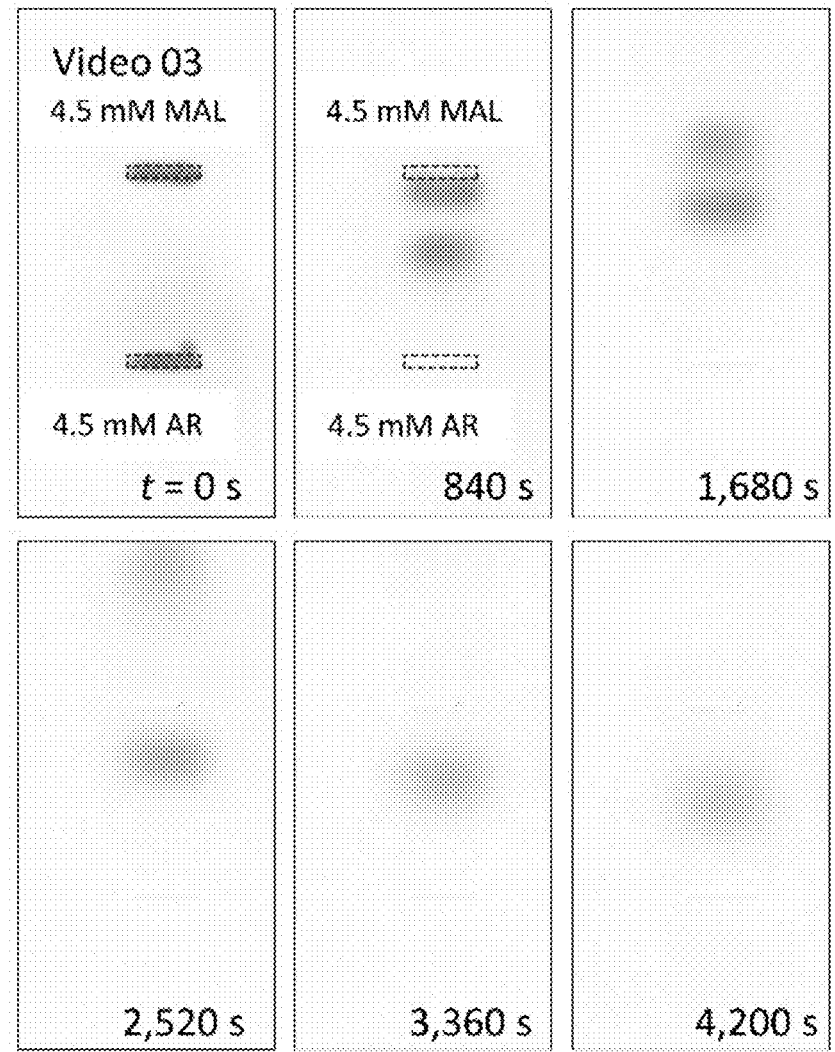
FIG. 7C shows bands of B12 and AR(−2e) colliding and passing through each other without interacting. 4.5 mM bands of near-neutral B12 and anionic AR collide (FIG. 3A). Conditions: same as in FIG. 7B. Times after turning on the electric field are shown in the lower right in each panel in seconds.
Figure 7D:
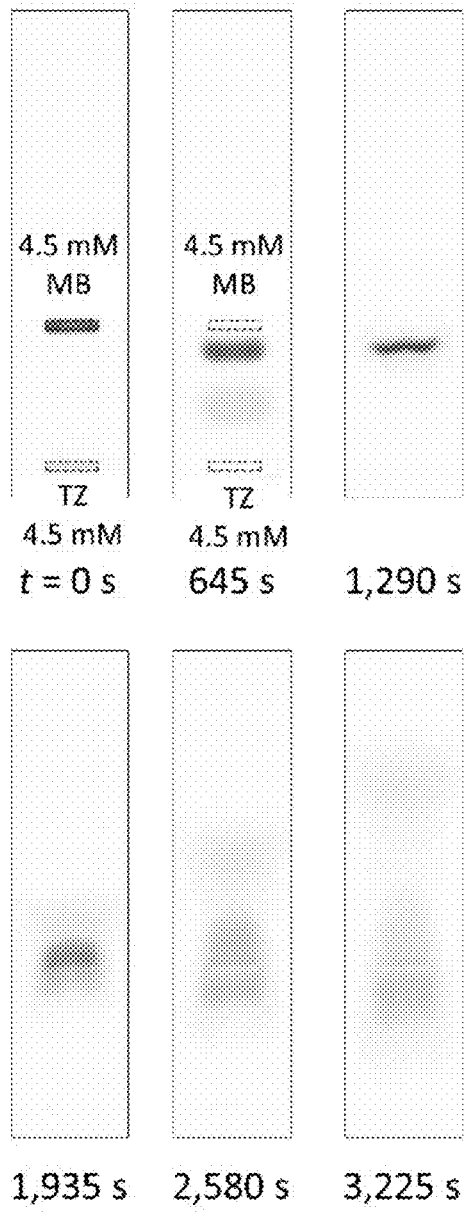
FIG. 7D shows BCGE of equimolar TZ(−3e) and MB(+1e) to yield anionically charged complexes. 4.5 mM bands of anionic TZ and cationic MB collide, demonstrating strong attractive interaction and complex formation without neutralization (FIG. 3D). Conditions: same as in FIG. 7B. Times after turning on the electric field are shown below each panel in seconds.

Visualizing complex formation between colliding dye pulses. To explore interactions between dye molecules, as examples, we have performed BCGE on four dye pairs, B12/AR, MB/TZ, MG/BPB, and MB/BB (for definitions of abbreviations and properties see FIGS. 8A-8J) at a fixed 1:1 stoichiometric ratio of 4.5 mM initial dye concentrations (FIG. 3A), chosen to be large enough to make attractive associations between dye molecules easy to visualize. Bands of neutral B12 and anionic AR simply pass through each other unperturbed (FIG. 3A, FIG. 7C), indicating negligible attractive interactions. We construct a space-time plot by concatenating vertical strips of pixels from the center of a given lane for each recorded image (see Methods), and we find a constant velocity of propagation for both B12 and AR before, during, and after collision (FIG. 3B). At the onset of band collision, intensity analysis of this central vertical strip of pixels also reveals two rounded minima in the intensity without additional sharper features (FIG. 3C). By contrast, the other pairs show very different behavior. For instance, when TZ(−3e) collides with counter-propagating MB(+e), it actually reverses the propagation direction of nearly all MB ions, indicating strongly attractive charge interactions leading to predominantly anionic complex formation (FIG. 3D, FIG. 7D). This is highlighted by the very different appearance of the associated space-time plot (FIG. 3E), showing a zig-zag pattern for MB, and the intensity analysis at onset of collision, which reveals a spike-like minimum (FIG. 3F), indicating complex formation. Subsequently, these net anionic complexes dissociate as they are continuously subjected to thermal-entropic Brownian fluctuations in the presence of the electric field. Ultimately, these stochastically excited complexes dissociate, and the dissociation products are separated by the electric field, yielding a smear in the space-time plot at longer times, which indicates that this reaction is reversible. The collision of BPB(−2e) and MG(+2e), which involves a 1:1 charge ratio and nearly the same $|\mu_{e,meas}|$, also shows strong evidence of complexing by generating a dark stationary band (FIG. 3G-arrows). At later times, this band slowly disappears, as the combination of thermal-entropic fluctuations cause decomplexing and the electric field pulls apart and separates these dye ions, yielding a symmetric two-color butterfly pattern. This dark band appears prominently as a persistent horizontal region in the space-time plot (FIG. 3H), corresponding to a spike-like minimum in the intensity after the onset of collision (FIG. 3I). As yet a different example, when a band of BB(−2e) collides with MB(+e), nearly all of the MB is consumed in a complexing reaction that generates a very long-lived stationary band, whereas a significant fraction of the more highly charged BB propagates through the collision without reacting (FIGS. 3J-3L). Thus, MB is the limiting reagent in this case. The very long lifetime of this stationary band may indicate not only that neutral complexes are formed but also that these complexes can aggregate locally into larger precipitates. Over time, this stationary band very slowly disappears, indicating that dissolution of the precipitates as well as dissociation of the complexes is likely occurring.

Figure 4A:
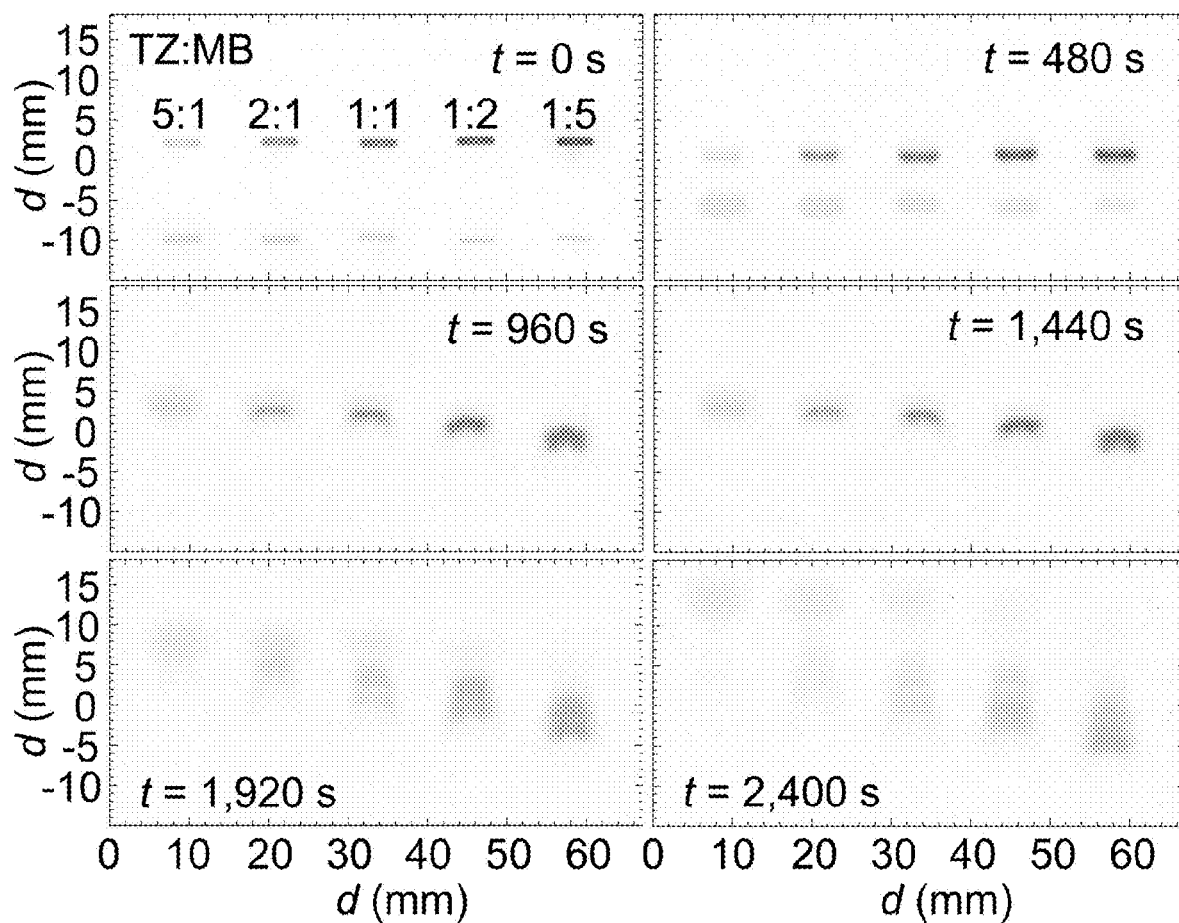
FIG. 4A shows concentration-dependent deflections of band trajectories in space-time plots between complexing dyes TZ(-3e, yellow) and MB(+e, blue) using BCGE. Conditions: same as in FIG. 2A. 12 mm distance between 2 wells. Background-subtracted overhead images are displayed at times t=0, 480, 960, 1,440, 1,920, and 2,400 s after turning on E. Upper left: lanes are marked according to concentration ratio TZ:MB at a fixed total concentration of 9.0 mM.
Figure 4B:
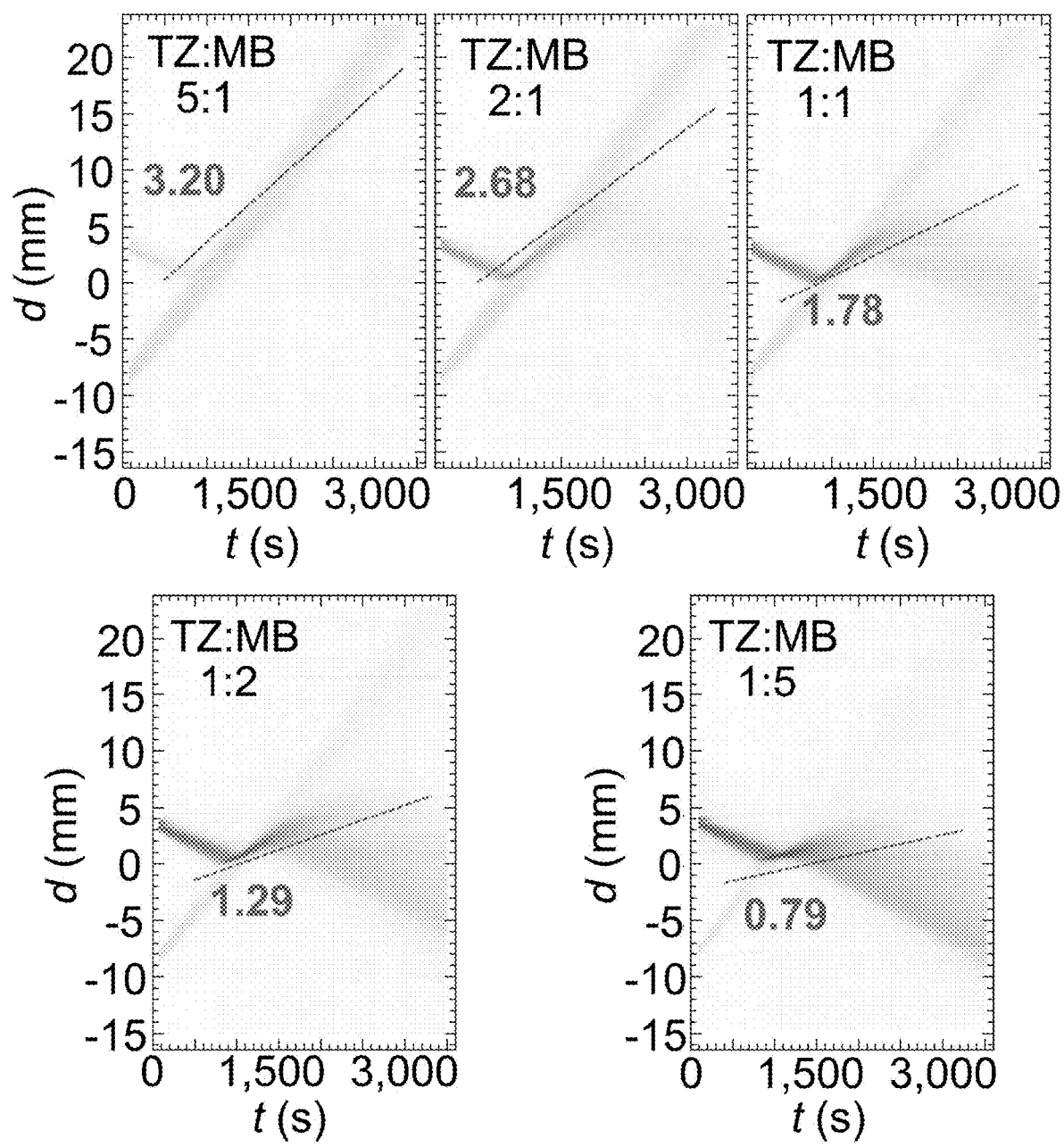
FIG. 4B shows space-time plots of band trajectories of both TZ and MB determined from FIG. 4A. Offset green dashed lines: average trajectories of complexes containing MB immediately after collision; electrophoretic mobilities of these complexes $\mu_{e,meas}$ (green numbers) in units of $10^{-8}$ $m^2 V^{-1} s^{-1}$.
Figure 4C:
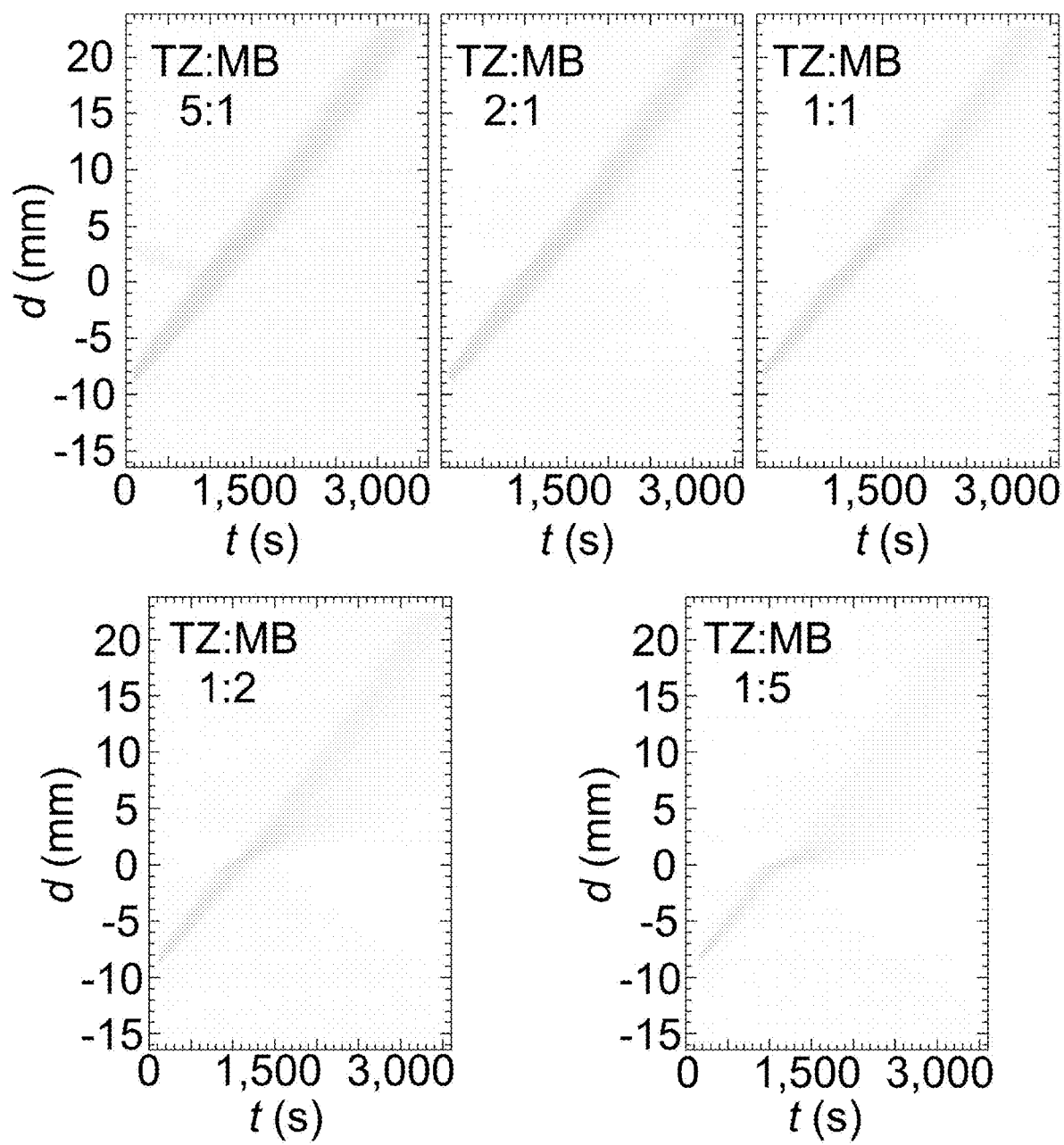
FIG. 4C shows that a separation of a color channel from a RGB space-time plot in FIG. 4B provides an optical absorption space-time plot of only TZ.
Figure 4D:
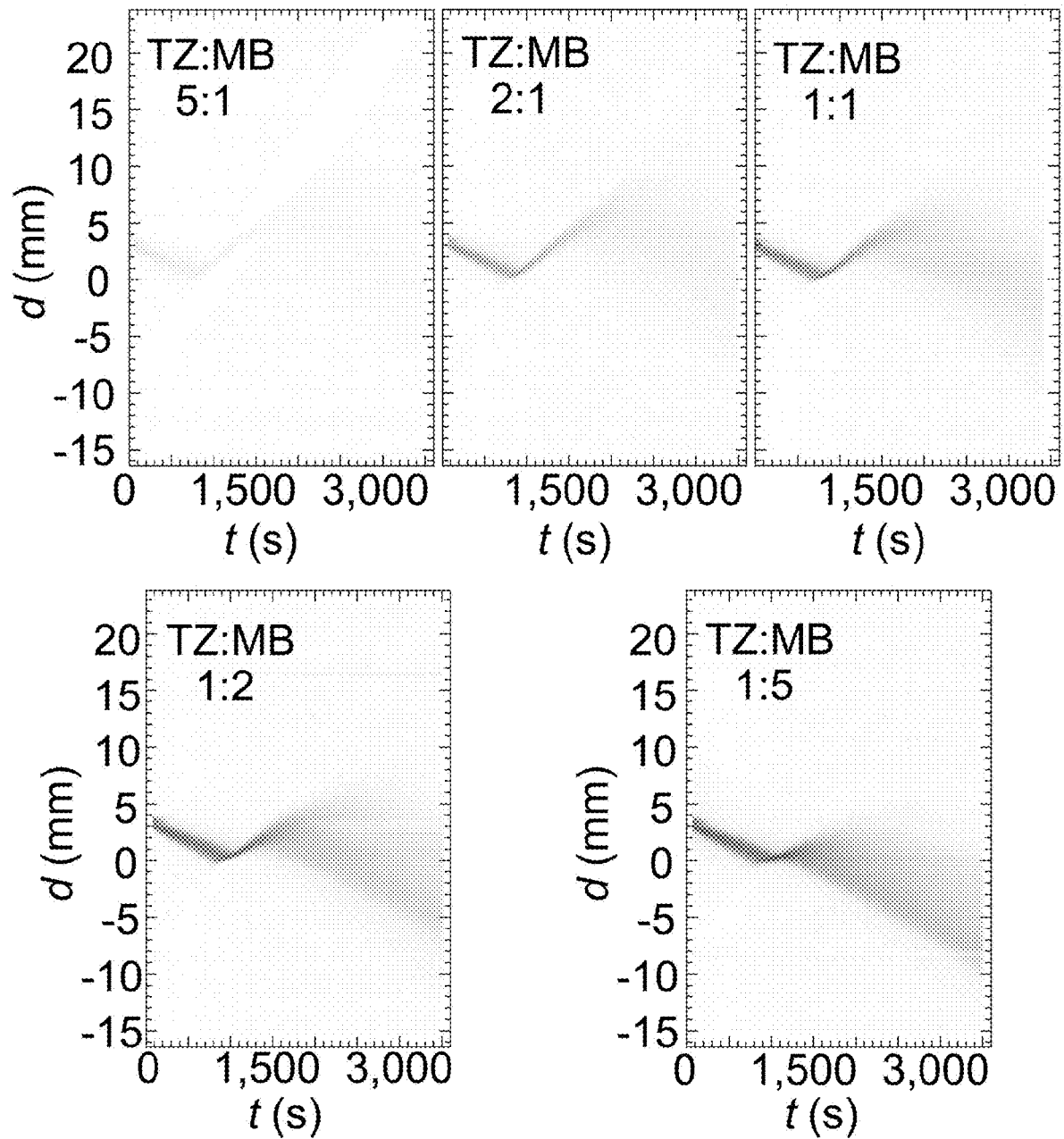
FIG. 4D shows that a separation of a color channel from a RGB space-time plot in FIG. 4B provides an optical absorption space-time plot of only MB.
Figure 7E:
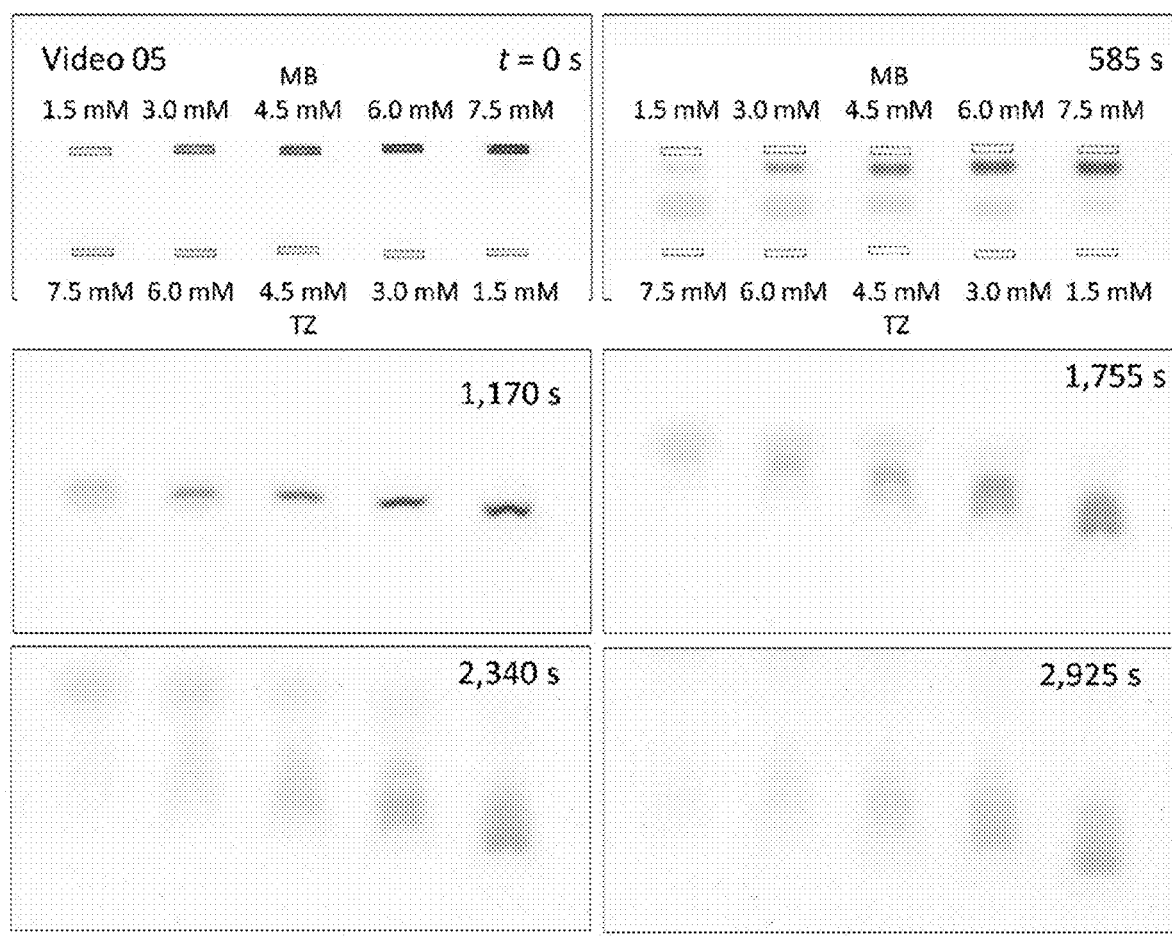
FIG. 7E shows BCGE of TZ(−3e) and MB(+1e) at different relative concentrations. The higher charge and lower stoichiometric ratio of TZ:MB (ranging from 5:1 to 1:5) is apparent at high relative concentrations of MB to TZ for which TZ is noticeably slowed (FIG. 4A). Conditions: same as in FIG. 7B. Times after turning on the electric field are shown in the upper right in each panel in seconds.
Figure 7F:
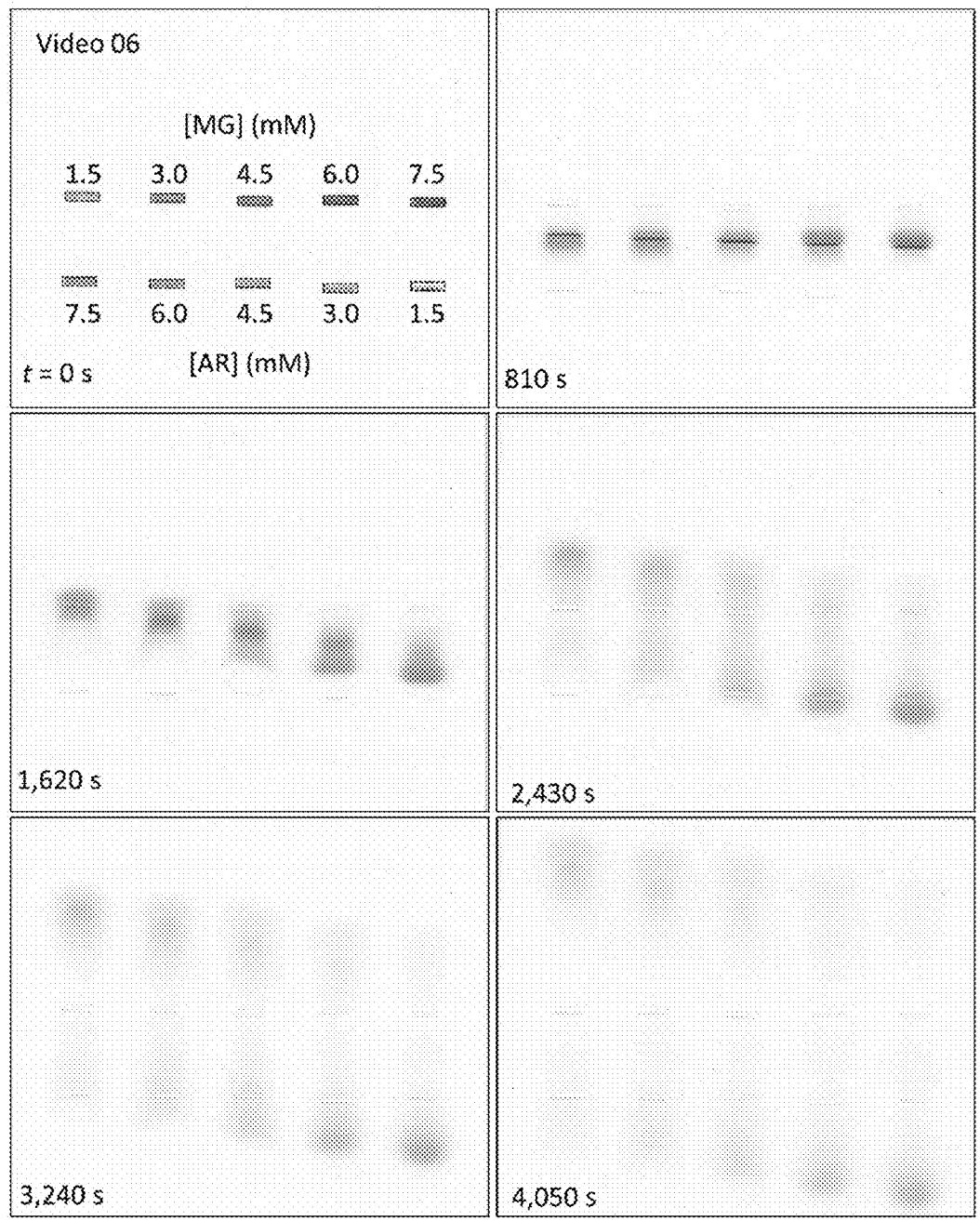
FIG. 7F shows BCGE of AR(−2e) and MG(+2e) at different relative concentrations. For the 1:1 concentration [AR]:[MB], the complex resulting from collision remains relatively stationary, whereas for 5:1 and 1:5, complexes propagate upwards or downwards to a similar extent, respectively. Conditions: same as in FIG. 7B. Times after turning on the electric field are shown in the lower left in each panel in seconds.

Effect of reagent concentrations loaded at fixed volume. To more thoroughly investigate the temporary reversal in the propagation of the band of MB(+e, blue) when it encounters the faster moving and more highly charged counter-propagating band of TZ(−3e, yellow), we have performed BCGE for different molar ratios (TZ:MB) of these reagents ranging from 5:1 to 1:5 at a fixed total concentration of 9.0 mM (FIG. 4A, FIG. 7E). As the molar ratio increases towards higher [MB], the propagation of TZ is more significantly retarded (FIG. 4A), and space-time plots reveal non-linear features in TZ, not just MB (FIG. 4B). By separating color channels (see Methods), we also make space-time plots of TZ only (FIG. 4C) and MB only (FIG. 4D). In contrast, for ratios 5:1 and 2:1, where TZ is dominant both in terms of concentration and charge per molecule, the trajectory of the band of TZ in its space-time plot is not significantly deflected (FIG. 4C). The duration over which MB propagates in the reverse direction after collision is longest at 5:1, and the slope of its trajectory while propagating as a complex with TZ is highest in the space-time plot at 5:1 (FIG. 4B). These slopes of complexed MB trajectories can be understood to represent the mobilities of the complexes formed, which decrease systematically as the molar ratio varies from 5:1 to 1:5 (FIG. 4B- dashed lines), indicating that the complexes, on average, are less negatively charged towards 1:5 (i.e. as [MB] significantly exceeds [TZ]). The post-collision decomplexing behavior leads to significant dispersion and smearing of the bands as they begin to separate and ultimately cease interacting. A similar relative concentration dependence is observed for complexes of MG(+2e) and AR(−2e), which for an equimolar collision forms a stationary complex which dissociates in equal proportions for MG and AR (FIG. 7F). Based on these results, it is clear that the charges and mobilities of reagent species in combination with their relative concentrations and loaded volumes contribute to the complex pattern formation that is seen in BCGE.

Figure 5A:
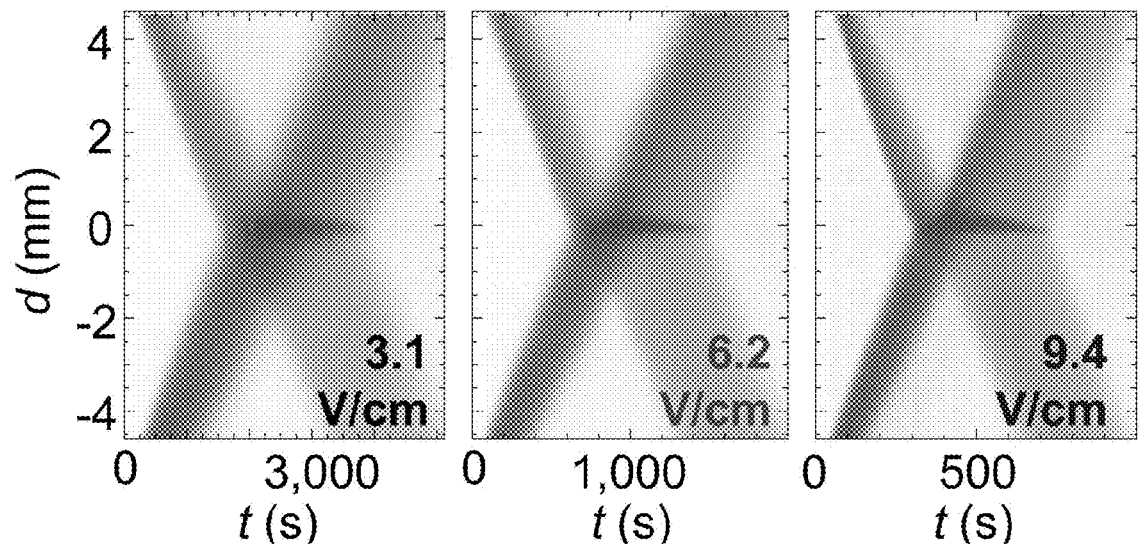
FIG. 5A shows dependence of complexing and decomplexing kinetics on the applied electric field strength using BCGE. Conditions: same as in FIG. 2A, except electric field strength E. Background-subtracted space-time plots of band collisions between MG(+2e) and BPB(-2e) are shown at field strengths E (V/cm) of 3.1 (black, left); 6.2 (red, middle); and 9.4 (blue, right). The range of times shown for 6.2 and 9.4 V/cm have been reduced by factors of 2× and 3×, respectively, yielding similar X-patterns to that shown for 3.1 V/cm.
Figure 5B:
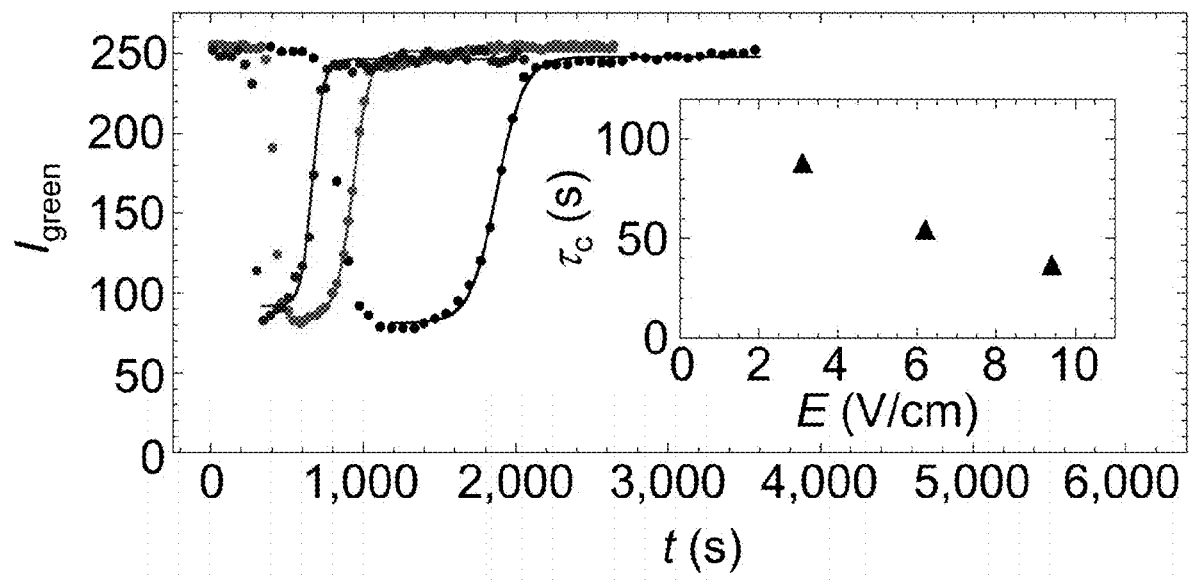
FIG. 5B shows intensity profiles revealing decomplexing kinetics, extracted from FIG. 5A using the green color channel intensity $I_{green}$ taken across d=0 mm, where the stationary product band appears, as a function of time t for different E (points color coded as in FIG. 5A). Lines are fits of long-time data using Fermi-like functions (see Table 2 for fit parameters). Inset: time constant $\tau_c(E)$, obtained from the fit, decreases as a function of E.
Figure 5C:
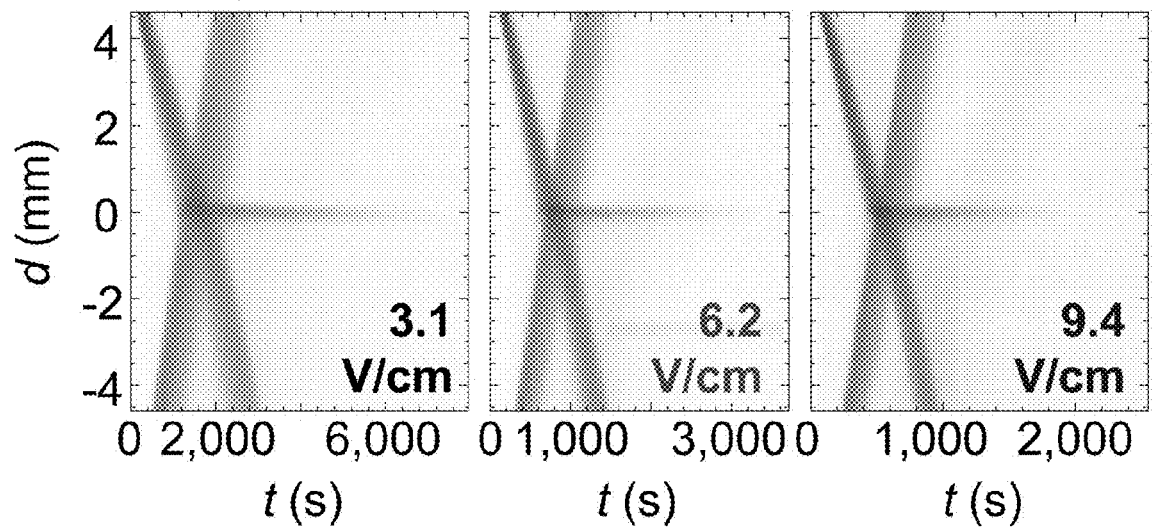
FIG. 5C shows dependence of complexing and decomplexing kinetics on the applied electric field strength using BCGE for dyes MB(+e) and BB(-2e). Conditions and values of E are the same as FIG. 5A.
Figure 5D:
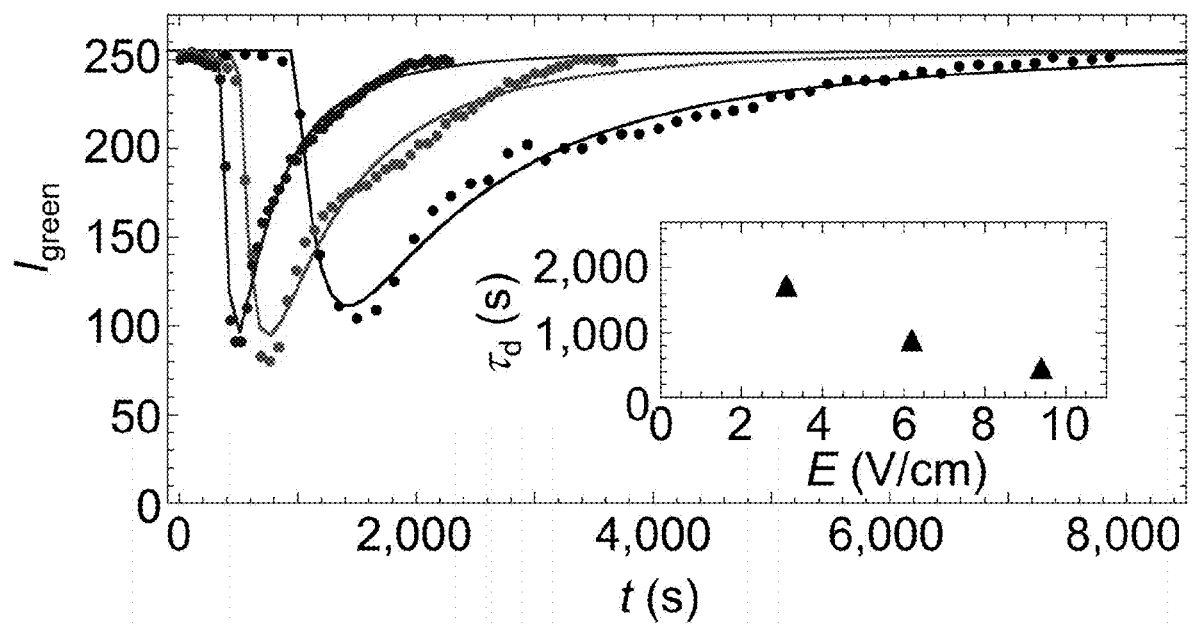
FIG. 5D shows intensity profiles revealing decomplexing kinetics, extracted from FIG. 5C using the green color channel intensity $I_{green}$ taken across d=0 mm. $I_{green}(t)$ is fit to a modified log-normal function (lines, see Table 3 for fit parameters). Inset: $\tau_d$ from the fits decreases for larger E.
Figure 7G:
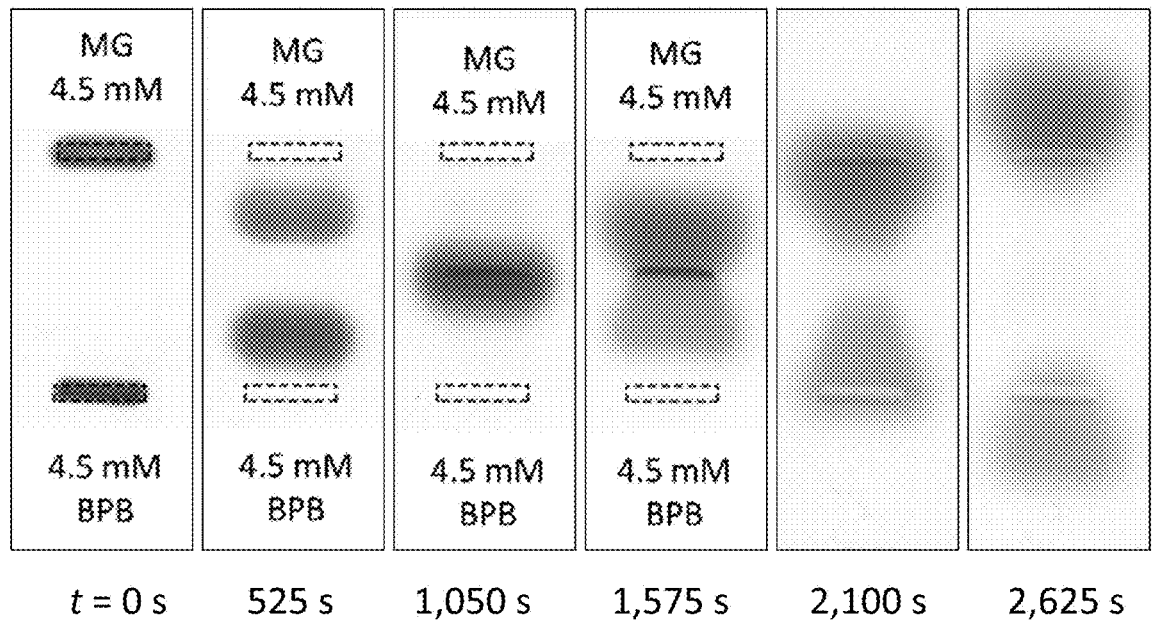
FIG. 7G shows BCGE of BPB(−2e) and MG(+2e) to yield neutral stationary complexes. The complexes formed in a narrow band are clearly stationary, implying neutrality. Subsequent decomplexing leads to a 'butterfly' pattern, consistent with a 1:1 stoichiometric ratio of BPB:MG (FIG. 3G). Conditions: same as in FIG. 7B. Times after turning on the electric field are shown below each panel in seconds.
Figure 7H:
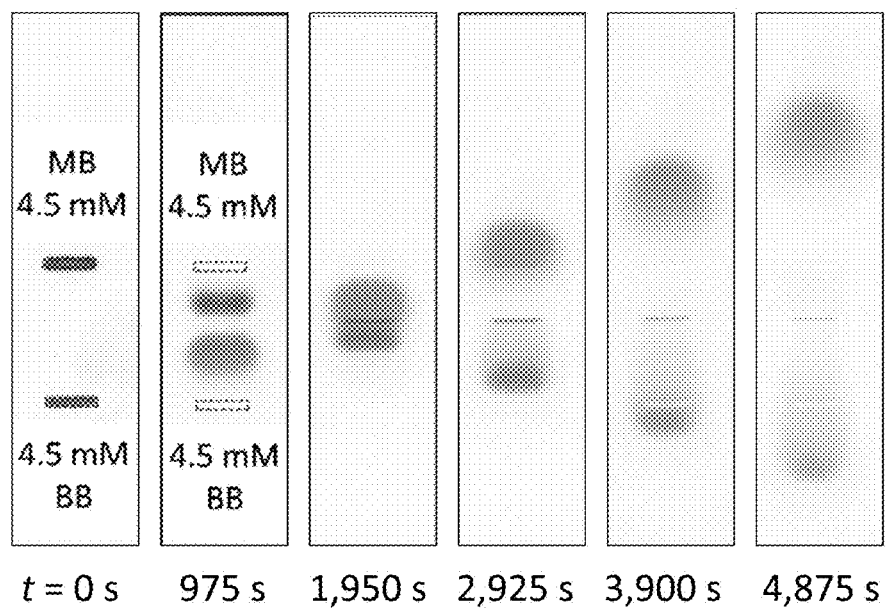
FIG. 7H shows BCGE of BB(−2e) and MB(+1e) to yield a stationary band of a longer-lived insoluble complex-precipitate. The band of complex-precipitate formed upon collision is stationary and only very slowly decomplexes and dissolves, causing a high degree of smearing of bands. Based on differences in the optical absorption as the decomplexing is occurring, the complex appears to be composed of predominantly MB (FIG. 3J). Conditions: same as in FIG. 7B. Times after turning on the electric field are shown below each panel in seconds.

Influence of E on complexing and decomplexing. We have also investigated the lifetimes of the stationary complexes formed when MG/BPB and MB/BB are collisionally reacted at different E (see FIG. 7G and FIG. 7H, respectively). As E is increased from 3.1 to 9.4 V/cm, the total lifetimes of both complexes formed decrease (FIG. 5A and FIG. 5C). For both MG/BPB and MB/BB collisions, rescaling the time axis in the space-time plots by the ratio of the field strengths leads to a universal appearance for each pair (FIG. 5A and FIG. 5C, respectively). The green intensity channel, $I_{green}$, can be used to characterize the degree of optical absorption of attractive complexes of both pairs of dyes present in the stationary product bands, so we extract $I_{green}$ at the position associated with the product bands, d=0 mm, in the space-time plots (FIGS. 5B and 5D, see Methods). The post-collision long-time behavior of $I_{green}(t)$ for MG/BPB can be well described using a semi-empirical Fermi-like function that rises to a plateau (FIG. 5B, Table 2), yielding a decreasing time constant $\tau_c(E)$ associated with the spread of this Fermi-like function (FIG. 5B-inset). In contrast, the entire $I_{green}(t)$ for MB/BB is reasonably captured by a modified log-normal function that describes the optical absorption of the stationary band (FIG. 5D, Table 3). While the shape of the log-normal is effectively independent of E (see σ in Table 3), the time constant $\tau_d$ most closely associated with decomplexing decreases with E but overall has a much higher magnitude (FIG. 5D-inset) than $\tau_c$; thus, MB/BB complexes are much more persistent than MG/BPB complexes.

Figure 6A:
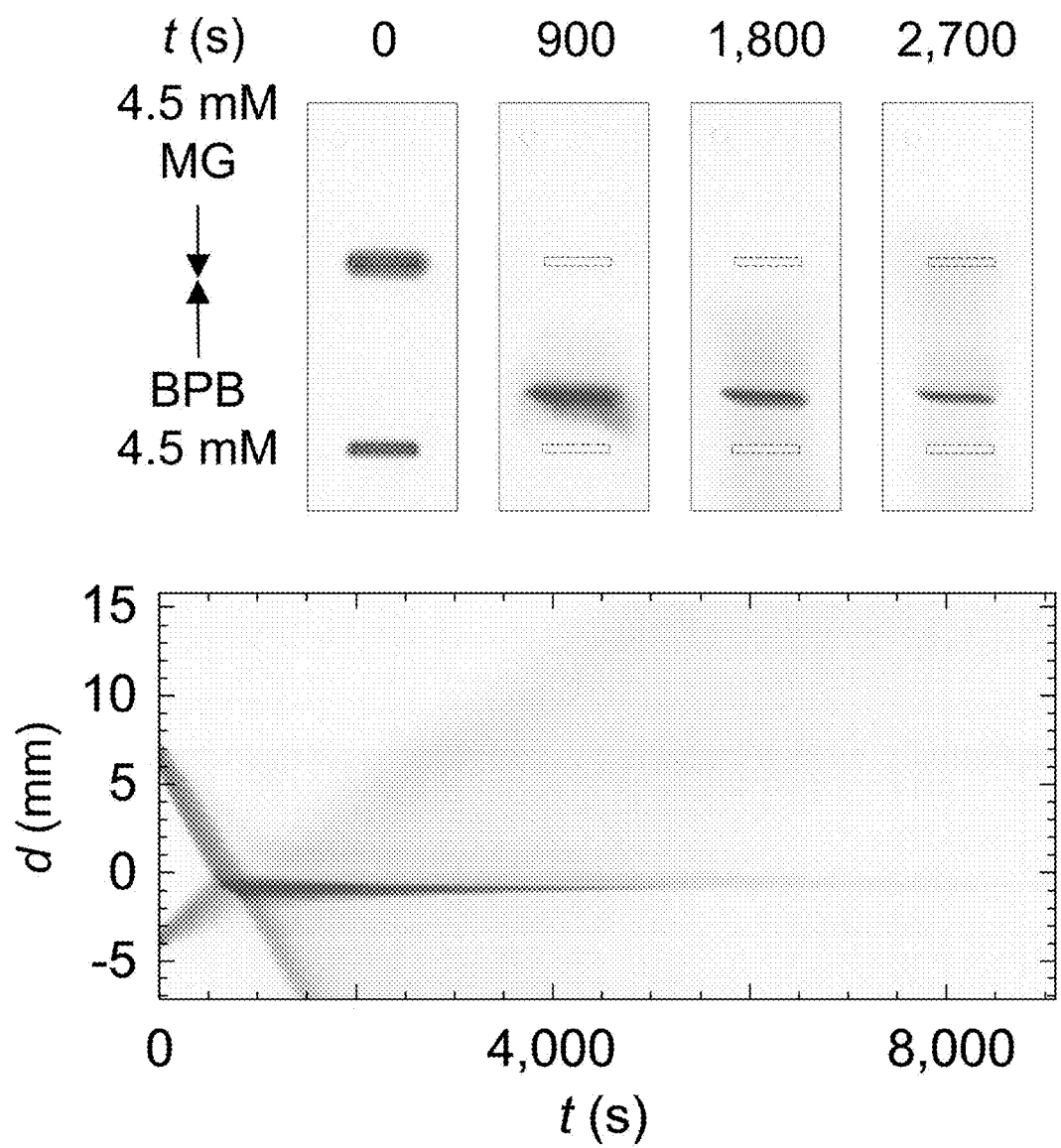
FIG. 6A shows overhead lane images at different times t after applying the electric field (upper) of protonated BPB (-1e) colliding with MG(+2e) in aqueous acidic 5.0 mM CAA buffer at pH=2.87 and E=3.1 V/cm using BCGE. Unless otherwise stated, 4 µL of each reagent is added fluidically to a well. Loaded reagent concentrations are specified at initial conditions. Scale: wells are indicated by dashed-line rectangles of 4.0×0.5 mm. A space-time plot (lower) reveals the formation of a non-propagating complex at the point of collision as a horizontal streak.
Figure 7I:
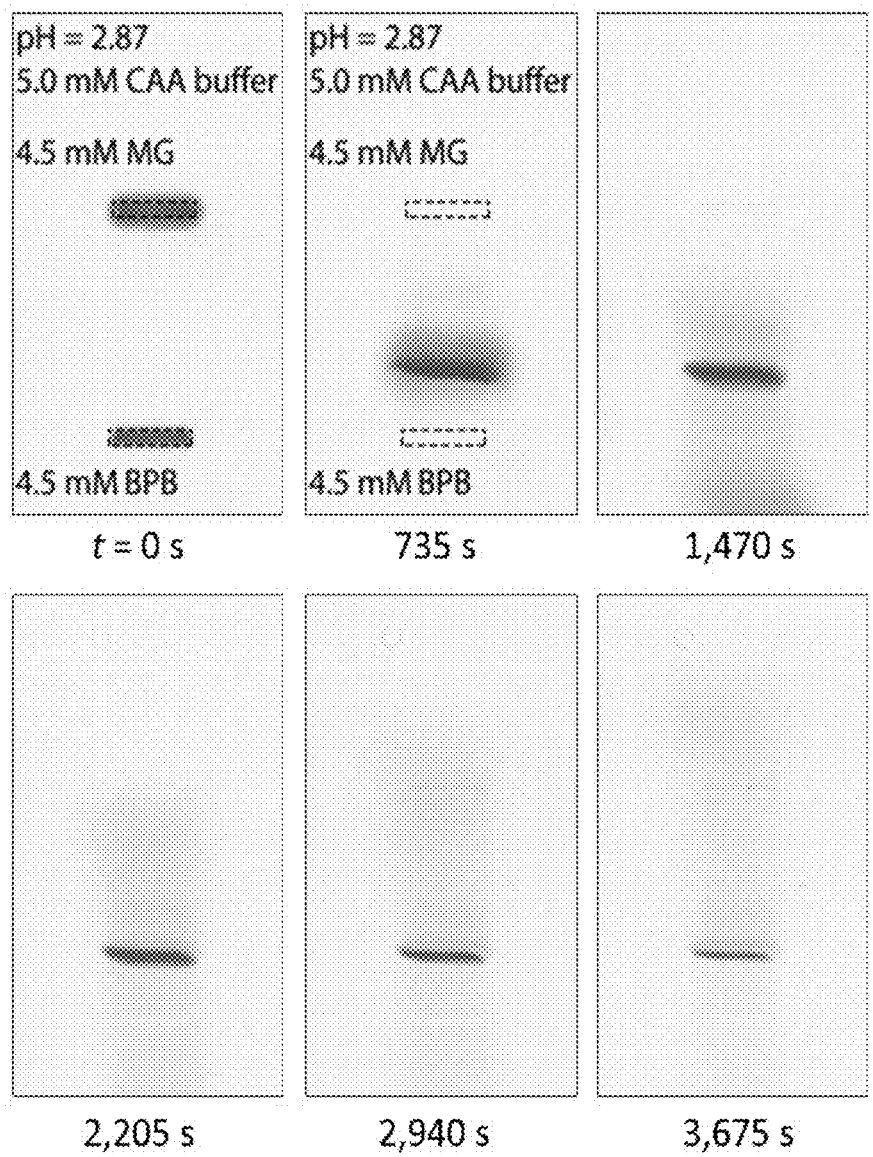
FIG. 7I shows BCGE of singly protonated BPB(−1e) and MG(+2e) in acidic buffer. BPB(−2e, blue) is singly protonated to BPB(−1e, yellow) in 5 mM chloro-acetic acid (CAA) buffer at pH=2.87, while MG remains in a +2e charge state. Collision yields a stationary band of complex that only slowly decomplexes/dissolves. Conditions: 3% (w/w) agarose, $|E|=3.1$ V/cm. Times after turning on the electric field are shown below each panel in seconds.

Band collision gel electrophoresis in acidic buffer. Although we typically use basic SBB at pH=9.0, BCGE can also be performed in neutral and acidic buffers. As an example, we use a 5 mM chloro-acetic acid (CAA) buffer at pH=2.87, well below the first $pK_a$ of BPB, so singly protonated BPB(−1e) in CAA buffer appears yellow, not blue, yet remains negatively charged. BCGE of BPB(−1e) with MG(+2e) at this pH still results in complex formation (FIG. 6A, FIG. 7I), yet the complex's stoichiometric ratio in acidic CAA differs from that in basic SBB.

Figure 6B:
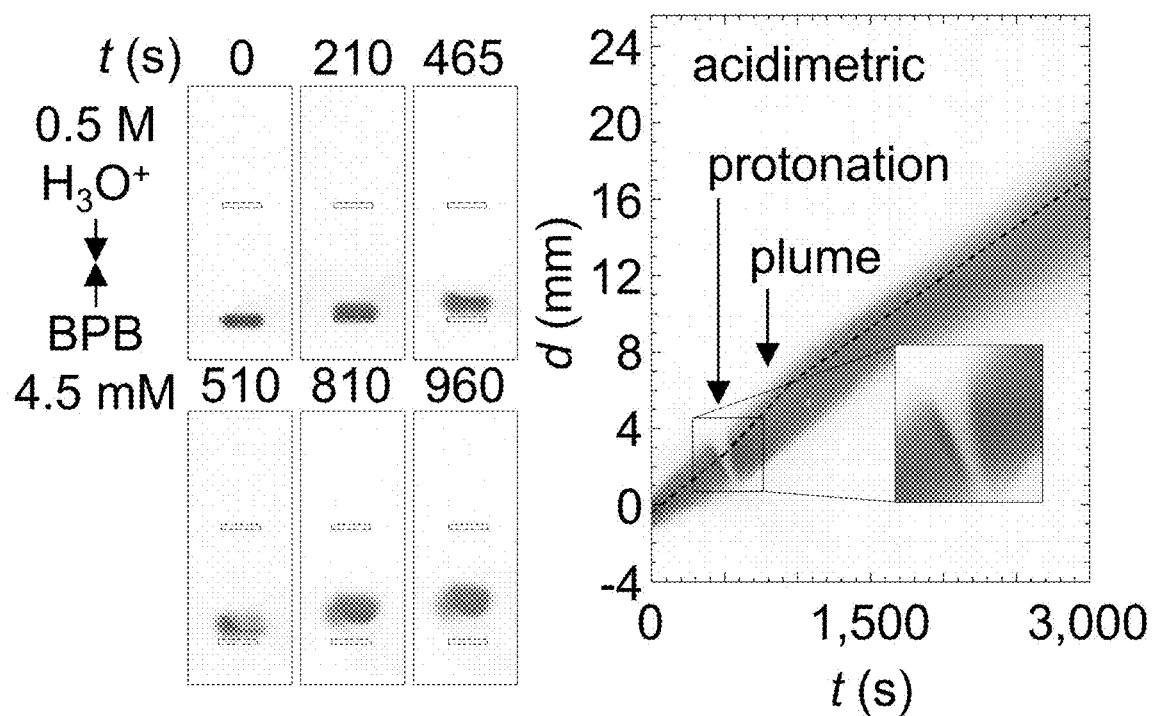
FIG. 6B shows acidimetric band collisions between counter-propagating acid indicator dye BPB(-2e) and hydronium ions $H_3O^+$ using BCGE. Overhead lane images (left) and space-time plot (right) revealing protonation of the leading edge of the band of BPB (yellow) and subsequent ejection of a de-protonated BPB plume (purple). Buffer type and conditions: same as in FIG. 2A.
Figure 6C:
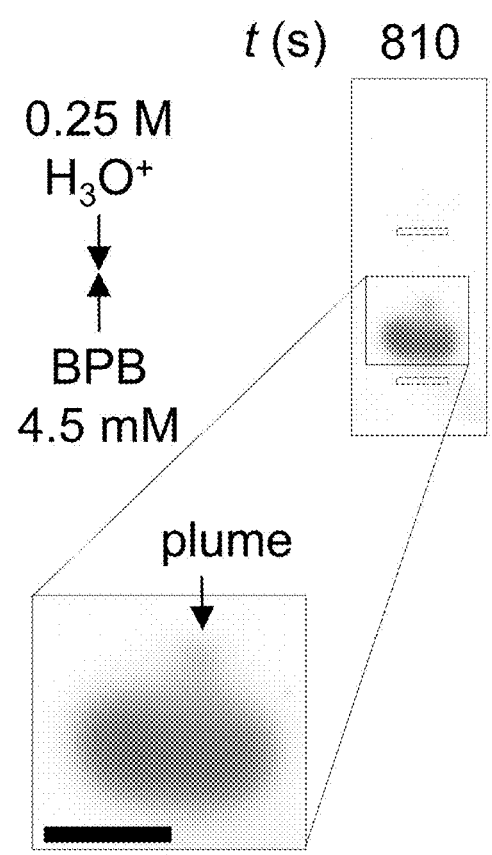
FIG. 6C shows an overhead lane image of BPB colliding with $H_3O^+$ using BCGE, as in FIG. 6B, indicating less protonation of BPB, but more prominent plume ejection. Scale bar in magnified detail: 2 mm.
Figure 7J:
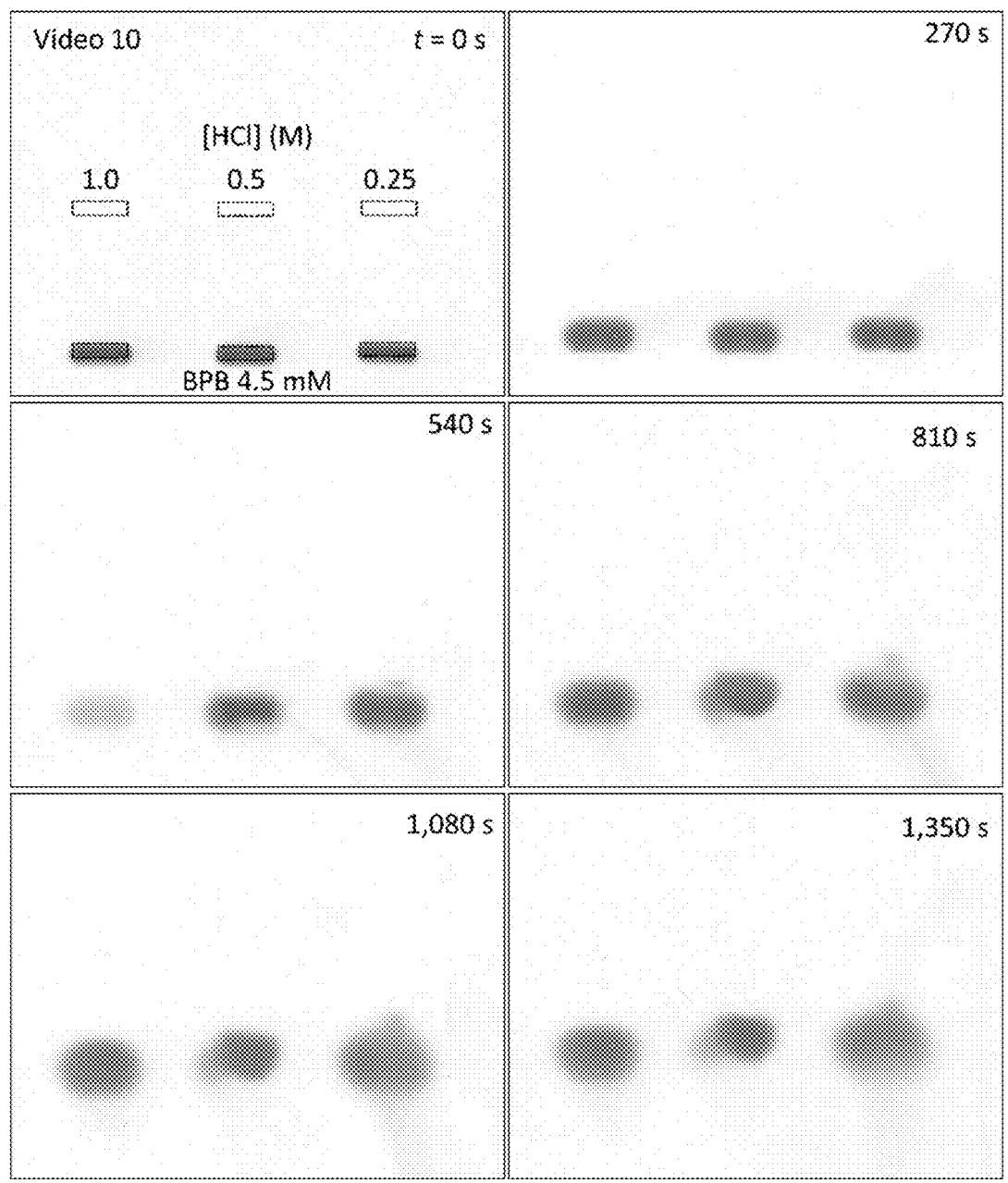
FIG. 7J shows BCGE of BPB(−2e) and $H_3O^+$: transient protonation and ejected plumes. Bands of BPB change color from blue to yellow and back to blue after colliding with invisible counter-propagating bands of $H_3O^+$ at 1.0, 0.5, and 0.25 M initial concentrations. A more rapidly-propagating plume of BPB is ejected from the leading edges of the bands (FIGS. 6B and 6C). Conditions: same as in FIG. 7B. Times after turning on the electric field are shown in the upper right in each panel in seconds.

Acidimetric reaction of indicator dye with hydronium ions. Collision of an acidic pulse with a band of dye molecules, each of which has at least one site suitable for protonation, can still be performed even in a low-concentration basic buffer. We collide an invisible pulse of $H_3O^+$ with a 4.5 mM counter-propagating band of BPB, which serves as a pH-dependent color indicator dye, at two different high $H_3O^+$ concentrations, 0.5 and 0.25 M (FIGS. 6B and 6C, respectively). These concentrated acidic pulses temporarily overcome the 5.0 mM SBB locally, but the $H_3O^+$ gradually becomes neutralized since the surrounding buffer has much greater volume, so these acid pulses become weaker over time. Upon collision, initially only the leading edge of the BPB band becomes singly protonated, revealing its yellow form (inset—FIG. 6B). Following this, a narrow faster-propagating plume of blue BPB is ejected, strikingly, in front of the rest of the band immediately after the protonated BPB returns to a deprotonated state (inset—FIG. 6C). A space-time plot of the collision between 0.5 M $H_3O^+$ and 4.5 mM BPB (see FIG. 7J—middle lane) reveals several stages associated with different BPB propagation velocities (FIG. 6B). At the onset of collision, protonation, and the appearance of a yellow color, the BPB band slows. However, the rest of the band behind the yellow front continues to propagate, leading to a local build-up in concentration of protonated and deprotonated BPB. When the leading edge deprotonates because of buffer neutralization, the local charge density along this leading edge has become much higher, leading to an instability that propels the plume of BPB forward at a higher speed and with some spatial focusing. Eventually, local ionic concentrations re-equilibrate to near their original values, and the original mobility of BPB returns.

Figure 6D:
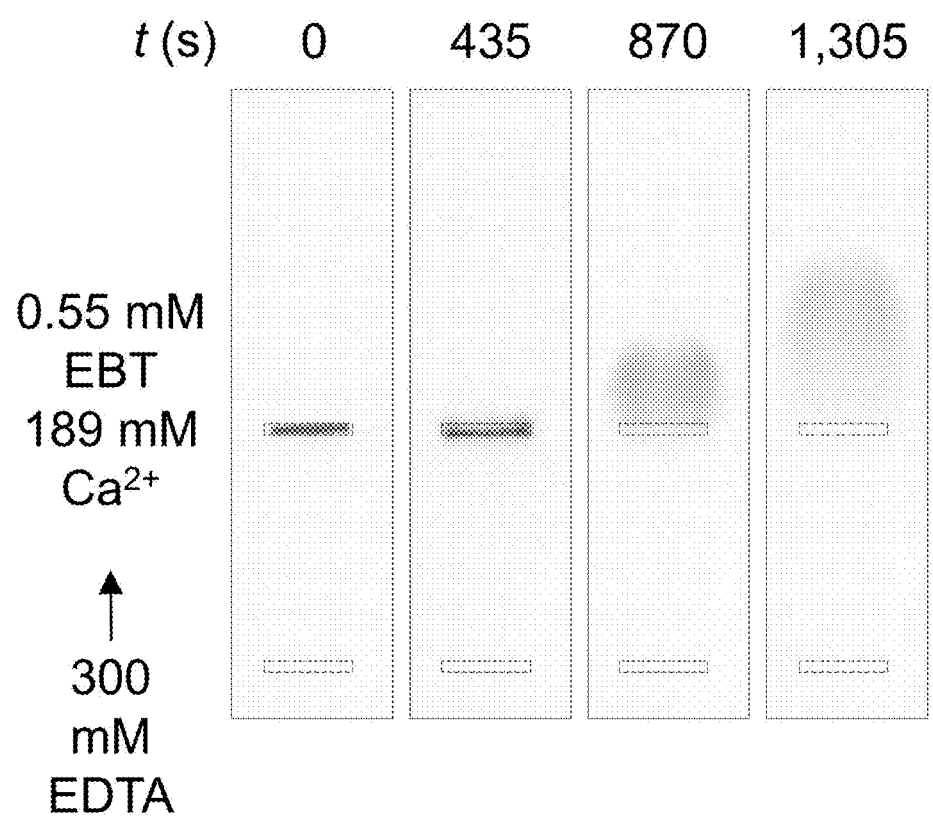
FIG. 6D shows the use of BCGE to create a complexometric ligand-exchange reaction in a gel configured with 2 wells in a single lane: overhead lane RGB color images of 2-well complexometric reaction at different observation times t after applying E. A neutral EBT/$Ca^{2+}$ complex is formed from EBT and $Ca^{2+}$ before $Ca^{2+}$ is exchanged during EDTA collision. Buffer type and conditions: same as in FIG. 2A.
Figure 6E:
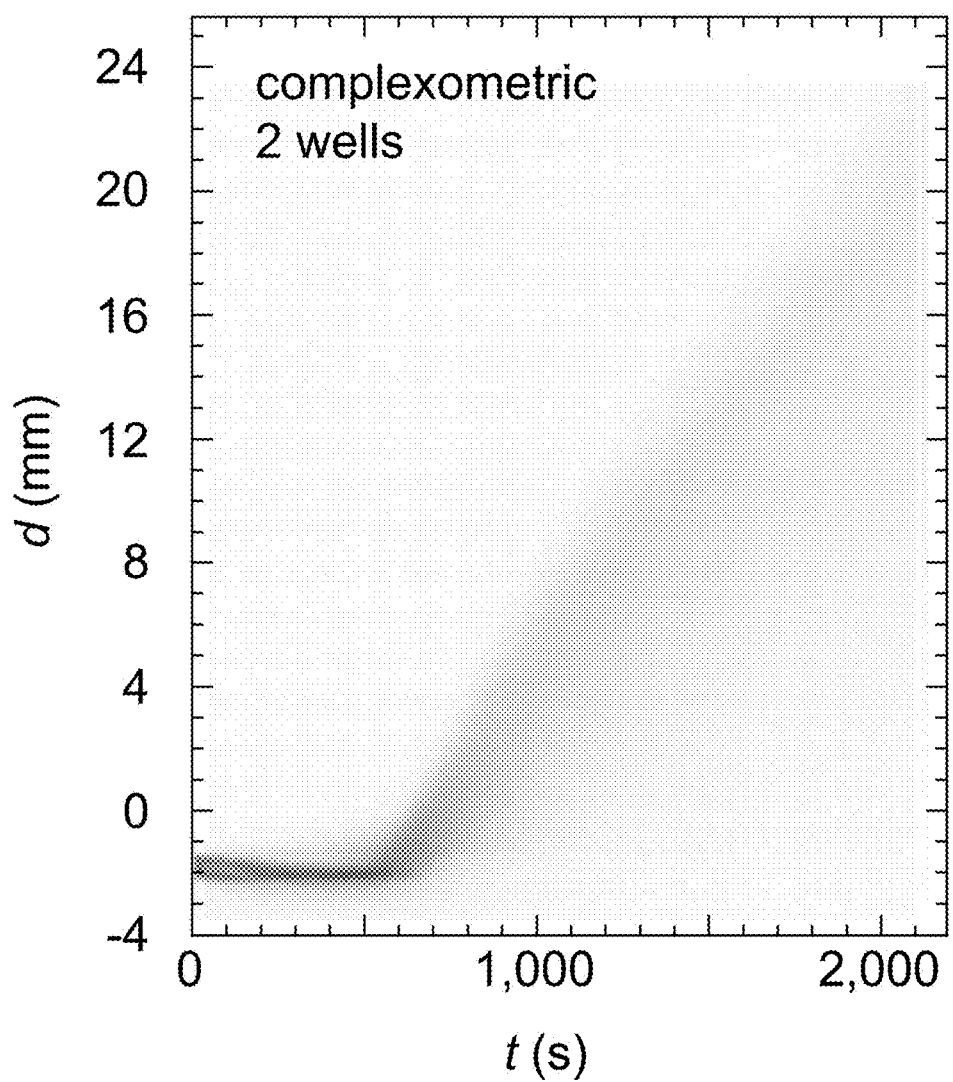
FIG. 6E shows a space-time plot of the complexometric ligand-exchange reaction in FIG. 6D, where the linear set of pixels is taken as a function of distance d along the center of the lane for different times t.

Complexometric ligand exchange reactions. A common indicator used for complexometric titrations is eriochrome black T (EBT), which dissociates in water yielding anions having −1e charge and a blue appearance[55]. However, when complexed with $Ca^{2+}$, EBT has a pink appearance[56]. We perform a BCGE experiment demonstrating displacement, in that the strong divalent-cation chelator ethylenediamine-tetraacetic acid[57] ($EDTA^{4-}$) can strip $Ca^{2+}$ from more weakly bound EBT-Ca complexes[58]. EDTA-Ca complexes will have net negative charge because of the excess negative charge in the $EDTA^{4-}$ compared to $Ca^{2+}$. The chelation capacity of EDTA is greatly reduced when one $Ca^{2+}$ is bound, so the likelihood of neutral EDTA-2Ca complexes being formed and remaining stable is extremely low. While we don't visualize the invisible EDTA-Ca complex, it would migrate as a negatively charged complex. We load 0.55 mM EBT with 189 mM $Ca^{2+}$ into one well (FIG. 6D—top well), and we load invisible 300 mM EDTA into a second well in the same lane (FIG. 6D—lower well). Initially, the pinkish EBT-Ca complexes do not propagate and remain in the top well, yet EDTA propagates from the bottom well towards the top well, and it eventually collides with the EBT-Ca complexes, liberating blue $EBT^-$. The corresponding space-time plot (FIG. 6E) reveals the change in a stationary pink band of EBT-Ca complexes after EDTA collides with it, strips and chelates $Ca^{2+}$ to form an invisible EDTA-Ca complex, and thereby liberates $EBT^-$ which becomes a propagating blue band.

Figure 6F:
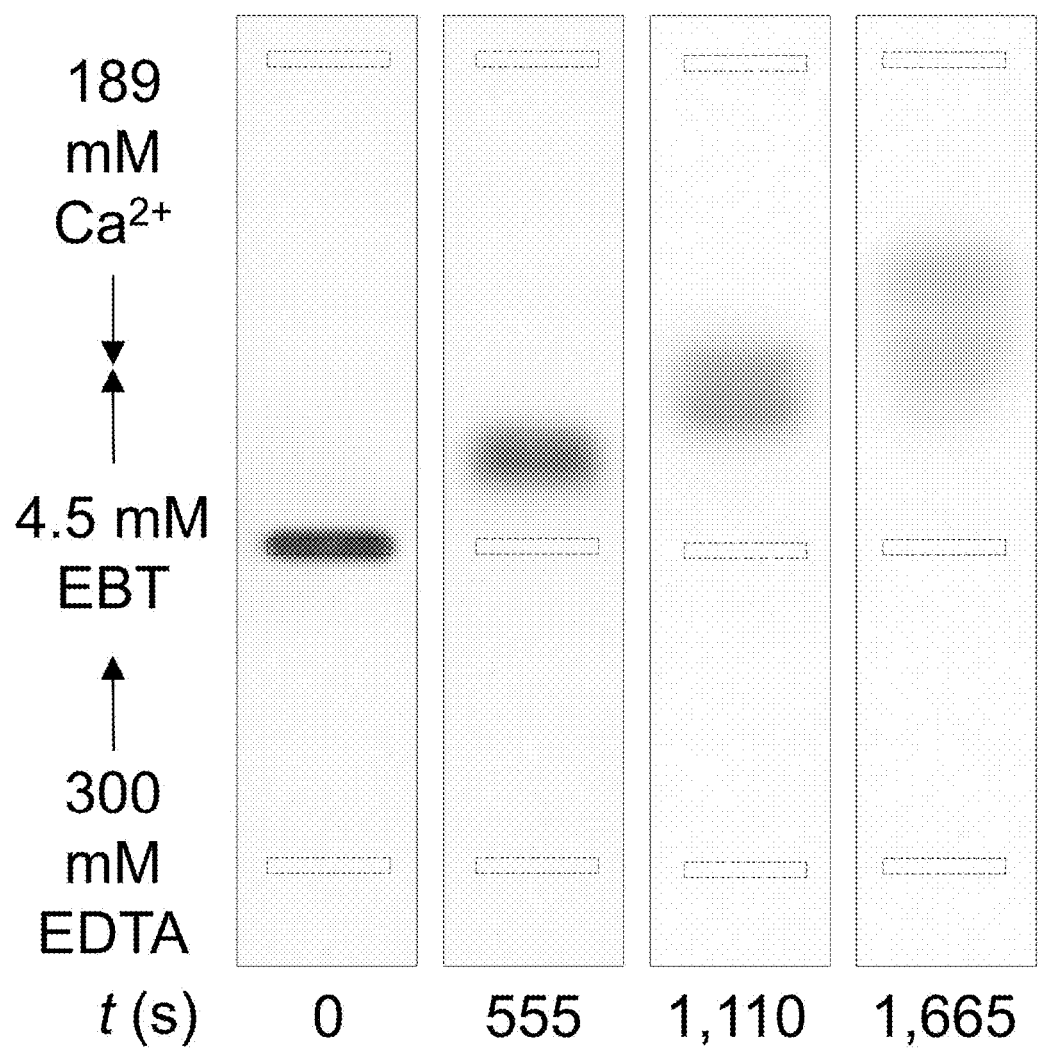
FIG. 6F shows BCGE overhead lane color images of 3-well complexometric reaction programmed to occur through a sequence of two collisional reactions in a gel configured with 3 wells in a single lane. First $Ca^{2+}$ collides with EBT forming the neutral complex, and then EDTA catches up and liberates the EBT. Buffer type and conditions: same as in FIG. 2A.
Figure 6G:
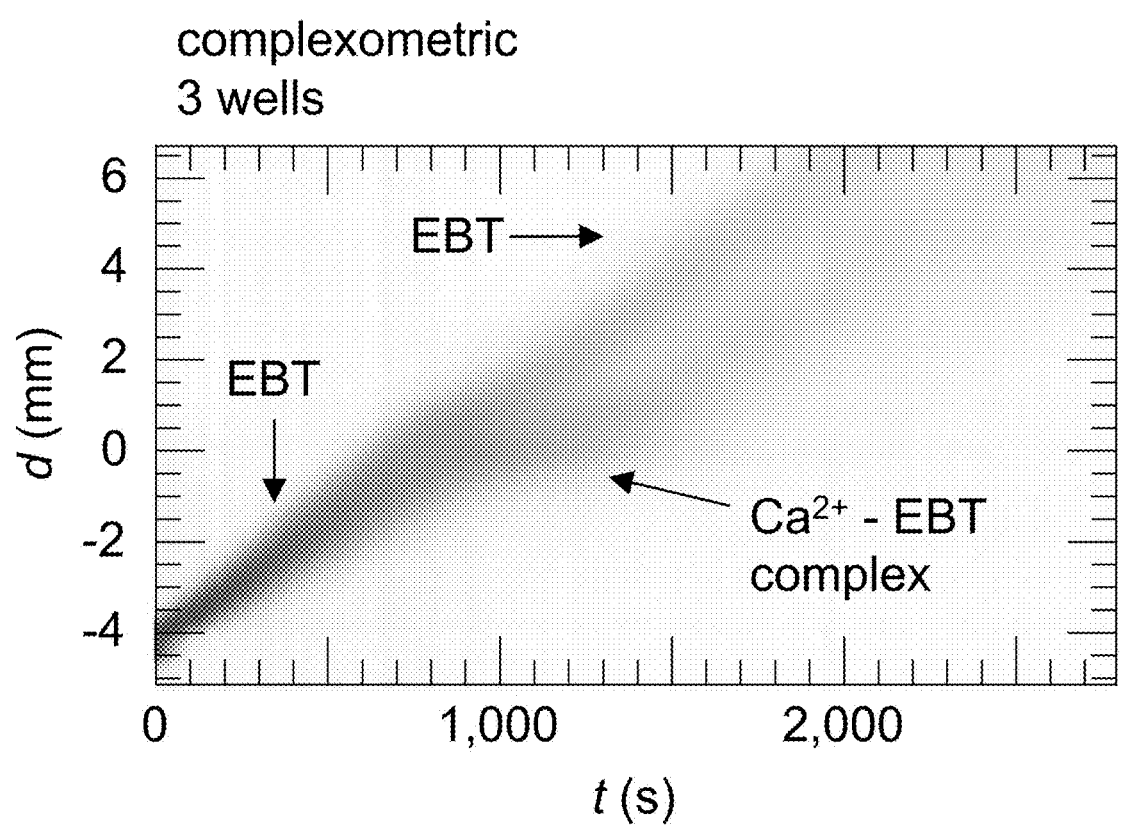
FIG. 6G shows a space-time plot of the complexometric ligand-exchange reaction in FIG. 6F, where the linear set of pixels is taken as a function of distance d along the center of the lane for different times t.

Programmed chemical reactions of colliding bands. To demonstrate the flexibility of BCGE for creating more complex sequences of reactions, a third well in the same lane creates a sequential reaction (FIG. 6F). A band of invisible $Ca^{2+}$ collides with a band of blue $EBT^-$, yielding some pink EBT-Ca complexes, and then invisible EDTA collides with this EBT-Ca complex, thereby stripping off and chelating the $Ca^{2+}$, so EBT changes back to a blue color and resumes anionic propagation. Corresponding to this more complex reaction sequence using three wells, the space-time plot also has significantly greater complexity (FIG. 6G).

Figure 6H:
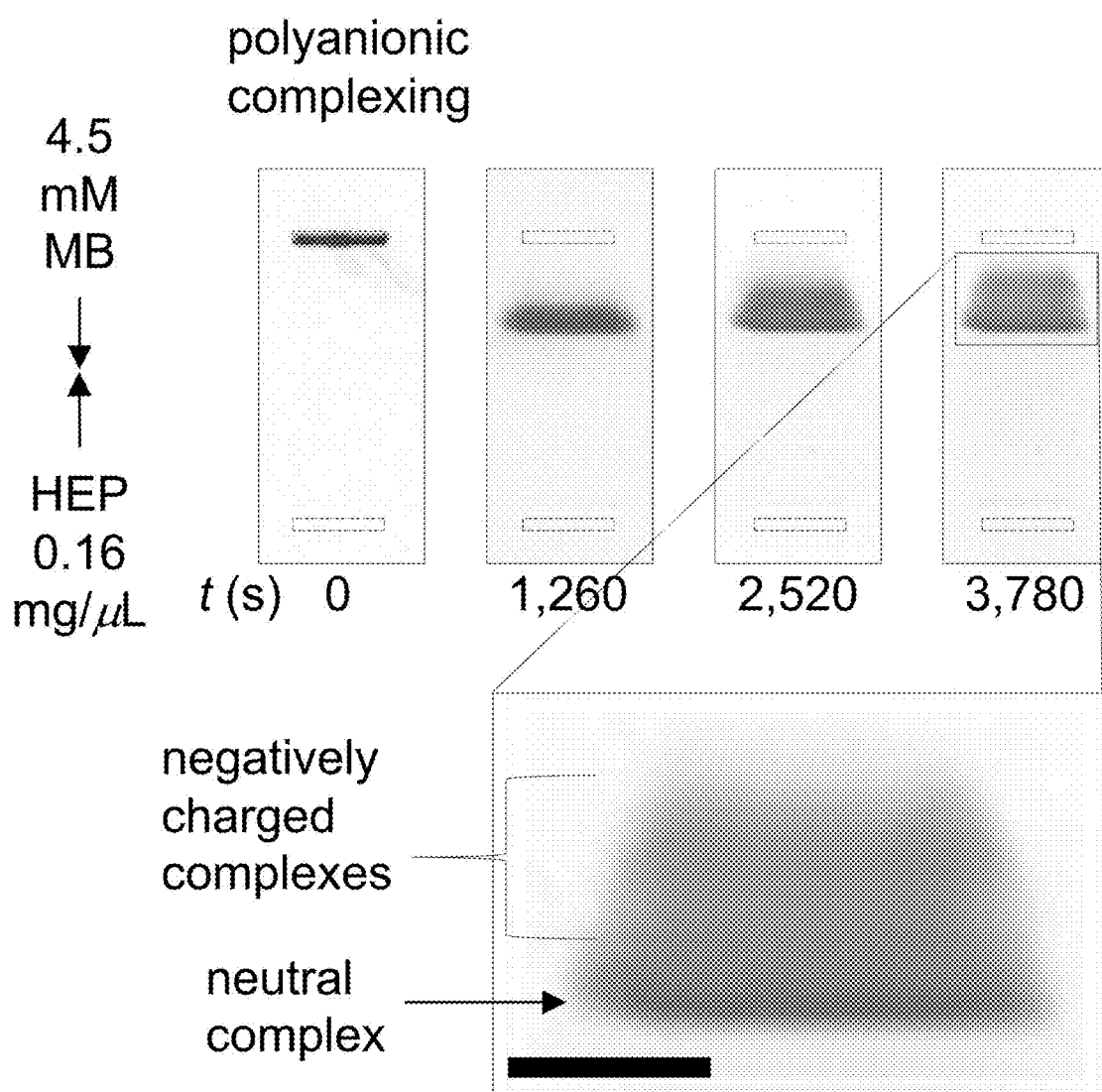
FIG. 6H shows overhead lane images using BCGE of a heparin (HEP) and MB collision resulting in both neutral complexes and partially negatively charged complexes, revealing spectral differences between these. This reaction produces a plurality of reaction-products resulting from the electrophoretic collision. Buffer type and conditions: same as in FIG. 2A. Black scale bar in magnified inset: 2 mm.
Figure 6I:
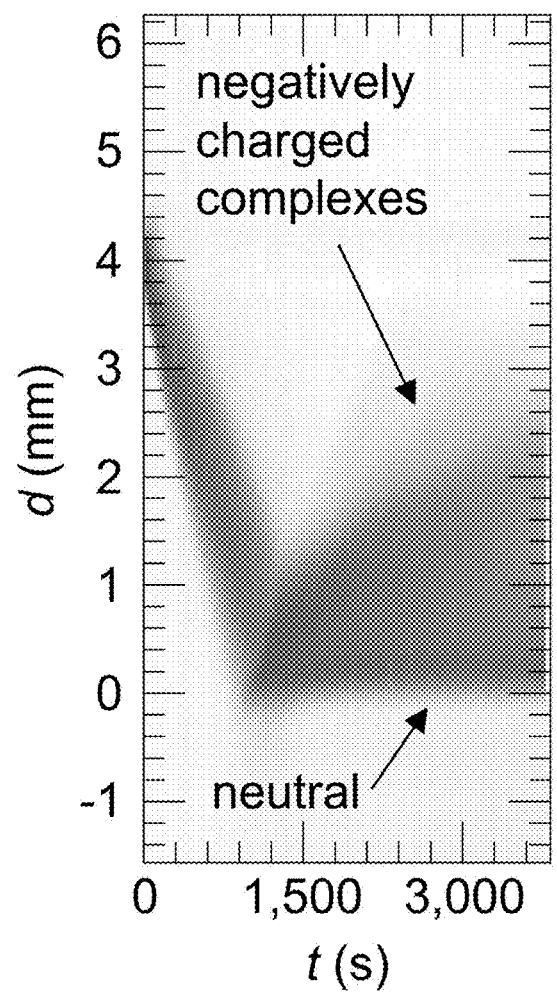
FIG. 6I shows a space-time plot of the HEP/MB complexing reaction in FIG. 6H generated using BCGE.
Figure 6J:
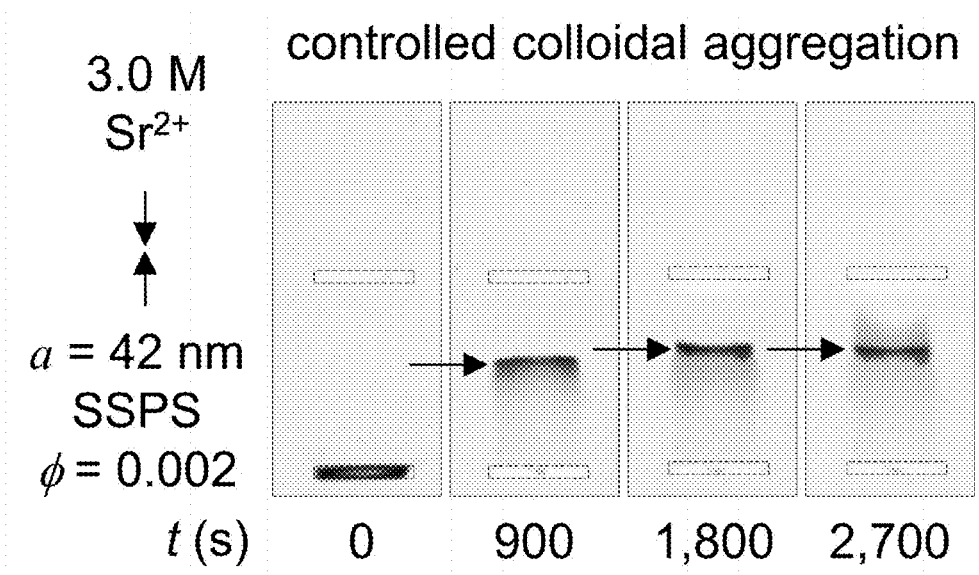
FIG. 6J shows overhead lane images at different observation times t of a controlled colloidal aggregation collision between $Sr^{2+}$ cations and sulfate stabilized polystyrene nanospheres (aggregates indicated by arrow). Buffer type and conditions: same as in FIG. 2A.
Figure 6K:
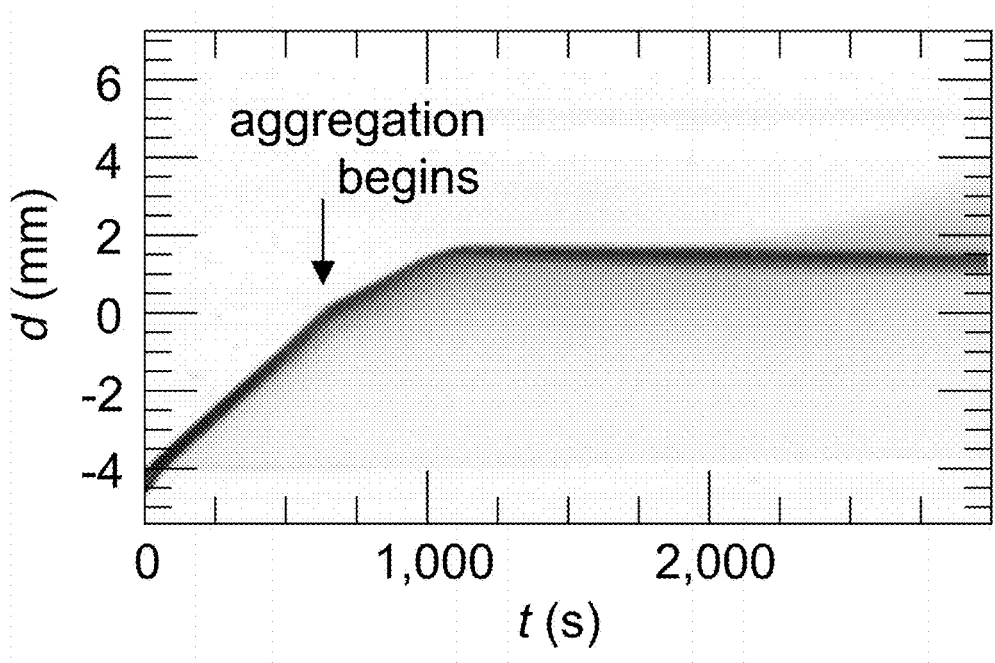
FIG. 6K shows a space-time plot of controlled colloidal aggregation reaction in FIG. 6J made using BCGE.
Figure 6L:
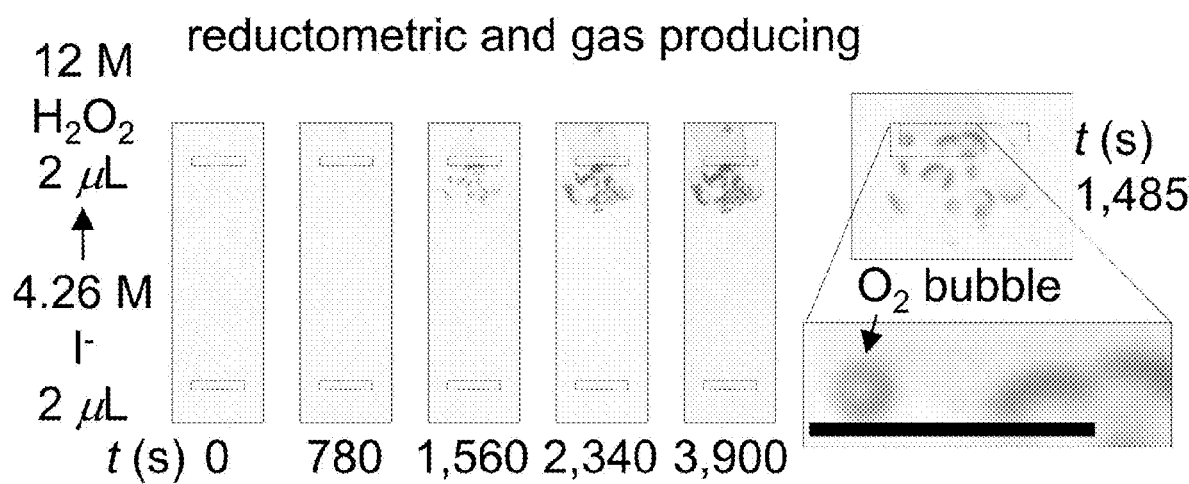
FIG. 6L shows a redox reaction producing 02 gas bubbles resulting from a collision of a band of propagating $I^-$ anions with a band of stationary neutral $H_2O_2$ molecules using BCGE. Buffer type and conditions: same as in FIG. 2A. Black scale bar in magnified inset: 2 mm.
Figure 7K:
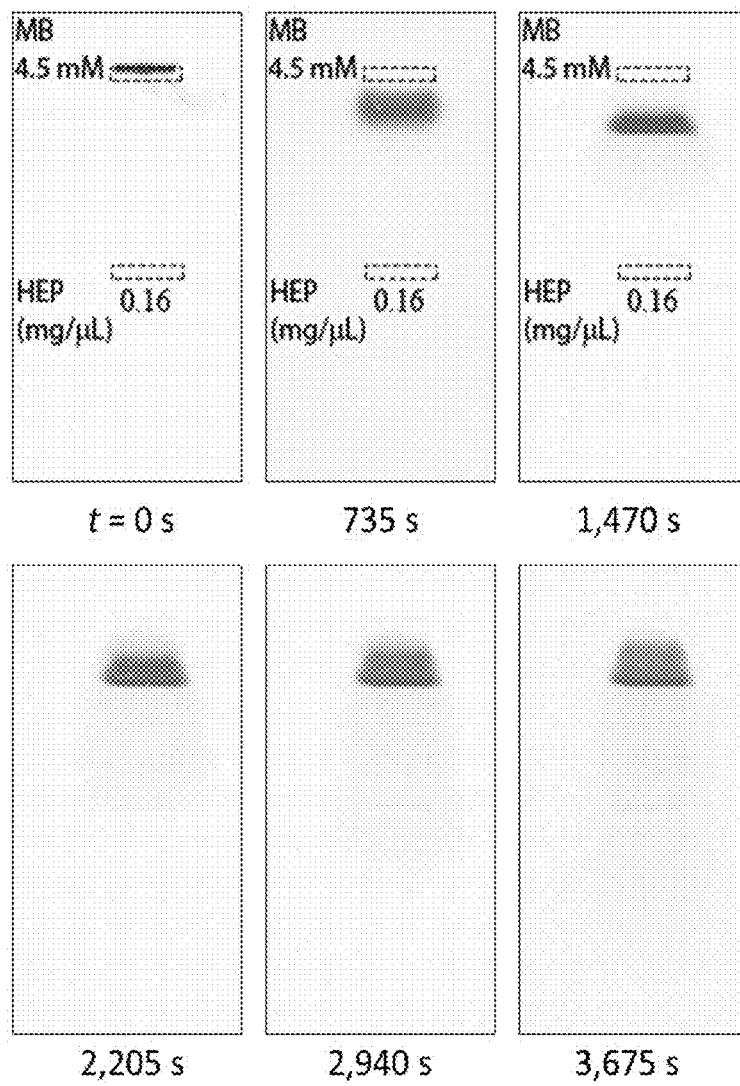
FIG. 7K shows BCGE of invisible poly-anionic heparin (HEP) and MB(+1e). Complexes having different stoichiometry and propagation rates are formed; the degree of HEP:MB complexing is indicated by a change from blue to purple color. Levels have been adjusted to provide increased visibility of decomplexing MB propagating downwards. Conditions: same as in FIG. 7B. Times after turning on the electric field are shown below each panel in seconds.
Figure 7L:
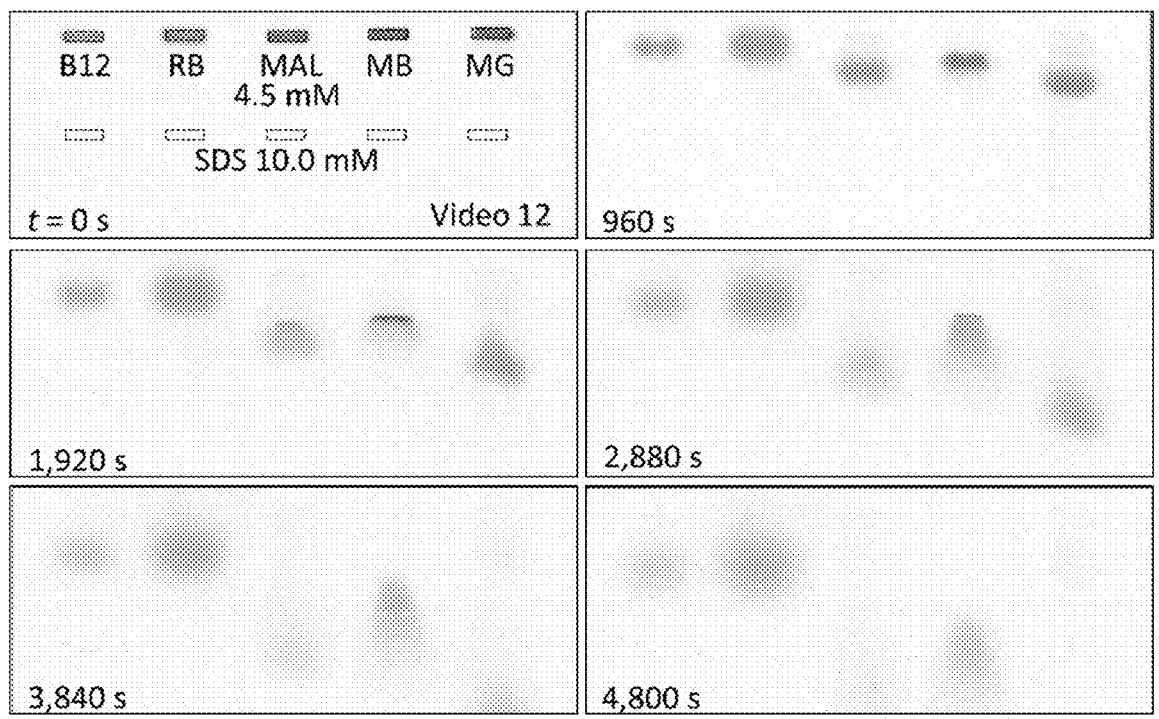
FIG. 7L shows BCGE of invisible surfactant $DS^-$ and dyes B12, RB, MAL, MB, and MG. Bands of DS anions pass through bands of neutral B12 and RB with no observable interaction, whereas DS forms complexes having different longevities with cationic MAL, MB, and MG. Conditions: same as in FIG. 7B. Times after turning on the electric field are shown in the lower left in each panel in seconds.
Figure 7M:
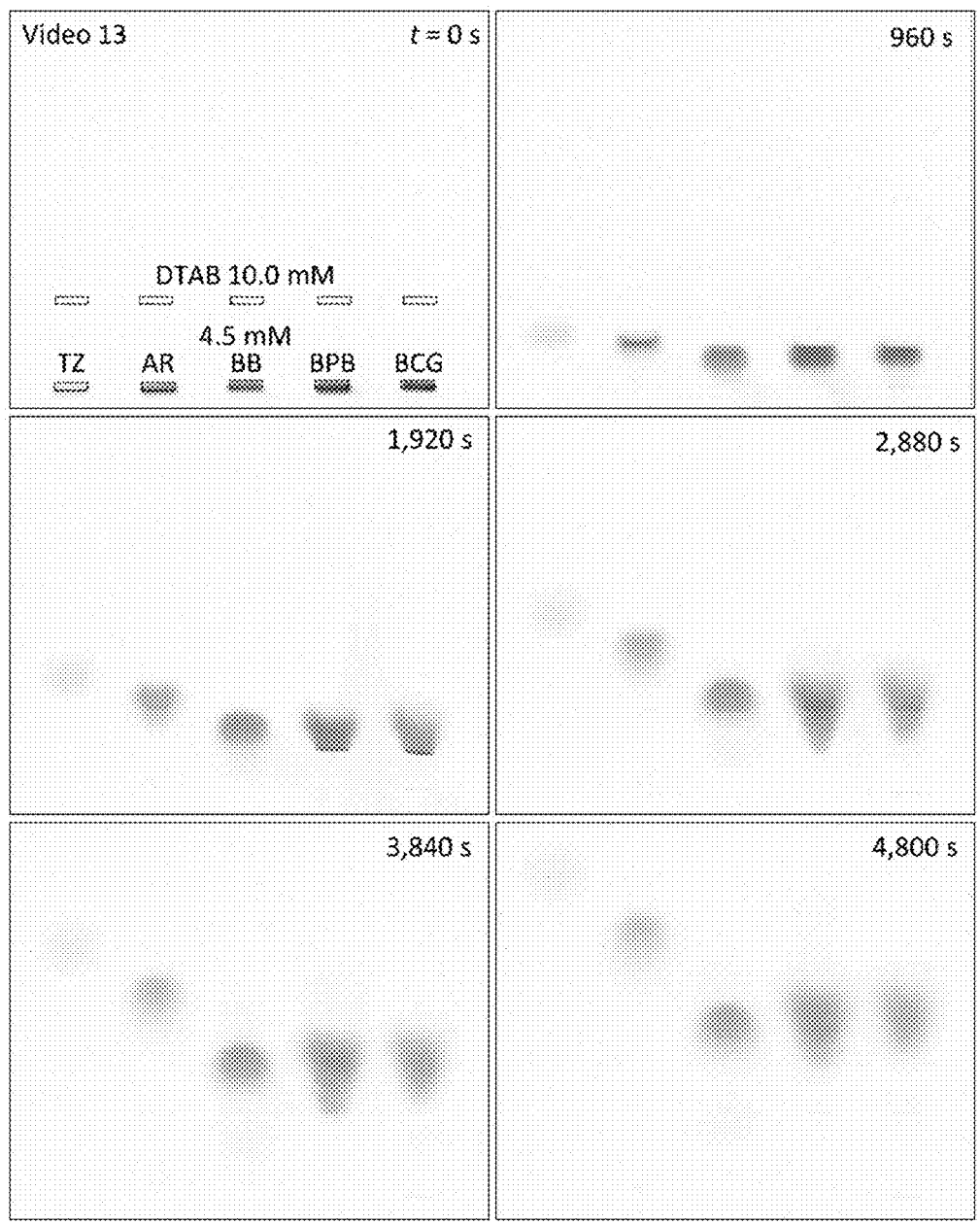
FIG. 7M shows BCGE of invisible surfactant $DTA^+$ and anionic dyes TZ, AR, BB, BPB, and BCG. Complexes of $DTA^+$ with these anionic dyes form upon collision, yielding stationary bands that can be seen most easily for AR, BPB, and BCG. Conditions: same as in FIG. 7B. Times after turning on the electric field are shown in the upper right in each panel in seconds.

Additional demonstrations of the broad utility of BCGE. We have changed the charge state of poly-ionic biopolymers, irreversibly aggregated nanospheres to halt their propagation in the gel, created gas bubbles through a redox reaction, and collided invisible bands of anionic and cationic surfactants with visible bands of oppositely charged dyes. We collide a slower-moving band of invisible poly-anionic heparin[59] (HEP) with a faster-moving band of blue MB(+e) to form purple $HEP-(MB)_x$ complexes[60] (FIG. 6H). Some HEP molecules are fully neutralized by MB and stop propagating, yielding a purple stationary band, whereas other HEP molecules are only partially neutralized to different degrees and continue propagating to form a purple-blue smear (FIG. 6I, FIG. 7K). We have also used sulfate-stabilized polystyrene (SSPS) nanospheres as reagents in a passivated gel form of BCGE; the non-ionic passivation agent PEG-1000 has been added to allow polystyrene spheres to propagate in a large-pore agarose gel[45,61] (see Methods). Sulfate groups on a sphere becomes irreversibly bound to sulfate groups on other spheres, mediated by $Sr^{2+}$ cations[62], leaving behind a narrow stationary band of nanosphere aggregates larger than the gel's pore size (FIG. 6J—arrows and FIG. 6K—dark horizontal line). In addition, we show that a redox reaction[63] of a propagating band of iodide $I^-$ (2 µL of 4.26 M loaded) with a stationary band of neutral hydrogen peroxide $H_2O_2$ (2 µL of 12 M loaded) results in the formation of $O_2$ gas liberated as visible bubbles in the $H_2O_2$ well-region (FIG. 6L) according to the reaction, $H_2O_2(aq)+I^-(aq)\rightarrow H_2O(l)+IO^-(aq)$ (slow) followed by oxygen production $H_2O_2(aq)+IO^-(aq)\rightarrow H_2O(l)+O_2(g)+I^-(aq)$ (fast). Some bubbles become trapped within the gel. Although one reagent is charge-neutral, the other is not, so the relative difference in propagation velocities still enables these bands to be collided and reacted. If the reaction product is visible, then simple optical imaging can still be used to detect and quantify the extent of the reaction, even if both bands of reagents are invisible. If two invisible bands propagate and collide to produce a visible product, then optical BCGE can be used to directly measure $\mu_e$ of the reagent species through the location of and elapsed time until collision. As additional examples, we have created stationary complexes by colliding invisible anionic surfactant dodecyl sulfate $DS^-$ with cationic dyes MAL, MB, and MG (FIG. 7L) and by colliding invisible cationic surfactant dodecyl trimethylammonium $DTA^+$ with anionic dyes TZ, AR, BB, BPB, and BCG (FIG. 7M).

Discussion

Optical BCGE provides detailed movies of spatiotemporal pattern formation associated with collisional reactions of solvated and propagating reagent species in spatially localized bands within gels. Highly mobile reactant, complex, or product species can be contained in inert environments, thereby extending observation periods where fast kinetics could otherwise not be studied. Similar to gas-phase investigations utilizing matrix-isolation methods[64,65], BCGE is well-suited for studying both reversible and irreversible reactions involving only small quantities of reagents, and product species can typically be separated and isolated from unreacted reagents in situ. Moreover, complex sequences of reactions of bands can be effectively programmed by designing the locations of multiple wells in the same lane, similar to the programmability of flow-driven microfluidic channel systems. Thus, BCGE offers significant advantages over single-well non-collisional EMSA when performing GE on interacting species.

Predicting the often striking, yet complex, evolving spatio-temporal patterns created by BCGE represents an interesting challenge for theoretical modeling and simulation. Such predictive modeling would need to incorporate and appropriately couple many different physical and chemical effects, over and above the electrophoretic propagation of species in an electrolyte-buffer at a certain pH within a porous gel. These effects include forward and reverse reaction rates, effective collisional cross-sections of reagent species, Brownian diffusion of propagating molecular and colloidal species, reaction stoichiometry, diversity of product species, potential growth of products produced as aggregates or precipitates relative to the gel's pore size, electric field strength, pH- and ligand-dependent conformations, and spectroscopic properties of molecules. Theoretical advances could lead to predictions of space-time plots complete with full spectroscopic detail, which could be quantitatively compared with BCGE measurements. Nevertheless, the complex inverse problem of solving for fundamental intermolecular interaction parameters as well as types and structures of product species from the evolving patterns of BCGE is likely at least in some cases to be ill-posed mathematically, and a unique solution to this inverse problem is not guaranteed. Despite this, it is also likely, at least initially for certain simpler reagent and product species, that it will be possible to model the spatiotemporal patterns in BCGE and thereby extract useful molecular-scale interaction parameters from measurements. Greater degrees of complexity could then be introduced into the reagent species, reaction types, and modeling, further extending the range of quantitative interpretation of BCGE.

We anticipate that many interesting experimental applications and extensions of BCGE lie ahead (see Supplementary Discussion). For instance, BCGE is not inherently limited to a visible color array detector; it could be extended to wavelengths beyond the visible spectrum. Using fluorophore-labels, quantum dots, photonic nanoparticles, or other absorbing stains in combination with, for instance, ultraviolet illumination and visible detection wavelengths could reveal certain propagating bands that would otherwise be invisible. Using a variety of different optical configurations, modalities, and wavelengths, rather than just visible absorption in a transmission geometry, we anticipate that BCGE can be extended to visualize interactions between biomacromolecules, including proteins and poly-nucleic acids. Spatially resolved spectroscopies could be used to measure concentrations of reactants, products, and long-lived intermediates more precisely. Also, BCGE can be readily generalized to pH-neutral and acidic buffers. Moreover, we anticipate that 2D and 3D versions of BCGE will provide access to even higher levels of complex programmable reactive combinatorial chemistry coupled to electrophoretic separations.

Methods

Gel and dye preparation. All gels are prepared using Sigma-Aldrich Type I-A, low EEO agarose at 3.0% w/w in distilled water (conductivity measured to be <0.5 µS/cm)[45]. Using this agarose concentration corresponds to characteristic pore sizes of the gel of ≈50 nm, since nanospheres having diameters smaller than ≈50 nm will propagate through the gel[61]. This higher gel concentration also reduces diffusion of dye molecules, lowering dispersion (i.e. width of bands). When making dye solutions, we follow common GE protocols by adding $D_2O$, which has a higher mass density than $H_2O$ and therefore causes the solution containing the dye molecules to sink to the bottom of the wells prior to turning on the electric field. This provides better uniformity in the vertical location of the loaded dyes in the wells prior to migration and collision. Dyes (see Table 1 for manufacturer and purity) are dissolved in distilled water before diluting 1:1 with $D_2O$ (Cambridge Isotope Laboratories, Inc., 99% purity) to a final dye concentration of 4.5 mM unless otherwise indicated. High reagent concentrations greater than 1 M are sufficiently higher in density than the surrounding buffer and are not mixed with $D_2O$ before loading.

Gel electrophoresis. We use a transparent acrylic horizontal GE apparatus (see FIG. 1A) with Pt electrodes (American Scientific, LLC, item 8101-00); chamber dimensions are 152×76×44 mm and each gel slab is 70 mm wide, 100 mm long (i.e. along the electric field), and 3.5 mm thick. We make custom gel combs by laser cutting thin poly-tetrafluoroethylene (PTFE) sheets to create 4.0×0.5 mm wells that are 2.5 mm deep. We control distances between wells in the same lane using 2 or more combs when casting. The chamber is filled with buffer solution (typically 5.0 mM sodium borate buffer at pH=9.0) to a height of 2.5 cm above the gel surface. While we report electric field strengths to enable comparison with other GE experiments, we operate our power supply in constant current mode throughout all experiments to keep band velocities constant over longer durations[45]. All infusions of samples into wells are 4 µL in volume unless otherwise stated. Wells are loaded from left to right, top to bottom. To reduce initial diffusion of the dyes after loading into the wells in the porous gel, the power supply is activated as soon as all wells have been filled, so that no reagent has been in a well more than 30 s after loading before the electric field is applied.

Minimizing interactions with the porous gel matrix. The hydrodynamic radius of a typical organic dye molecule used in this investigation is significantly smaller than the characteristic pore size of the agarose gels used, such that interactions between such dye species and gel are largely negligible, particularly when compared to those that can occur between large biomacromolecules confined to the typically much smaller pores of polyacrylamide gels during EMSAs. Reagent dye molecules and small product complexes of these dyes are likely to experience only minimal gel-matrix effects on their transport properties in the large-pore agarose gels that we use. Reaction kinetics and propagation velocities of bands can depend on pore size if the sizes of reagents and/or products are not much smaller than the gel's characteristic pore size. We present aggregation reactions that demonstrate this limit, both with molecular and colloidal reagents, since the product aggregates exceed the pore size and subsequently do not propagate.

Image acquisition. All images are taken using a Nikon D5000 DSLR camera body equipped with a Nikon 70 mm-300 mm zoom lens set at ≈195 mm and rigidly mounted ≈1 m above the GE tank. Gels are illuminated from underneath the tank by a light box (CubeTech HL225 natural/white LED at 10,000 lux), yielding a transmission optical format. Exposure settings are ISO 200, f/10, and 1/60 s. Pixel saturation is avoided by reducing the exposure time, if needed. Single frames (4,288×2,848 pixels, RGB 24-bit color) are taken every 15 s unless otherwise indicated, yielding time-lapse movies. Color balance is calibrated using a 24 color card and standard procedures (Camera-Trax). Reference background images are taken immediately prior to loading any wells.

Background subtraction of images. To increase signal-to-noise, we subtract the corresponding reference background image (prior to loading) from each measured image in a sequence using the following procedure (ImageJ). After inverting the image from the sequence, an inverted background image is subtracted using image calculation, and the resulting background-subtracted image sequence is inverted again. This double inversion is appropriate for background-subtracting transmission images of absorbing dyes.

Extracting intensity profiles and making space-time plots. A single-pixel strip along the field direction (i.e. vertical) in the center of a lane is extracted from an image using MATLAB, and intensity values in each RGB channel are quantitatively determined. For a given lane, successive vertical pixel strips are extracted from an image sequence and concatenated horizontally, yielding a space-time plot that summarizes quantitative spatiotemporal evolution of band collisions and reactions.

Time and location of a band-collision. We consider BCGE involving two wells in the same lane (see FIG. 1B); the first is centered at position x=0 and the second is centered at x=L. Reagent species 1 and 2 have electrophoretic mobilities $\mu_{e,1}$ and $\mu_{e,2}$, respectively. These reagents are initially loaded into these wells in the absence of an electric field. Having prior knowledge of the values (or at least the predicted signs at a given pH) of $\mu_{e,1}$ and $\mu_{e,2}$ is typically desirable, since this is useful in choosing which reagent species to load into a specific well, given the direction of the electric field E, and also in selecting an appropriate value of L in order to generate a collision of propagating bands in the gel. However, if $\mu_{e,1}$ and $\mu_{e,2}$ are not known in advance, both combinations of loading can be performed in two different lanes (i.e. species 1 in a well at x=0 and species 2 in a well at x=L in a first lane, and vice-versa in a different lane); this will typically yield a collision of bands in only one of the two lanes. In what follows below, we assume that reagent species 1 is loaded into the well at x=0 and reagent species 2 is loaded into the well at x=L. The electric field E is turned on at time t=0, and the centers of the bands of reagent species 1 and 2 propagate to positions $x_1(t)=\mu_{e,1}$ and $x_2(t)=L+\mu_{e,2}Et$, respectively, at a time t. These equations assume that E is spatially homogeneous and remains constant over time. Solving these equations for the collision of the centers of the bands, which occurs when $x_1(t^*)=x_2(t^*)=x^*$, we determine the collision time $t^*=L/[(\mu_{e,1}-\mu_{e,2})E]$ and collision location $x=L[\mu_{e,1}/(\mu_{e,1}-\mu_{e,2})]$.

Figure 1C:
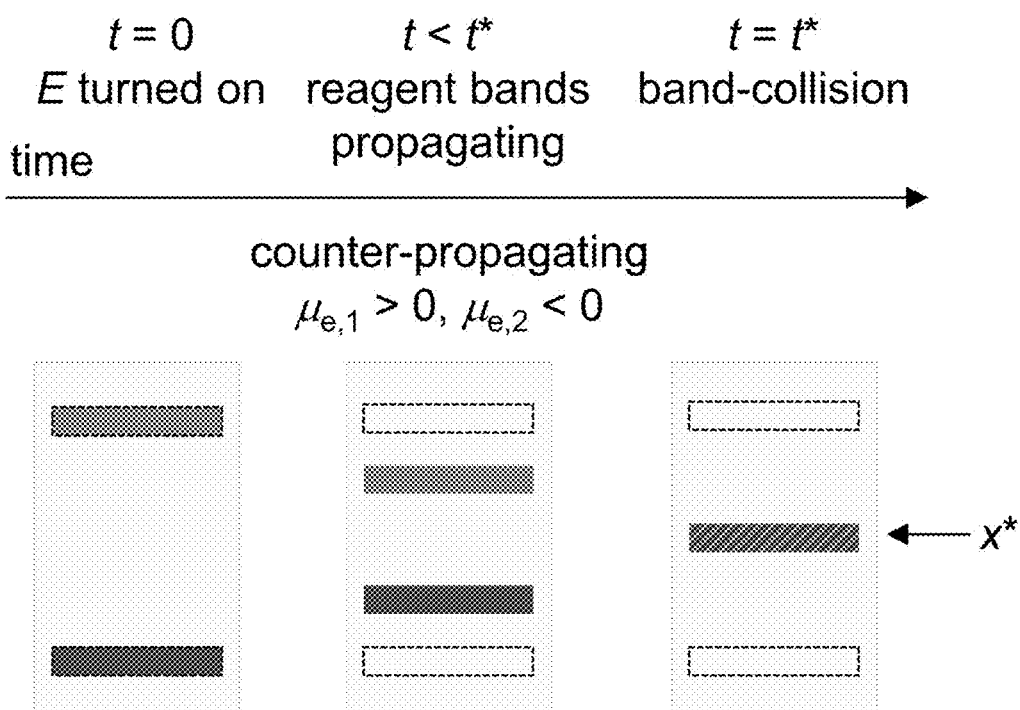
FIG. 1C shows counter-propagating BCGE for $\mu_{e,1}>0$ and $\mu_{e,2}<0$; so band-collision always occurs at x* between the wells. Each panel shows the evolution of bands in a single lane containing two wells: (left) at time t=0 where E is turned on, (middle) at some time later time t<t* before band-collision, and (right) full band-collision at time t=t*, yielding band-collision location x*.
Figure 1D:
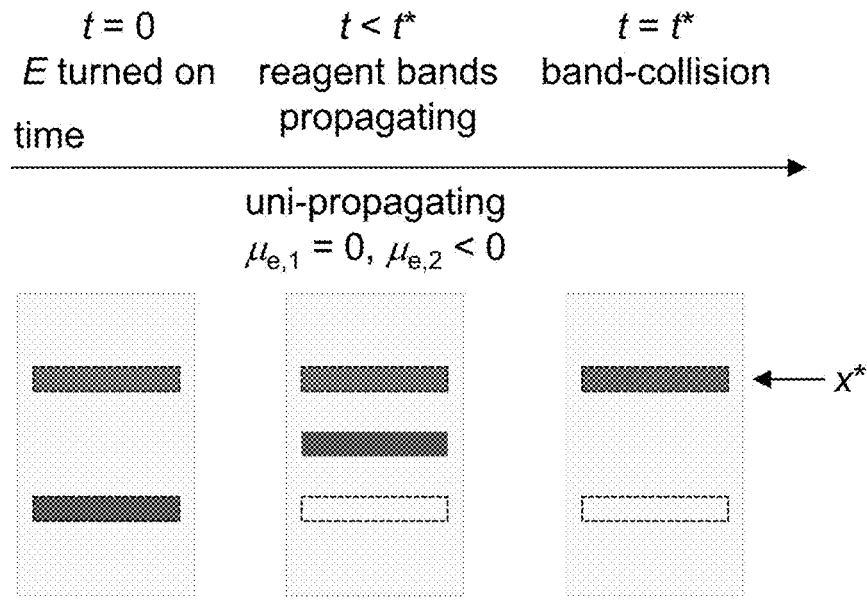
FIG. 1D shows uni-propagating BCGE for $\mu_{e,1}=0$ (as shown) or $\mu_{e,2}=0$ (not shown); so, the band of charged reagent species collides with the stationary band of uncharged reagent species in its well.
Figure 1E:
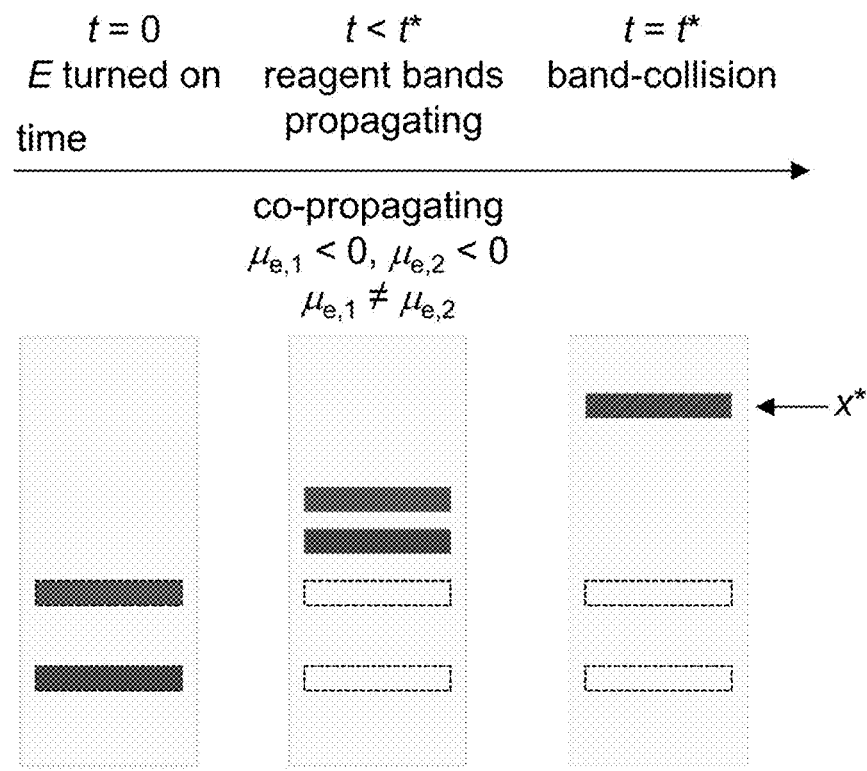
FIG. 1E shows co-propagating BCGE for $\mu_{e,1}$ and $\mu_{e,2}$ which have the same sign (<0 as shown in this example) but $\mu_{e,1} \neq \mu_{e,2}$; so, band-collision occurs at x* outside the region between the two wells.

Several different scenarios for generating collisions of bands are possible using BCGE (see FIGS. 1C-1E). In the most common scenario, which we call 'counter-propagating' BCGE, the collision location always occurs between the two wells; the electrophoretic mobilities of the two reagent species must have opposite signs and must be loaded into the appropriate wells such that $\mu_{e,1}>0$ and $\mu_{e,2}<0$. This ensures that the difference $\mu_{e,1}-\mu_{e,2}$, which appears in the denominators of the expressions for t* and x*, is always positive. Two other scenarios, which we collectively call 'uni-propagating' BCGE, involve reacting a charged reagent species with an uncharged one. If the charged reagent species has a positive charge, then we consider it to be reagent species 1 such that $\mu_{e,1}>0$ and it is loaded into the well at x=0; the uncharged reagent species 2, which therefore has $\mu_{e,2}=0$, is consequently loaded into the well at x=L. Because the uncharged reagent species does not propagate when the field is turned on (or possibly displaces only slightly as a consequence of potential electro-osmotic effects), the collision point of the bands will be $x^*\approx L$. By contrast, if the reagent species has a negative charge, then we consider it to be reagent species 2 such that $\mu_{e,2}<0$ and it is loaded into the well at x=L; the uncharged reagent species 1, which therefore has $\mu_{e,1}=0$, is consequently loaded into the well at x=0. Because the uncharged reagent species does not propagate when the field is turned on (or possibly displaces only slightly as a consequence of potential electro-osmotic effects), the collision point of the bands in this case will be $x^*\approx 0$. Alternatively, in yet a different scenario, which we call 'co-propagating' BCGE, $\mu_{e,1}$ has the same sign as $\mu_{e,2}$, yet their magnitudes are different such that $\mu_{e,1}\neq\mu_{e,2}$. In this case, the difference $\mu_{e,1}-\mu_{e,2}$, which appears in the denominators of the expressions for t* and x*, is non-zero and a collision can still occur, yet the value for x* corresponds with a location that is outside of the region between the two wells. For co-propagating BCGE, in which one reagent species appears to catch up with the other reagent species, care must be taken in selecting a sufficiently small value of L so that the collision location x* occurs inside the physical boundaries of the gel.

The above equation for the collision time t* clearly reveals that it becomes impossible to generate a collision between bands when $\mu_{e,1}=\mu_{e,2}$, since t* effectively diverges and becomes infinite in the limit as $\mu_{e,1}$ approaches $\mu_{e,2}$. Even if $\mu_{e,1}\approx\mu_{e,2}$ yet the two electrophoretic mobilities are not strictly equal, it can become practically impossible to generate a collision of bands within the physical boundaries of the gel, even if L is chosen to be very small. Thus, for $\mu_{e,1}\approx\mu_{e,2}$, the only viable approach that can enable the reagent species to interact is to load them in the same well initially, generating the limiting case of the electrophoretic mobility shift assay (EMSA).

As an example of a co-propagating collision of bands created using BCGE, we have loaded the first well at x=0.0 mm with AR dye ($\mu_{e,1}=-2.75\times10^{-8}$ m$^2$ V$^{-1}$ s$^{-1}$) and the second well at x=L=5.0 mm in the same lane with BB dye ($\mu_{e,2}=-1.68\times10^{-8}$ m$^2$ V$^{-1}$ s$^{-1}$). At pH=9.0, both dyes are negatively charged, so their electrophoretic mobilities have the same sign but significantly different magnitudes. As predicted, the collision of the two different bands of dyes occurs in the gel outside of the region between the two wells at $x^*\approx-12.8$ mm. In this experiment, no interaction between the colliding bands was observed, and the space-time plot reveals no deviations in propagation of the dyes or additional streaks indicating complex formation as a consequence of the collision. We reason that this is because electrostatic interactions between these like-sign small-molecule reagent dye species are dominantly screened-charge repulsions; so, no complex forms, even transiently. However, this single result does not imply by itself that other molecular types, such as those that have long hydrophobic chains in addition to charge, would not visibly react or associate in a catch-up BCGE scenario. Likewise, some types of redox reactions involve two negatively charged species that have significantly different electrophoretic mobilities, and these could potentially be probed as a function of reagent concentrations using catch-up BCGE.

Estimating electrophoretic mobilities of invisible reagent species. For invisible reagent species, if the average collision location x* and average time-to-collision t* associated with measureable evidence of product formation can be detected, then it is possible to determine the electrophoretic mobilities of both reagent species. Dividing the equation for x* by the equation for t* and solving, the electrophoretic mobility of the first reagent species is given by: $\mu_{e,1}=(x^*/t^*)/E$. Using this result, the electrophoretic mobility of the second reagent is given by: $\mu_{e,2}=\mu_{e,1}-(L/t^*)/E$. These equations can also be used to determine the electrophoretic mobilities of visible reagents from the measured collision time and location; although these reagent mobilities could also be determined by tracking the velocities of the propagating visible bands before collision, too. Because of the potential for Brownian diffusion of reagent species in addition to electrophoretic propagation, the first evidence of product formation may not correspond precisely to t*, since the leading edge of the band is diffuse. So, when determining t* from product formation, it is typically best associated with the peak production of product species, not the first observable evidence of product species.

Using BCGE, if a visible or otherwise detectable reaction product is formed between colliding bands of two different reactant species, whether these reactant species are invisible or visible, then electrophoretic mobilities of both reactant species can be deduced from the location of the detected reaction product relative to the wells where the reactant species were loaded, the elapsed time associated with the maximum detected product formation after activation of the electric field, and the strength and direction of the electric field. As an example, we determine electrophoretic mobilities of invisible reactant species by performing BCGE between bands of visible dyes and invisible ionic surfactants. Bands of cationic dyes are collided with with bands of DS$^-$ (FIG. 7L), and bands of anionic dyes are collided with bands of DTA$^+$ (FIG. 7M). Stationary, neutral complexes form when DS$^-$ collides with MAL, MB, and MG, and also when DTA$^+$ collides with AR, BB, BPB, and BCG. Given the locations and times of formation of the stationary bands of the neutral complexes, as well as the applied field strength, we estimate the velocities of the invisible reactant species and then determine that the values of $\mu_e$ for DS$^-$ and DTA$^+$ at these conditions are $-1.1\times10^{-8}$ m$^2$ V$^{-1}$ s$^{-1}$ and +1.4×10⁻⁸ m² V⁻¹ s⁻¹, respectively. In a different BCGE trial, we have also collided a band of invisible $Sr^{2+}$ with a counter-propagating band of invisible $DS^-$ to form the white insoluble precipitate $Sr(DS)_2$, which is readily detected optically against a black background using side illumination of the gel rather than transmission illumination. Because the velocities of both invisible species can be determined by the distances of propagation from the loaded wells to the collision point, and the time associated with the collision and detected product formation, one can deduce the electrophoretic mobilities of both the invisible $Sr^{2+}$ and the invisible $DS^-$ reactant species.

Modeling the effective hydrodynamic radii of dyes. We build molecular models of dyes (HyperChem Professional 8.0.7). We include charges on charge groups according to the acid/base chemistry of that particular dye at the given pH=9.0 (see Supplementary Methods and FIGS. 8A-8J). The model is geometry-optimized in vacuo until convergence with a root mean-square gradient of <0.1 kcal/(A mol) using the Polak-Ribiere conjugate gradient algorithm[66]. Optimized geometries are placed in a 20 Å cubic periodic bounding box populated with approximately 195-245 water molecules depending on the size of the dye. The minimum distance between solvent and solute is set at 2.3 Å. Molecular mechanics are calculated using the AMBER force field with bond, angle, torsion, non-bonded, electrostatic, and hydrogen-bonded components. Options include a constant dielectric of scale factor 1 (i.e. water), switched inner and outer cutoff radii of 6 and 10 Å, respectively, and 1-4 scale factors (non-bonded interactions separated by exactly 3 covalent bond distances) of 0.5 for electrostatic and van der Waals interactions to reduce the exaggerated short-range repulsion of the Lennard-Jones 6-12 potential. After convergence, water molecules are removed, and solvated dye structures (see FIGS. 9A-9J) are imported into WinHydroPRO v1.00 PUB (temperature T=20.0° C., solvent viscosity=1.00 mPa s, partial specific volumes of ≈1.0 cm³/g). Hydrogen atoms are ignored. Atomic radii of non-H atoms in a bead model are assigned values of 2.84 Å (see prior publication[67]), resulting in an average van der Waals radius of ≈2.9 Å and a 1.1 Å hydration layer. These modeling results yield a hydrodynamic translational radius for each dye molecule, which is used in the Stokes drag factor to predict its mobility.

REFERENCES

1. Casse, F., Boucher, C., Julliot, J. S., Michel, M. & Denarie, J. Identification and characterization of large plasmids in *Rhizobium meliloti* using agarose gel electrophoresis. *J. Gen. Microbiol.* 113, 229-242 (1979).
2. Chrambach, A. & Rodbard, D. Polyacrylamide gel electrophoresis. *Science* 172, 440-451 (1971).
3. Lehrach, H., Diamond, D., Wozney, J. M. & Boedtker, H. RNA molecular weight determinations by gel electrophoresis under denaturing conditions, a critical reexamination. *Biochemistry* 16, 4743-4751 (1977).
4. Lesnaw, J. A. & Reichmann, M. E. Determination of molecular weights of plant viral protein subunits by polyacrylamide gel electrophoresis. *Virology* 42, 724-731 (1970).
5. Noble, R. P., et al. Comparison of lipoprotein analysis by agarose gel and paper electrophoresis with analytical ultracentrifugation. *Lipids* 4, 55-59 (1969).
6. Schwartz, D. C. & Cantor, C. R. Separation of yeast chromosome-sized DNAs by pulsed field gradient gel electrophoresis. *Cell* 37, 67-75 (1984).
7. Sun, Y. L., Xu, Y. Z. & Chambon, P. A simple and efficient method for the separation and detection of small DNA fragments by electrophoresis in formamide containing agarose gels and southern blotting to DBM-paper. *Nucleic Acids Res.* 10, 5753-5763 (1982).
8. Lee, P. Y., Costumbrado, J., Hsu, C. Y. & Kim, Y. H. Agarose gel electrophoresis for the separation of DNA fragments. *J. Vis. Exp.* 62, (2012) doi: 10.3791/3923.
9. Herring, A. J., Inglis, N. F., Ojeh, C. K., Snodgrass, D. R. & Menzies, J. D. Rapid diagnosis of rotavirus infection by direct detection of viral nucleic acid in silver-stained polyacrylamide gels. *J. Clin. Microbiol.* 16, 473-477 (1982).
10. Kaufmann, E., Geisler, N. & Weber, K. SDS-PAGE strongly overestimates the molecular masses of the neurofilament proteins. *FEBS Lett.* 170, 81-84 (1984).
11. Ikeuchi, M. & Inoue, Y. A new 4.8-kDa polypeptide intrinsic to the PS II reaction center, as revealed by modified SDS-PAGE with improved resolution of low-molecular-weight proteins. *Plant Cell Physiol.* 29, 1233-1239 (1988).
12. Carraro, U. & Catani, C. A sensitive SDS-PAGE method separating myosin heavy chain isoforms of rat skeletal muscles reveals the heterogeneous nature of the embryonic myosin. *Biochem. Biophys. Res. Commun.* 116, 793-802 (1983).
13. Tenover, F. C., et al. Interpreting chromosomal DNA restriction patterns produced by pulsed-field gel electrophoresis—Criteria for bacterial strain typing. *J. Clin. Microbiol.* 33, 2233-2239 (1995).
14. Gautom, R. K. Rapid pulsed-field gel electrophoresis protocol for typing of *Escherichia coli* O157:H7 and other gram-negative organisms in 1 day. *J. Clin. Microbiol.* 35, 2977-2980 (1997).
15. Bannerman, T. L., Hancock, G. A., Tenover, F. C. & Miller, J. M. Pulsed-field gel electrophoresis as a replacement for bacteriophage typing of *Staphylococcus aureus*. *J. Clin. Microbiol.* 33, 551-555 (1995).
16. Hyrien, O. & Mechali, M. Plasmid replication in Xenopus eggs and egg extracts—a 2D gel electrophoretic analysis. *Nucleic Acids Res.* 20, 1463-1469 (1992).
17. Celis, J. E. & Gromov, P. 2D protein electrophoresis: Can it be perfected? *Curr. Opin. Biotechnol.* 10, 16-21 (1999).
18. Farrell, P. J., Hunt, T. & Jackson, R. J. Analysis of phosphorylation of protein synthesis initiation factor eIF-2 by two-dimensional gel electrophoresis. *Eur. J. Biochem.* 89, 517-521 (1978).
19. Nakano, K., et al. Development of a highly sensitive three-dimensional gel electrophoresis method for characterization of monoclonal protein heterogeneity. *Anal. Biochem.* 438, 117-123 (2013).
20. Salimullah, M., Mori, M. & Nishigaki, K. High-throughput three-dimensional gel electrophoresis for versatile utilities: A stacked slice-gel system for separation and reactions (4SR). *Genomics Proteomics Bioinformatics* 4, 26-33 (2006).
21. Mauro, S., Colignon, B., Dieu, M., Delaive, E. & Raes, M. Three-dimensional electrophoresis for quantitative profiling of complex proteomes. *Methods Mol. Biol.* 1295, 427-440 (2015).
22. Hellman, L. M. & Fried, M. G. Electrophoretic mobility shift assay (EMSA) for detecting protein-nucleic acid interactions. *Nat. Protoc.* 2, 1849-1861 (2007).
23. Jing, D., Agnew, J., Patton, W. F., Hendrickson, J. & Beechem, J. M. A sensitive two-color electrophoretic 23. mobility shift assay for detecting both nucleic acids and protein in gels. *Proteomics* 3, 1172-1180 (2003).
24. Laurell, C.-B. Electroimmuno assay. *Scand. J. Clin. Lab. Inv.* 29, 21-37 (1972).
25. Georges, M. Mapping, fine mapping, and molecular dissection of quantitative trait loci in domestic animals. *Annu. Rev. Genom. Hum. G.* 8, 131-162 (2007).
26. White, C. M., Satz, A. L., Bruice, T. C. & Beerman, T. A. Inhibition of transcription factor-DNA complexes and gene expression by a microgonotropen. *Proc. Natl. Acad. Sci. U.S.A.* 98, 10590-10595 (2001).
27. Bellamy, S. R. W., Kovacheva, Y. S., Zulkipli, I. H. & Halford, S. E. Differences between $Ca^{2+}$ and $Mg^{2+}$ in DNA binding and release by the SfiI restriction endonuclease: implications for DNA looping. *Nucleic Acids Res.* 37, 5443-5453 (2009).
28. Fried, M. & Crothers, D. M. Equilibria and kinetics of lac repressor-operator interactions by polyacrylamide gel electrophoresis. *Nucleic Acids Res.* 9, 6505-6525 (1981).
29. Fried, M. G. & Bromberg, J. L. Factors that affect the stability of protein-DNA complexes during gel electrophoresis. *Electrophoresis* 18, 6-11 (1997).
30. Fried, M. G. & Crothers, D. M. Kinetics and mechanism in the reaction of gene regulatory proteins with DNA. *J. Mol. Biol.* 172, 263-282 (1984).
31. Fried, M. G. & Liu, G. Molecular sequestration stabilizes CAP-DNA complexes during polyacrylamide gel electrophoresis. *Nucleic Acids Res.* 22, 5054-5059 (1994).
32. Goodrich, J. A. & Kugel, J. F. Studying the affinity, kinetic stability, and specificity of RNA/protein interactions: SINE ncRNA/Pol II complexes as a model system. *Methods Mol. Biol.* 1206, 165-178 (2015).
33. Ruusala, T. & Crothers, D. M. Sliding and intermolecular transfer of the lac repressor: kinetic perturbation of a reaction intermediate by a distant DNA sequence. *Proc. Natl. Acad. Sci. U.S.A.* 89, 4903-4907 (1992).
34. Sidorova, N. Y., Muradymov, S. & Rau, D. C. Solution parameters modulating DNA binding specificity of the restriction endonuclease EcoRV. *FEBS J.* 278, 2713-2727 (2011).
35. Vossen, K. M. & Fried, M. G. Sequestration stabilizes lac repressor-DNA complexes during gel electrophoresis. *Anal. Biochem.* 245, 85-92 (1997).
36. Derbyshire, A. N. & Peters, R. H. Interaction between Chlorazol Sky Blue FF and Chrysophenine G in aqueous solution. *J. Soc. Dyers Colour.* 72, 268-277 (1956).
37. Morita, Z. & Sekido, M. Studies on mixture dyeing. III. Absorption spectra of direct dye mixtures in an aqueous solution. *Bull. Chem. Soc. Jpn.* 38, 2041-2044 (1965).
38. Quadrifoglio, F. & Crescenzi, V. Interaction of methyl orange and other azo-dyes with polyelectrolytes and with colloidal electrolytes in dilute aqueous solution. *J. Colloid Interface Sci.* 35, 447-459 (1971).
39. Sheth, G. N. Studies in interaction between polyvinyl pyrrolidone and stilbene fluorescent compounds II. Interaction with mixture of compounds. *J. Appl. Polym. Sci.* 32, 4333-4342 (1986).
40. Kobayashi, T., Saito, K., Tanizaki, Y. & Ando, N. Absorption spectra of dyes. VII. Some steric effects and auxochrome-effects on complex formation. *Bull. Chem. Soc. Jpn.* 35, 935-939 (1962).
41. Inscoe, M. N., Gould, J. H., Corning, M. E. & Brode, W. R. Relation between the absorption spectra and the chemical constitution of Dyes: XXIX. Interaction of direct azo dyes in aqueous solution. *J. Res. Nat. Bur. Stand.* 60, 65-83 (1958).
42. Sabnis, R. W. Handbook of Biological Dyes and Stains: Synthesis and Industrial Applications (Hoboken, NJ, Wiley, 2010).
43. Gloria, M. B. A. & Fernandes, C. Synthetic Colorants. In: Nollet LML, Toldra F (eds). *Handbook of Food Analysis,* 3rd ed. (Boca Raton, CRC Press, 2015), pp 105-132.
44. Yeh, D.-B. Polyacrylamide gel electrophoresis of water-soluble coal-tar dyes. *J. Chromatogr. A* 132, 566-568 (1977).
45. Bikos, D. A. & Mason, T. G. Influence of ionic constituents and electrical conductivity on the propagation of charged nanoscale objects in passivated gel electrophoresis. *Electrophoresis* 39, 394-405 (2018).
46. Hsieh, Y. S. & Crouch, S. R. A stopped-flow continuous-flow method for kinetic determinations. *Anal. Chim. Acta* 309, 277-282 (1995).
47. Parker, B. F., Zhang, Z. C., Leggett, C. J., Arnold, J. & Rao, L. F. Kinetics of complexation of V(V), U(VI), and Fe(III) with glutaroimide-dioxime: Studies by stopped-flow and conventional absorption spectroscopy. *Dalton Trans.* 46, 11084-11096 (2017).
48. Zhang, J. Y., Chen, S. G., Zhu, Z. Y. & Liu, S. Y. Stopped-flow kinetic studies of the formation and disintegration of polyion complex micelles in aqueous solution. *Phys. Chem. Chem. Phys.* 16, 117-127 (2014).
49. Phillips, W. D. & Metcalf, H. Laser deceleration of an atomic beam. *Phys. Rev. Lett.* 48, 596-599 (1982).
50. King, D. A. & Wells, M. G. Molecular-beam investigation of adsorption kinetics on bulk metal targets—nitrogen on tungsten. *Surf. Sci.* 29, 454-482 (1972).
51. Barker, J. A. & Auerbach, D. J. Gas-surface interactions and dynamics: Thermal energy atomic and molecular beam studies. *Surf. Sci. Rep.* 4, 1-99 (1984).
52. Beijerinck, H. C., Moonen, R. G. J. M. & Verster, N. F. Calibration of a time-of-flight machine for molecular beam studies. *J. Phys. E Sci. Instrum.* 7, 31-36 (1974).
53. Smoluchowski, M. Contribution à la théorie de l'endosmose électrique et de quelques phénomènes corrélatifs. *Bull. Int. Acad. Sci. Cracovie.* 3, 182-199 (1903).
54. Pernodet, N., Maaloum, M. & Tinland, B. Pore size of agarose gels by atomic force microscopy. *Electrophoresis* 18, 55-58 (1997).
55. Harvey, A. E., Komarmy, J. M. & Wyatt, G. M. Colorimetric determination of magnesium with Eriochrome Black T. *Anal. Chem.* 25, 498-500 (1953).
56. Durham, A. C. H. & Walton, J. M. A survey of the available colorimetric indicators for $Ca^{2+}$ and $Mg^{2+}$ ions in biological experiments. *Cell Calcium* 4, 47-55 (1983).
57. Christian, G. D., Dasgupta, P. K. & Schug, K. *Analytical Chemistry,* 7th ed. (Hoboken, NJ, Wiley, 2014).
58. Gjems, O. Stoicheiometry of titration of calcium, magnesium and manganese at low concentration with EDTA, with the metal indicators murexide and Eriochrome Black T. *Analyst* 85, 738-744 (1960).
59. Eigen, M. & Johnson, J. S. Kinetics of reactions in solution. *Annu. Rev. Phys. Chem.* 11, 307-334 (1960).
60. Moore, J. S., Phillips, G. O., Power, D. M. & Davies, J. V. Polyanions and their complexes. Part VII. Mechanism of methylene blue-polyanion interactions. *J. Chem. Soc. A* 1155-1159 (1970).
61. Zhu, X. & Mason, T. G. Passivated gel electrophoresis of charged nanospheres by light-scattering video tracking. *J. Colloid Interface Sci.* 428, 199-207 (2014).

62. Savenko, A. V. Solubility products of strontium carbonate and strontium sulfate in aqueous solution. *Russ. J. Inorg. Chem.* 46, 1102-1107 (2001).
63. Bray, W. C. & Liebhafsky, H. A. Reactions involving hydrogen peroxide, iodine and iodate ion. I. Introduction. *J. Am. Chem. Soc.* 53, 38-44 (1931).
64. Whittle, E., Dows, D. A. & Pimentel, G. C. Matrix isolation method for the experimental study of unstable species. *J. Chem. Phys.* 22, 1943-1943 (1954).
65. Riedel, S., Kochner, T., Wang, X. & Andrews, L. Polyfluoride anions, a matrix-isolation and quantum-chemical investigation. *Inorg. Chem.* 49, 7156-7164 (2010).
66. Polak, E. & Ribiere, G. Note on convergence of conjugate direction methods. *Rev. Fr. Inform. Rech. O.* 3, 35-43 (1969).
67. Ortega, A., Amoros, D. & de la Tone, J. G. Prediction of hydrodynamic and other solution properties of rigid proteins from atomic- and residue-level models. *Biophys. J.* 101, 892-898 (2011).

TABLE 2

Fitting parameters for MG:BPB variable field strength experiments.
$I_{green} = I_b + I_{rise}/\{1 + \exp[-(t - \tau_0)/\tau_c]\}$

| $E_c$ (V/cm) | $I_b$ | $\tau_0$ (s) | $\tau_c$ (s) | $I_{rise}$ | $R^2$ |
|---|---|---|---|---|---|
| 3.1 | 81.3 ± 0.5 | 1,876.2 ± 1.7 | 88.1 ± 1.5 | 166.2 ± 0.6 | 0.999 |
| 6.2 | 84.6 ± 0.9 | 932.5 ± 1.8 | 54.3 ± 1.5 | 166.8 ± 1.0 | 0.997 |
| 9.4 | 91.9 ± 1.3 | 665.0 ± 2.0 | 36.6 ± 1.8 | 154.1 ± 1.4 | 0.993 |

TABLE 1

Detailed compound information.

| Compound | $M_w$ (g mol$^{-1}$) | Manufacturer | Product no. | CAS no. | Lot no. | Purity (manufacturer reported) |
|---|---|---|---|---|---|---|
| Tartrazine (as Acid Yellow 23) $C_{16}H_9N_4Na_3O_9S_2$ | 534.36 | TCI | F0088 | 1934-21-0 | W7BPB-HG | >98.0% |
| Allura Red AC $C_{18}H_{14}N_2Na_2O_8S_2$ | 496.42 | TCI | A0943 | 25956-17-6 | GJ01-QTAH | not provided |
| Brilliant Blue FCF (as Erioglaucine disodium salt, pure) $C_{37}H_{34}N_2Na_2O_9S_3$ | 792.84 | ACROS Organics | 229730050 | 3844-45-9 | A0373695 | "pure" |
| Bromophenol Blue (sodium salt) $C_{19}H_9Br_4NaO_5S$ | 691.94 | Sigma Chemical Company | B6131 | 34725-61-6 | 16F-3675 | technical grade |
| Bromocresol Green (0.1% w/v aqueous) $C_{21}H_{14}Br_4O_5S$ | 698.02 | The Science Company | NC-13321 | 76-60-8 | B10311241701 | ACS reagent grade |
| Cyanocobalamin $C_{63}H_{88}CoN_{14}O_{14}P$ | 1355.37 | Sigma Life Science | V2876 | 68-19-9 | MKCB7713 | ≥98% |
| Rhodamine B (as Rhodamine 610 Chloride) $C_{28}H_{31}ClN_2O_3$ | 479.02 | Exciton | Not provided | 81-88-9 | Lot # F | not provided |
| Malachite Green $C_{23}H_{25}ClN_2$ | 364.91 | Matheson Coleman & Bell | B329 | 569-64-2 | CMg 20 C.I. no. 42000 | 99% |
| Methylene Blue $C_{16}H_{18}ClN_3S$ | 319.85 | Fisher | M-291 | 61-73-4 | 931790B | 91% |
| Methyl Green $C_{27}H_{35}BrClN_3 \cdot ZnCl_2$ | 653.24 | Sigma Chemical Company | No. M-8884 | 7114-03-6 | 65F-3657 | 90% |
| Heparin (sodium salt from porcine intestinal mucosa - Grade I-A) | 203 USP units/mg | Sigma-Aldrich | H3393 | 9041-08-1 | SLBG1344V | ≥180 USP units/mg |
| Sodium dodecyl sulfate $NaC_{12}H_{25}SO_4$ | 288.37 | MP Biomedical | 811030 | 151-21-3 | M9622 | ≥99% |
| Dodecyltrimethylammonium bromide $CH_3(CH_2)_{11}N(CH_3)_3Br$ | 308.35 | Acros Organics | 409311000 | 1119-94-4 | A035872 | 99% |
| Hydrogen peroxide $H_2O_2$ | 34.01 | Fisher Scientific | H327-500 | 7722-84-1 | 90592 | 34-37% |
| Potassium iodide KI | 166.00 | Alfa Aesar | 11601 | 7681-11-0 | P14C053 | 99.0% min |
| Strontium chloride SrCl | 183.68 | Mallinckrodt Chemical Works | N/A | 10476-85-4 | B-905 | not provided |
| Sulfate-stabilized polystyrene spheres (a = 42 nm) | N/A | Interfacial Dynamics | 1-80 | 9003-53-6 (polystyrene) | 1524.1 | N/A |
| Hydrochloric acid HCl (50% v/v) | 36.46 | Ricca | 3580-16 | 10476-85-4 | 1606C62 | 50% (v/v) |
| Ethylenediaminetetraacetic acid $C_{10}H_{16}N_2O_8$ | 292.24 | Acros Organics | 446081000 | 60-00-4 | A0379536 | 99% |
| Eriochrome black T $C_{20}H_{12}N_3O_7SNa$ | 461.38 | Alfa Aesar | A17536 | 1787-61-7 | 10206882 | not provided |
| Calcium chloride, dihydrate $CaCl_2 \cdot 2H_2O$ | 40.08 | EMD | CX0130-1 | 10035-04-8 | 41046503 | ACS reagent grade |
| Sodium borate, decahydrate $Na_2B_4O_7 \cdot 10H_2O$ | 381.42 | Fisher Scientific | S25537A | 1303-96-4 | 7GK37263 | reagent grade |
| Chloro-acetic acid $ClCH_2COOH$ | 94.50 | Alfa Aesar | A11482 | 79-11-8 | W17A016 | 99% |

TABLE 3

Fitting parameters for MB:BB variable field strength experiments.
$I_{green} = 255 - \{A/[(t - \tau_i)\sigma]\} \exp[-\{\ln[(t - \tau_i)/\tau_d]\}^2/(2\sigma^2)]$ for $t > \tau_i$; $I_{green} = 255$ for $0 \leq t \leq \tau_i$

| $E_c$ (V/cm) | A (s) | $\tau_i$ (s) | $\tau_d$ (s) | $\sigma$ | $R^2$ |
|---|---|---|---|---|---|
| 3.1 | $1.47 \pm 0.01 \times 10^5$ | $952.1 \pm 4.7$ | $1.72 \pm 0.02 \times 10^3$ | $1.14 \pm 0.01$ | 0.983 |
| 6.2 | $8.53 \pm 0.14 \times 10^4$ | $484.6 \pm 5.3$ | $881 \pm 19$ | $1.10 \pm 0.02$ | 0.969 |
| 9.4 | $4.34 \pm 0.67 \times 10^4$ | $360.5 \pm 2.3$ | $454.2 \pm 9.8$ | $1.15 \pm 0.02$ | 0.984 |

Supplementary Methods
Determining Total Charge on Molecular Ions

Molecular ions that are known to absorb visible light can be categorized according to the presence of structural motifs associated with their optical properties[1]. All anionic molecules used in this investigation contain at least one alkyl sulfonate group. Sulfonates are very strong acids with $pK_a$ values less than zero[2] and for practical purposes can be assumed to remain deprotonated throughout the pH range in most experiments, including our study. The acid dissociation constants are available in the literature for the following dyes: tartrazine (TZ)[3,4], allura red AC (AR)[3], brilliant blue FCF (BB)[5,6], bromophenol blue (BPB)[7], bromocresol green (BCG)[8], cyanocobalamin (B12)[9], rhodamine B (RB)[10], malachite green (MAL)[11,12], methylene blue (MB)[13], methyl green (MG)[14], and neutral (RB, vitamin B12) dyes[15]. The slow cationic propagation of RB and B12 that we observe can be attributed to electroosmotic flow[16]. The molecular ions BB, BPB, BCG, MAL, and MG belong to the triarylmethane class. Two highly acidic tosyl groups extend the structure of BB, providing flexibility in distinguishing this molecular ion from others used in our study. BB has two reported $pK_a$ values[6]: 5.83 and 6.58. The BB molecule is zwitterionic with a predicted overall charge of −2e in a pH=9.0 solution. Structurally, BPB and BCG differ only by the presence of a methyl group in two of three aryl rings. BPB has a spectroscopically determined $pK_a$ of 3.95[7] associated with a widely-known color change from yellow to blue between pH 3.0 and 4.6, respectively. The phenolic oxygen remains deprotonated below this value[17] until a structural rearrangement occurs, which neutralizes the overall charge of the molecular ion[18]. A $pK_a$ of 4.85 has been measured for BCG[8]. It is predicted that BCG exists in its monoanionic form below pH=4.85, above which the molecular ion is dianionic[19]. MAL changes color from yellow to green, then green to colorless between pH values of 0.0 to 2.0 and 11.6 to 14.0, respectively. Identification of a $pK_a$ at 6.90 appears to correspond to a kinetically limited hydrolysis reaction involving a structural transition with an associated $pK_{hyd}$ of 6.9[12]. We observe no change in electrophoretic mobility for MAL below pH=6.90 in our experiments. The $pK_a$ of the amino group in MAL is 2.2[11]. We predict that MAL has a +1e charge at pH=9.0. MG undergoes a color change from yellow to greenish-blue at a pH of 0.1 to 2.3 and has a $pK_a$ within the range of 0.2-1.8[14]. Two quaternary nitrogens remain positively charged across a wide spectrum of pH imparting a charge of +2e at pH=9.0. Many triarylmethane molecular ions are known to slowly form colorless carbinols at higher pH values[12]. MAL and MG have been reported to undergo this hydrolysis reaction at pH 9.0[11]; however, time scales for this hydrolysis reaction are much longer than our typical observation times after loading and running gels, so we find that this potential effect is negligible in our study. We dissolve molecular ions in pure water (with some $D_2O$ as described in the Methods) and perform experiments in under 1 hour to prevent accumulation of hydrolysis products.

Two azo-class molecules represented in this study are TZ and AR, characterized by the presence of functional group R—N=N—R'. TZ undergoes an azo-hydrazone tautomerization reaction characteristic of pyrazolones. The sulfonate and carboxylate moieties of TZ suggest the molecular ion can possess a charge of −3e across a wide range of pH values. It is only for pH>10, that TZ exists predominantly in a tetra-anionic form[20]. Spectroscopic methods have measured the $pK_a$ of TZ to be 9.4[3], a value corroborated by fixed titration methods[4]. Despite the proximity of the $pK_a$ of TZ to the pH of SBB, we observe best agreement to theory at a charge of +3e. TZ does not readily form aggregates or dimers in aqueous solution[21]. AR contains two negatively charged sulfonate groups with an azo group $pK_a$ of 11.4 in aqueous solution[3]. In the range of pH investigated, AR is predicted to possess a charge of +2e.

MB is a heterocyclic dye of the thiazine class. The molecular ion of MB is a planar phenothiazine with a $pK_a$ identified as 3.8[13] or alternatively 2.6 and 11.2. The predicted charge of MB at pH=9.0 is +1e.

The cyanocobalamin vitamer B12 has a cherry color that is produced by the cobalt-corrin complex at its center. 'Vitamin' B12 has three reported $pK_a$ values corresponding to 1.0, 2.9, and 4.7[9]. At a pH of 9.0, B12 should be fully neutral. Its presumed neutrality has made it a popular probe for measuring electroosmotic flow.

RB is a fluorone zwitterion with a $pK_a$ of 3.1[10]. Its carboxylate group is neutralized and deprotonated under pH of 3.1 giving the molecular ion a charge of +1e. Individual charges on the amine and carboxylate cancel at pH=9.0 giving RB a net charge close to zero.

In our experiments, BB does not propagate as rapidly as its size and charge would predict, at least on first cursory inspection. However, a reasonable explanation may be found in the flexibility of the solvated BB zwitterion. Solvated geometry optimization predicts that attractions between charges within the BB molecule will result in a folded structure. Folding may increase charge screening. As most molecular dyes have similar sizes, it is likely that folding results in charge screening, which in turn lowers the propagation rate for BB. The indicators BPB and BCG also propagate more slowly than predicted. It may be possible that partial protonation leads to a slightly lower non-integer time-average charge for these molecular ions.

Using the predicted charges on charge groups at pH=9.0, we have calculated structures of dye molecules, as shown in Supplementary Table 1 (see main Methods section for modeling software used and model parameters). Positive and negative signs indicate regions of appreciable local charge density. For clarity, water molecules are not shown.

Intramolecular attraction between an anionic sulfate and a tertiary amine cation results in a folded structure in BB.

Supplementary Discussion

Alternative Illumination-Detection Modalities and Configurations for BCGE

While we have demonstrated the broad approach of band-collision gel electrophoresis (BCGE) through two different illumination-detection configurations involving optical absorption and scattering of visible light, BCGE is not inherently limited only to those two configurations and imaging modalities. In the transmission configuration/modality, we have illuminated bands of optically absorbing species (e.g. dyes) or refracting species (e.g. bubbles) with visible white light using a light box below the transparent gel electrophoresis (GE) chamber and a camera with lens above this chamber, thereby enabling us to image these species through reductions of transmitted light intensity at particular wavelengths. In the scattering configuration/modality, we have illuminated bands of optically absorbing, scattering, or refracting species with white light from the side (i.e. propagating predominantly in the plane of the gel at 90° with respect to the camera's optical axis) using one or two light boxes. In the case of the scattering configuration/modality, it is typically beneficial to place a black absorbing plastic film, paper, or cloth underneath the GE apparatus in order to enhance contrast of the light scattered by the scattering species towards the camera.

Beyond these two demonstrated illumination-detection configurations/modalities using white visible light, other configurations/modalities some of which may involve wavelengths beyond the visible spectrum, can also be useful for BCGE. For example, backscattering illumination of white light can be used, such that a light box or a fiber light is placed nearly in-line with the camera and pointed towards the gel (i.e. nearly along the optical axis of the camera's lens), so that the downward propagating light illuminates the GE apparatus and thus reagent/product species in the gel, and the camera collects upward propagating light that leaves the gel traveling in substantially the opposite direction. Beyond transmission and side illumination, this backscattering configuration/modality can be used to image absorbing, scattering, and refracting species.

Beyond visible white light illumination, BCGE can be readily extended to a fluorescence configuration/modality for imaging fluorescent molecular and colloidal species and also fluorescently labeled molecular and colloidal species that would otherwise be invisible. For instance, for fluorescent molecules that emit light at a visible wavelength when illuminated with ultraviolet (UV) light, a transmission geometry involving a UV light box and optical filter, which removes any residual visible light emanating from the UV illumination, can be used. The material for the chamber of the GE apparatus is typically chosen to appreciably transmit UV light at the absorption wavelength of the molecular dye, so that illuminating through the bottom of the GE apparatus does not cause a large reduction in the intensity of UV light that reaches the fluorescent molecules. For instance, although UV-filtering acrylic is the predominant form of manufactured acrylic, UV-transmitting acrylic is available and can readily be made into GE chambers suitable for BCGE involving UV illumination through the chamber. Typically, in order to avoid or reduce bleaching of the fluorescent molecules, it is also desirable for the UV illumination to be on (i.e. active) only periodically, rather than continuously, and coordinated with the periods of time during which the shutter of the camera is open. In some cases, it can be desirable to use broad-band UV light, which can excite a wide range of fluorescent molecules or fluorophores, and a filter that blocks UV light can be placed in front of the camera lens so that only visible fluorescent light, which could have different colors, falls on the camera's detector array. A control/acquisition computer can be used to coordinate the illumination intensity with the camera's shutter in order to optimize the signal-to-noise of the detected fluorescent light. Fluorescent or fluorescently labeled molecules that emit at different wavelengths can thus be imaged as different colors by the detecting camera, and time-lapse videos of the dynamics of reagent and product species can be detected in a manner similar to what we have demonstrated using optical absorption and white visible light illumination. Infrared (IR) wavelengths of light can also be used in illumination and/or detection; BCGE can utilize absorption, scattering, refraction, and fluorescence of IR light.

A potentially useful extension of BCGE involves labeling proteins and/or poly-nucleic acids (e.g. DNA and RNA) with different molecular fluorophores or fluorescent nanoparticles (e.g. quantum dots), and performing BCGE using UV (or visible) illumination to excite these fluorescent species while detecting the emitted fluorescent light in the visible (or IR) spectral range. Since bands of most proteins and poly-nucleic acids are typically invisible when illuminated with white visible light and since these biomolecules typically do not auto-fluoresce (with the exception being well-known proteins such as green fluorescent protein GFP and others of similar nature), it is typically necessary to fluorescently label such biomolecules in order to make them detectable and perform BCGE. It is typically desirable to label different biomolecules with different fluorophores, each of which emits light at a different wavelength, but all have excitation wavelengths in the range that are covered in the range corresponding to the UV illumination. Once labeled, these biomolecules can be loaded into wells and BCGE can be performed using UV illumination and visible detection in the manner prescribed above. Alternatively, such biomolecules can be labeled subsequent to loading using BCGE by colliding a band of invisible biomolecules with a band of fluorescent molecules that bind to the biomolecules, such that the labeled biomolecules can be seen using UV-illumination BCGE. This extension of BCGE to a fluorescence imaging modality will provide access to a wide range of reactions of otherwise invisible species, such as binding reactions, that include but are not limited to protein-protein, protein-DNA, protein-RNA, protein-ligand, DNA-DNA, and DNA-RNA reactions. By properly modulating the UV illumination intensity during the course of BCGE, the potential bleaching of fluorophores can be greatly reduced, and space-time plots of the reactions can be generated, just as we have demonstrated herein using visible white light illumination and absorbing dyes.

We envision that other experimental extensions of BCGE, related to optics of illumination and detection, could be readily implemented. In certain applications of BCGE, monochromatic or narrow-band polychromatic spectra of illumination could also be useful, rather than broadband illumination over wide continuous ranges of wavelengths. Likewise, the detection information can go beyond the limited and simple RGB detection offered by solid-state color array detectors. For instance in the white light transmission geometry, by using 2D scanning spectroscopy detection, facilitated by a fiber optic detector that is connected to a digital spectrometer and pointed towards the gel region, wherein this fiber is scanned along the x-direction and also perpendicular to it in the plane above the gel using a computer-controlled mechanical x-y stage. A lens on the end of the fiber optic detector can collect light from a very small spatial region, in order to spatially resolve details in the local spectra of evolving flow patterns during BCGE. Such a detection would provide a spatially resolved intensity versus wavelength as a function of spatial position, similar to a RGB color array detector, but with full view of all spectroscopic details. Using fiber optic 2D scanning spectroscopy detection would overcome a well-known limitation of RGB imaging: limited three-channel RGB intensity data does not contain enough information in order to enable conversion into full spectral data of intensity versus wavelength. In some cases, it can be desirable for the electric field to be temporarily turned off during the time period of 2D scanning of the fiber probe, so that the pattern of reagent and product species does not significantly evolve during this time period.

Programming Sequences of Collisions Using BCGE

In the simplest and most direct implementation of BCGE, desired sequences of collisions of pulses of reagent species can be programmed by designing the relative spacing between wells in the same lane. Each well is loaded with only a single reagent species in a manner that provides the desired reaction sequence when the electric field is applied, given the electrophoretic mobilities of the reagent species. In addition to this implementation, for certain reaction sequences, one can also program a sequence of collisions of propagating pulses of reagent species using fewer wells in the same lane by an alternative method that takes advantage of differences in electrophoretic mobilities within the gel between two or more reagent species that are non-binding and non-reactive.

For example, in the same lane with only two wells, one can program a sequence of collisions involving separated pulses of anionic TZ and AR dye molecules that are initially loaded into a first well with a pulse of counter-propagating cationic MG that is initially loaded into a second well, separated from the first well by a distance of at least several centimeters. The TZ and AR dyes are both anionic, so they interact primarily by short-range screened electrostatic repulsion and do not exhibit any binding or reaction when loaded in the same well. Because these dyes have different electrophoretic mobilities, mostly as a consequence of −3e charge on TZ versus −2e charge on AR, when the electric field is applied, the TZ propagates more rapidly than AR in the gel, leading to two separate bands that sequentially collide with counter-propagating MG. The TZ-MG band-collision occurs first, and then any unreacted MG that continues propagating collides with the band of more slowly propagating AR.

Beyond propagation along only a single spatial direction, we envision that BCGE can be extended to involve programmable propagation and collision of reagent and product species along two or even three different orthogonal spatial directions. In a simple implementation, one or two different pairs of electrodes can be added to the pre-existing pair of electrodes in the basic one-dimensional BCGE apparatus. These sets of orthogonally situated electrodes can be used to create electric fields that cause propagation of reagent and/or product species involving components of velocities along both orthogonal Cartesian x- and y-directions in the plane of a slab-like gel or along x-, y-, and z-directions for thicker cube-like gels, respectively. For instance, in a two-dimensional version of BCGE, two orthogonal pairs of Pt electrodes would be mounted in four side-troughs below the gel region, rather than just one pair in two side troughs (as shown in FIG. 1a). The initial well locations for the reagent species would involve specifying both x and y coordinates in a slab-like gel, and it may be advantageous to stagger the loading wells rather than keep them in rows. The shapes of the wells may be made into circles or squares, rather than long rectangular bands, yielding packets of reagent species. Electric field components $E_x$ and $E_y$ can be varied independently and/or simultaneously in time through two different power supplies controlled by a single computer. Time-varying current (e.g. alternating current AC) rather than time-independent current (e.g. direct current DC) can further be used to drive each pair of electrodes, thereby providing a means of programming sequences of reactions using BCGE in 2D. Similar modifications can be made to extend this extension of 2D-BCGE to 3D-BCGE.

Mitigating Gel-Matrix Interaction Effects in BCGE

When performing BCGE using certain reagent and product species, the potential effects of gel-matrix interactions on the reactions occurring within the gel can be largely neglected. This is typically true for small molecules and complexes in large-pore gels, and it is also typically true for passivated gels that have surfaces to which reagent and product species do not bind. However, it can potentially be desirable to cause bands to collisionally react in spatial regions that are purposefully designed to be devoid of gel, thereby obviating gel-matrix effects that could potentially interfere with the reactions and formation of products that are not intrinsically bound to the gel. With this in mind, when casting the gel it is possible to design a void in addition to making the two wells into a lane of the gel at and around the location given by x* where the band collision is predicted to occur. To appropriately fabricate the gel, it is necessary to know $\mu_{e,1}$ and $\mu_{e,2}$ in advance and to select L that enables a reasonable and physically accessible position of the void location at x* to be made when casting the gel. Thus, a given lane would then have three regions devoid of gel; one each at x=0 and x=L corresponding to the wells, and in addition one at x=x* where the collision of bands occurs. If desired, once the collision occurs in the void, E can be eliminated, and the product species can be eluted or otherwise removed from the void region of the gel after a desired reaction time.

Fitting Parameters for Decomplexing of MG:BPB and MB:BB

For MG:BPB decomplexing (FIG. 5B), we fit measured time-dependent intensity profiles of the green channel using a modified semi-empirical Fermi-like function $I_{green}=I_b+I_{rise}/\{1+\exp[-(t-\tau_0)/\tau_c]\}$. The fitting parameters are displayed in Table 2. For MB:BB decomplexing (FIG. 5D), we fit the measured time-dependent intensity profiles to a semi-empirical log-normal function related to optical absorption of the stationary band of product: $I_{green}=255-\{A/[(t-\tau_i)\sigma]\}\exp[-\{\ln[(t-\tau_i)/\tau_d]\}^2/(2\sigma^2)]$ for $t>\tau_i$ and $I_{green}=255$ for $0 \leq t \leq \tau_i$ (i.e. 255 corresponds to no optical absorption after ideal background subtraction). The fitting parameters are displayed in Table 3.

SUPPLEMENTARY REFERENCES

1. Kiernan J. A. Classification and naming of dyes, stains and fluorochromes. Biotech. Histochem. 76, 261-278 (2001).
2. Guthrie J. P. Hydrolysis of esters of oxy acids: $pK_a$ values for strong acids; Brønsted relationship for attack of water at methyl; free energies of hydrolysis of esters of oxy acids; and a linear relationship between free energy of hydrolysis and $pK_a$ holding over a range of 20 pK units. Can. J. Chem. 56, 2342-2354 (1978).

3. Pérez-Urquiza M. & Beltrán J. L. Determination of the dissociation constants of sulfonated azo dyes by capillary zone electrophoresis and spectrophotometry methods. *J. Chromatogr. A* 917, 331-336 (2001).
4. Xu G. Simultaneous determination of food pigments in mixtures by pH fixed titration. *J. Shangqiu Teachers College* 15, 79-83 (1999).
5. Flury M. & Flühler H. Brilliant blue FCF as a dye tracer for solute transport studies—A toxicological overview. *J. Environ. Qual.* 23, 1108-1112 (1994).
6. Flury M. & Flühler H. Tracer characteristics of brilliant blue FCF. *Soil Sci. Soc. Am. J.* 59, 22-27 (1995).
7. Patterson G. S. A simplified method for finding the pKa of an acid-base indicator by spectrophotometry. *J. Chem. Ed.* 76, 395-398 (1999).
8. Diamond D., Lau K. T., Brady S. & Cleary J. Integration of analytical measurements and wireless communications—Current issues and future strategies. *Talanta* 75, 606-612 (2008).
9. Lexa D. & Savéant J.-M. Brönsted basicity of vitamin B12s. *J. Chem. Soc. Chem. Commun.* 0, 872-874 (1975).
10. Arbeloa I. L. & Ojeda P. R. Molecular forms of rhodamine B. *Chem. Phys. Lett.* 79, 347-350 (1981).
11. Iogannsen M. G. Some structural features of vital dyes. *Bull. Exp. Bio. Med.* 83, 591-595 (1977).
12. Goldacre R. J. & Phillips J. N. 370. The ionization of basic triphenylmethane dyes. *J. Chem. Soc.* 1724-1732 (1949).
13. Kim J. R., Santiano B., Kim H. & Kan E. Heterogeneous oxidation of methylene blue with surface-modified iron-amended activated carbon. *Am. J. Analyt. Chem.* 4, 115-122 (2013).
14. Bishop E. Indicators, 1st ed. (Oxford, Pergamon Press, 1972).
15. Ouyang L., et al. Electronic structure and bonding in vitamin B-12, cyanocobalamin. *J. Mol. Struc.-Theochem.* 622, 221-227 (2003).
16. Quast R. Electroosmotic flow in agarose gels and value of agarose as stabilizing agent in gel electrofocusing. *J. Chromatogr.* 54, 405-412 (1971).
17. Maitra U., Mukhopadhyay S., Sarkar A., Rao P. & Indi S. S. Hydrophobic pockets in a nonpolymeric aqueous gel: Observation of such a gelation process by color change. *Angew. Chem. Int. Ed.* 40, 2281-2283 (2001).
18. Ferreira J. & Girotto E. M. pH effects on the ohmic properties of bromophenol blue-doped polypyrrole film. *J. Brazil Chem. Soc.* 21, 312-318 (2010).
19. Shokrollahi A. & Firoozbakht F. Determination of the acidity constants of neutral red and bromocresol green by solution scanometric method and comparison with spectrophotometric results. *Beni-Suef Univ. J. Appl. Sci.* 5, 13-20 (2016).
20. Bell S. $^{15}$N NMR investigation of azo-hydrazone acid-base equilibria of FD and C yellow no. 5 (tartrazine) and two analogs. *Dyes Pigments* 11, 93-99 (1989).
21. Asadzadeh Shahir A., Javadian S., Razavizadeh B. B. M. & Gharibi H. Comprehensive study of tartrazine/cationic surfactant interaction. *J. Phys. Chem. B* 115, 14435-14444 (2011).

In the field of chemistry, a reactant participates in a reaction and is consumed in that reaction, which produces a product, also known as a reaction-product. While the two terms, reagent and reactant, are sometimes used interchangeably even by those practicing in the field of chemistry, there is a distinction between these two different terms. A reactant is a substance of a particular type (e.g. of a reactant-species having a certain chemical composition, bonding types, and chemical structure) which, when added to a chemical system which includes other substances (e.g. is put in spatial proximity with these other substances), interacts with at least a portion of these other substances and is specifically consumed in a reaction that forms a product. By contrast, reagent is a more general term than reactant. A reagent is a substance that, when added to a chemical system which includes other substances (e.g. is put in spatial proximity with these other substances), may or may not react with these other substances. Thus, since a reagent may or may not react with these other substances when put in spatial proximity to these other substances, the lack of a reaction of a reagent with these other substances, including substances having an unknown composition, can convey useful information, particularly in the sub-field of analytical chemistry. As further examples, a reagent can be composed of substances such that not even one of said substances is a reactant; a reagent can be composed entirely of a single reactant; a reagent can be composed of a plurality of a single reactant-species (e.g. type of molecule); a reagent can be composed of a plurality of two or more different reactant-species in different proportions; and a reagent can be composed only in part of one or more different reactants. Even reagents that do not react when put in proximity with other substances can provide useful information, for instance, to test for the existence of certain reactions, even if no reaction actually occurs and no portion of a reagent is actually consumed. A reagent can be a mixture of many different kinds of substances in different proportions; some of those substances may or may not act as reactants when placed in spatial proximity to other substances in a chemical system at certain physical conditions (e.g. a certain temperature and a certain pressure). As broadly understood by those skilled in the art, reagents also include classes of materials that can serve as reaction-modifiers that are not consumed in reactions but can affect reactions between other substances; examples of such reaction-modifiers include inhibitors, blockers, promoters, transient binders, energy-providing molecules (e.g. adenosine triphosphate, ATP), enzymes, and catalysts.

It is commonly understood in the field of physics that electric field lines are directional lines that emanate from positive electric charges and terminate at negative electric charges. In the case of gel electrophoresis, when an electrical voltage (i.e. voltage) is applied across inert electrodes (e.g. platinum electrodes) that are immersed in an electrolyte solution, which is electrically conductive because of ionic content, in a commonly used configuration suitable for standard gel electrophoresis, an approximately uniform electric field is generated with electric field lines that are substantially parallel and unidirectional and represent approximately the same electric field strength everywhere in the gel.

In the field of electrophoresis, the term 'matrix' is employed in a broad manner to convey a porous solid material having continuously interconnected pore-regions that are filled with an electrolyte solution used to perform electrophoresis. The continuously interconnected pore-regions impart a permeability to molecules and/or colloidal objects, which are dissolved in and/or dispersed in the electrolyte solution, such that these molecules and/or colloidal objects can be propagated electrophoretically through the matrix when an electric field is applied, provided that these molecules and/or colloidal objects are sufficiently small compared to a characteristic pore size of the porous solid material. In order to enable electrophoretic propagation of molecules and/or colloidal objects, it is often useful for the characteristic pore size of a porous solid material to be at least one of nano-scale or micro-scale; so, the characteristic pore size is typically less than 100 microns to facilitate propagation of molecules and/or colloidal objects and also to facilitate molecular and/or colloidal sorting when performing electrophoresis. As an example, when performing gel electrophoresis, the matrix is often composed of a gel material, which is a type of porous solid material, that is filled with an electrolyte solution, often an aqueous buffer solution to set and maintain pH. In certain specific cases, gel electrophoresis is sometimes alternatively referred to as slab gel electrophoresis because the matrix is slab-like in overall form. For example, the overall shape of the matrix in slab gel electrophoresis is often a rectangular prismatic slab; this slab-like matrix is commonly decorated with wells that are surface features devoid of porous solid material in order to facilitate loading of molecules and/or colloidal objects into the matrix prior to applying the electric field. Common examples of gel materials that are porous solid materials used in the matrix in gel electrophoresis are polymer gels, such as agarose gels and crosslinked polyacrylamide gels. A characteristic pore size of a porous solid material is sometimes referred to as a mesh size of that porous solid material; the term 'mesh size' is often used when referring to porous polymer gel materials. Alternative types of porous solid materials, including but not limited to micro-porous silica and nano-porous silica, can have similar characteristic pore sizes and therefore molecular and colloidal sorting properties as polymer gels (also known as polymeric gels). Thus, as an example, a matrix made of an inorganic porous solid material, such as micro-porous silica or nano-porous silica (i.e. silicate glass), can effectively serve as a gel in performing molecular and/or colloidal sorting in what is still referred to as gel electrophoresis. Such sorting refers to spatial sorting resulting from performing electrophoresis, and this spatial sorting is alternatively sometimes called sieving by those skilled in the art of electrophoresis. Thus, it is understood by those skilled in the art that the meaning of 'gel' in 'gel electrophoresis' refers broadly to a wider range of porous solid materials, including but not limited to gels such as commonly-encountered polymer gels, that can function in a similar manner as a matrix when performing electrophoresis.

Different types of porous solid materials, which include electrophoretic gels, can have different distributions of pore sizes. A property of a given porous solid material having continuously interconnected pore regions, related to transport of objects through that porous solid material, is the characteristic pore size of that given porous solid material. It can be desirable in many applications, including gel electrophoresis, for a porous solid material to have a narrow pore-size distribution (i.e. when the standard deviation of the pore-size distribution is significantly smaller than the average of the pore-size distribution). In the case of assessing directional electrophoretic propagation of objects in an electrolyte solution through the continuously interconnected pores of that given porous medium (e.g. an electrophoretic gel), an object (e.g. a molecular object or a colloidal object) can only propagate in a sustained manner over significant periods of time if the minimum spatial dimension of that object is smaller than the characteristic pore size of that porous solid material. Physically, if the minimum spatial dimension of that object instead were bigger than the characteristic pore size of the porous solid material, then that object would rapidly become entrapped by the rigid structure of that porous solid material, since even its smallest spatial dimension is too small to fit through the pore openings. For instance, some types of charged polymeric molecular objects that are flexible (e.g. single-stranded DNA) have minimum spatial dimensions that are smaller than a characteristic pore size of an electrophoretic gel even as their maximum spatial dimension when fully stretched could be significantly greater than that characteristic pore size; such flexible polymeric molecular objects can still propagate while their electrophoretic mobilities can depend on their lengths which creates spatial sorting for which gel electrophoresis is commonly used. Examples of porous solid materials suitable for propagating reagents electrophoretically include but are not limited to: an electrophoretic gel, a polymeric gel, an agarose gel, a polyacrylamide gel, a porous silicate glass, a nanoporous solid, a microporous solid, and an open-pore solid foam.

In an embodiment of the current invention, a porous solid material in a matrix is electrically insulating. Application of the electric field, accomplished by applying a voltage from a power source across two electrodes (e.g. a positive electrode and a negative electrode) immersed in an electrolyte solution which is also in contact with the matrix loaded with reagents, produces an ionic electrical conduction in said matrix. Thus, the primary form of electrical conduction within said matrix is through the electrolyte solution and not through the porous solid material itself.

In an embodiment of the current invention, a porous solid material in a matrix is chemically inert with respect to reagents and therefore does not participate in chemical reactions resulting from an electrophoretic collision of reagents.

In an embodiment of the current invention, a matrix containing a porous solid material that is filled with an electrolyte solution (e.g. an electrophoretic gel filled with an aqueous buffer solution), placed in an electrophoretic chamber, loaded with at least a first reagent and a second reagent in separate wells along the same lane, is illuminated with electromagnetic radiation, such as photonic illumination, that includes but is not limited to the following characteristics: single-wavelength light, multi-wavelength light, gamma-ray-wavelength light, x-ray-wavelength light, extreme ultraviolet light, deep ultraviolet light, ultraviolet light, visible light, full spectrum visible light, infrared light, far infrared light, extreme far infrared light, microwave light (i.e. microwave radiation), radio-frequency radiation, intensity-controlled light, laser light, light-emitting-diode light, halogen light, optical-parametric-oscillator light, scanned-beam light, scanned-sheet light, wide-area light, polarized light, coherent light, incoherent light, directional light, focused light, collimated light, temporally intensity-modulated light, temporally polarization-modulated light, and spatially-uniform light. This illumination can be maintained throughout the entire electrophoresis experiment both before, during, and after the application of an electric field and also before, during, and after a band-collision of said first and second reagents occurs. In an alternative embodiment of the current invention, this illumination can be turned on and off over time as desired, in coordination with the timing of detecting optical signals coming from the interaction of this photonic illumination with reagents.

In an embodiment of the current invention, it is desirable to illuminate an electrophoretic gel that has been placed in an electrophoretic chamber and use an image detector to measure a pre-loading reference image of the gel prior to loading with a reagent. This pre-loading reference image can then be used in later analysis (e.g. through image subtraction or image division using this pre-loading reference image) of images taken subsequent to loading.

In an embodiment of the current invention, illuminating electromagnetic radiation interacts with at least one of a reagent, a reactant, and a reaction-product to yield an optical signal that is detected wherein said optical signal is at least one of: a photoluminescence, chemiluminescence, electroluminescence, radioluminescence, bioluminescence, scattered electromagnetic radiation, reflected electromagnetic radiation, unabsorbed electromagnetic radiation, transmitted electromagnetic radiation, polarized electromagnetic radiation, frequency-shifted electromagnetic radiation, sum-frequency electromagnetic radiation, gamma electromagnetic radiation, fluorescent electromagnetic radiation, and phosphorescent electromagnetic radiation.

In an embodiment of the current invention, the optical signal resulting from the interaction of illuminating electromagnetic radiation with at least one of a reagent, a reactant, and a reaction-product is detected using a detector that is one of: an image sensor, a digital array detector, a digital camera, a color digital video camera, a charge-coupled device (CCD) detector, a CMOS detector, a photodiode array detector, an avalanche photodiode detector, an avalanche photodiode array detector, an intensified digital camera, a low-noise actively-cooled digital camera, a digital array detector sensitive to infrared light, a digital array detector sensitive to ultraviolet light, a digital array detector sensitive to visible light, a spectrometer, an ultraviolet-visible spectrometer, a Fourier transform infrared spectrometer, a Raman spectrometer, a spectrophotometer, an imaging spectrometer, a multispectral camera, a hyperspectral camera, a phosphor-optical digital array detector, and a fiber optic spectrometer.

In an embodiment of the current invention, the detection of the optical signal is accomplished using an image-array detector that conveys spatially-encoded spectroscopic information of the optical signal. Examples of such image-array detectors that provide spatially-encoded spectroscopic information include but are not limited to: RGB (red-green-blue) color CCD image detectors, RGB color CMOS image detectors, CMYK color image detectors, color digital cameras, color digital video cameras, infrared image detectors, ultraviolet image detectors, photodiode array detectors, avalanche photodiode array detectors, and an imaging spectrometer. In an embodiment of the current invention at least one of a band-collision of reagents and a reaction-product is detected using an imaging spectrometer to measure the optical signal and provide spatially encoded spectra.

In an embodiment of the current invention, the detector used to detect the optical signal emanating from the illuminated matrix region, which contains at least one of a first reagent, a second reagent, and a reaction-product, is a hyperspectral camera that measures a wavelength-dependent spectrum at each pixel in its two-dimensional array detector. A hyperspectral camera provides much more direct and useful optical spectral information that can be used to detect the presence of and spatial distribution of the concentration of a wide range of chemical species as compared to a common red-green-blue (RGB) color digital camera. It is commonly known by those skilled in the art that extracting full, continuous optical spectra over a wide range of wavelengths cannot be generally achieved using the limited information contained in an RGB signal in a given pixel. So, a hyperspectral camera offers the desirable capability of measuring the temporal evolution of complex spatial distributions of optical spectroscopic fingerprints of illuminated molecular and/or colloidal objects in gels, which are captured in sequences of hyperspectral images, sometimes referred to as datacubes (i.e. light intensity as a function of a first spatial direction, a second spatial direction orthogonal to the first, and wavelength). Thus, by using a hyperspectral camera equipped with a suitable lens as a detector, one can obtain real-time, time-dependent, spatially-resolved, optical-spectroscopic measurements that are useful in identifying electrophoretic band-collisions of reagent species and the formation and evolution of any reaction-products that may be produced as a consequence of such band-collisions in the matrix. As an example, one commercially available hyperspectral camera is a continuous visible-to-near-infrared (VIS/NIR) Hyperspectral Pushbroom Imager, having a wavelength range from 500 nm to 1000 nm, made by Diaspective Vision. This Hyperspectral Pushbroom Imager utilizes a CMOS-based hyperspectral camera with 2048× 1088 pixels at up to 12 bit-depth and employs a holographic grating. In an embodiment of the current invention, a hyperspectral camera is used as a detector, thereby providing real-time, spatially-resolved, temporally-resolved, optical-spectroscopic measurements while performing BCGE. This detector is connected to a computer which stores, records, and analyzes these measurements to calculate and provide information about at least one of reagent band-propagation, reagent band-collisions, existence of reactions, extent of reactions, existence of reaction-products, types of reaction-products, rates of formation of reaction-products, concentrations of reaction products. This use of a hyperspectral camera as a detector is particularly advantageous when employed for BCGE involving different combinations of reagents in a plurality of lanes having two or more wells in each lane, thereby providing a high-throughput methodology for examining multiple reactions and programmed sequences of reactions.

In an embodiment of the present invention, the optical detector used to detect the optical signal emanating from the illuminated matrix region, which contains at least one of a first reagent, a second reagent, and a reaction-product, is a multi-spectral camera. Multi-spectral cameras offer better access to spatially-resolved spectral information than ordinary RGB color digital cameras; yet, multi-spectral cameras typically provide less finely resolved spectral information than hyperspectral cameras.

In an embodiment of the current invention, at least one of a portion of a first reagent and at least a portion of a second reagent is at least one of: ions, acids, bases, dye molecules, chelating agents, oxidizing agents, reducing agents, catalytic agents, initiators, reactive monomers, charge-neutral biomacromolecules, charged biomacromolecules, biomacromolecular assemblies, charge-neutral colloidal particles, charged colloidal particles, charge-neutral colloidal droplets, charged colloidal droplets, quantum dots, carbon nanotubes, biological cells, biological cell lysates, viruses, viral proteins, viral lysates, yeast, yeast lysates, bacteria, bacterial lysates, ribosomes, nucleosomes, vesicles, micelles, oligomers, polymers, nucleic acids, poly-nucleic acids, poly-deoxyribonucleic acids (DNA), ribonucleic acids (RNA), messenger ribonucleic acids (mRNA), transfer ribonucleic acids (tRNA), primers, ribonucleoproteins, small nuclear ribonucleoproteins (snRNP), RNA polymerases, reverse transcriptases, proteins, carbohydrates, lipids, surfactants, enzymes, sugars, phosphates, amino acids, peptides, and poly-peptides.

In an embodiment of the current invention, the type of reaction that occurs as a consequence of an electrophoretic collision of at least a portion of a first reagent and at least a portion of a second reagent is at least one of: an oxidation-reduction reaction, a complexation reaction, a chelating reaction, a charge-neutralization reaction, a proton-exchange reaction, a protonation reaction, a hydroxylation reaction, a cleavage reaction, an acid-base reaction, an exchange reaction, a ligand-exchange reaction, an ion-exchange reaction, a polymerization reaction, a catalytic reaction, a decomposition reaction, a replacement reaction, a phase-change reaction, a gas-generating reaction, an exothermic reaction, an endothermic reaction, a precipitation reaction, a coalescence reaction, an enzymatic reaction, a binding reaction, an adsorption reaction, a click reaction, a substitution reaction, a biochemical reaction, a denaturation reaction, a crystallization reaction, an aggregation reaction, a splicing reaction, a transesterification reaction, a transcription reaction, an addition reaction, a condensation reaction, a self-assembly reaction, a functionalization reaction, a chain reaction, a polymerase chain reaction, a gene-expression reaction, and a biomineralization reaction.

In an embodiment of the current invention, a plurality of reaction-products is generated when at least a portion of a first reagent collides with at least a portion of a second reagent after applying the electric field to the reagent-loaded matrix of electrophoretic gel filled with an aqueous buffer solution. Continuing application of the electric field subsequent to this collision is then used to spatially sort this plurality of reaction-products according to their respective electrophoretic mobilities in the electrophoretic gel filled with an aqueous buffer solution. After this plurality of reaction-products is spatially sorted, as measured by detected optical signals resulting from illumination of the matrix and materials within, then the electric field is removed and common methods of isolation and extraction for recovering species from electrophoretic gels are used to select and recover only certain reaction-products from the plurality of reaction-products produced. Such common methods of isolation and extraction include but are not limited to: elution and physically cutting out a section of the gel containing the desired optically-detected reaction-product.

In an embodiment of the current invention, a gradient electrophoretic gel is used instead of a uniform homogeneous electrophoretic gel in producing electrophoretic collisions of bands of at least a portion of a first reagent and at least a portion of a second reagent subsequent to applying an electric field to cause electrophoretic propagation and collision. In a gradient electrophoretic gel, each reagent-species can have a spatially-dependent electrophoretic mobility, rather than a single electrophoretic mobility. To those skilled in the art, use of a gradient electrophoretic gel, which can cause a spatially dependent electrophoretic mobility of some species undergoing electrophoretic transport, rather than a homogeneous uniform gel, is readily anticipated.

In an embodiment of the current invention, the applied electric field varies in time. This temporal variation in the applied electric field can be achieved by at least one of varying the voltage supplied by the power supply to the electrodes and varying the location and position of the electrodes relative to the matrix.

In an alternative embodiment of the current invention, the electric field is removed when two bands of different reagents collide, as detected by a detector sensing an image detected resulting from the interaction of illuminating light with said reagents. After a period of time when the electric field is off and the reagents have had additional time to react, the electric field is re-applied in order to cause separation of reaction-products by the gel.

In an embodiment of the current invention, a plurality of reaction-products resulting from electrophoretically colliding reagents are spatially sorted in the matrix through electrophoretic propagation of these reaction-products subsequent to a collision of reagents containing reactants. This spatial sorting is achieved simply by maintaining the applied electric field over a period of time subsequent to said collision of reagents. In an alternative embodiment of the current invention, this spatial sorting of said plurality of reaction-products is detected optically, and the electric field is removed when a degree of spatial sorting is sufficient to allow isolation and extraction of particular product-species in one or more particular spatial locations, as measured through this optical detection.

In an embodiment of the current invention, a reaction-product, formed from a reaction resulting from an electrophoretic collision of a first band of a first reagent with a second band of a second reagent in an electrophoretic gel, is removed from said electrophoretic gel by at least one of isolation, extraction, elution, cutting a limited spatial region out of the gel and separating from the rest of the gel, and suctioning. In a further embodiment of the current invention, a spatial region of a desired reaction-product at a spatial location is identified by an image sensing device (e.g. color digital camera) that measures an optical signal from the illuminated reaction-product in order to facilitate removal of said desired reaction-product.

In an alternative embodiment of the current invention, a reaction-modifier is added to the electrolyte solution and is present at sufficient concentration in the electrolyte solution throughout the matrix in order to influence a reaction caused by an electrophoretic collision of reagents. Such reaction-modifiers include but are not limited to: a catalyst species, an enzymatic species, a ligand species, a chelating species, an energy-providing molecular species, a promoter species, and an inhibitor species. Ways in which reaction-modifiers influence reactions include but are not limited to: modifying a rate of a reaction and modifying a yield of a reaction-product.

In an embodiment of the current invention, a passivation agent is used to passivate a matrix and thereby facilitate electrophoretic propagation of at least one of molecules and colloidal objects by reducing attractive interactions between said at least one of molecules and colloidal objects with the porous solid material. Treating a matrix with a passivation agent produces a passivated matrix. For example, when casting an agarose gel in an aqueous buffer solution, a passivation agent can be added to the buffer solution prior to the solidification of this agarose gel to produce a passivated gel. Alternatively, an existing matrix can be soaked in an electrolyte solution containing a passivation agent for a period of time sufficient for the passivation agent to treat the pore-surfaces of the porous solid material in order to produce a passivated matrix. Examples of passivation agents include but are not limited to: surfactants, lipids, polymers, proteins, and block-copolymers. As a further example, passivation agents that have been used to passivate agarose gels and thereby facilitate electrophoretic propagation of anionically charged nanoparticles include but are not limited to: sodium dodecyl sulfate (SDS) and poly-ethylene glycol (PEG, typical molecular weight less than 10,000 g mol$^{-1}$).

In an embodiment of the current invention, a first electrolyte solution used to cast an electrophoretic gel is different from a second electrolyte solution that is used to fill an electrophoretic chamber and into which an electrophoretic gel is placed in contact. For certain electrophoretic chambers, said second electrolyte solution has a volume that is significantly larger than said first electrolyte solution, and so the resulting combined electrolyte solution dominantly has properties (e.g. pH) that are approximately the same as those of the second electrolyte solution. In addition, molecular and colloidal objects, such as reaction-modifiers, which have been added to said second electrolyte solution, are loaded uniformly into said electrophoretic gel by soaking said electrophoretic gel in said second electrolyte solution for a period of time sufficient for diffusive transport to cause such molecular and colloidal objects to be present in the continuously interconnected pore regions of said electrophoretic gel.

In an embodiment of the current invention, a well decorating a slab matrix is in the shape of a rectangular prism. This slab matrix has two parallel faces, and the minimum spatial dimension of the matrix lies along a line that is orthogonal to both of these faces, which defines the thickness of the slab matrix. The spatial depth dimension of this rectangular prismatic well starts at one face and lies along a direction perpendicular to a face of the slab, going into the slab. Because this direction associated with depth dimension is perpendicular to the applied electric field when performing slab gel electrophoresis, this depth dimension is largely inconsequential in aspects of electrophoretic propagation. Thus, to those skilled in practicing slab gel electrophoresis, when referring to a minimum spatial dimension of a well, this depth is neglected, since the intended meaning is the minimum spatial dimension of the two dimensions of a well's rectangular cross section in a plane parallel with a face of the slab matrix.

In an embodiment of the current invention, an electrophoresis chamber is at least one of a horizontal gel electrophoresis chamber and a vertical gel electrophoresis chamber. The orientation of the electrophoresis chamber holding the gel, whether horizontal or vertical, is inconsequential regarding the electrophoretic propagation and collision of reagents.

In an embodiment of the current invention, an electrophoresis chamber is transparent to illuminating electromagnetic radiation and is also transparent to light emanating from the matrix that results from the interaction of said illuminating electromagnetic radiation with at least one of a reagent and a reaction-product in said matrix.

In an embodiment of the current invention, a temperature regulator is placed in good thermal contact with an electrophoretic chamber, in which electrophoretically colliding reagents is performed, thereby controlling and regulating the temperature at which at least one of electrophoretic propagation of reagents, electrophoretic collision of reagents, electrophoretic reaction of reagents, and electrophoretic propagation of reaction-products occurs.

In an alternative embodiment of the current invention, a temperature regulator is used to control a temperature of a reaction produced through electrophoretic collision of reagents in a matrix loaded into an electrophoretic chamber in good contact with said temperature regulator.

In an alternative embodiment of the current invention, a temperature regulator is cycled upwards and downwards in temperature to achieve a polymerase chain reaction of at least one of a reagent and a reaction-product species in said matrix at a time that is subsequent to loading reagents into said matrix. The porous solid material in said matrix is selected to remain stable at temperatures over the range from the minimum temperature to the maximum temperature of the temperature cycle. A waveform associated with the cycling of the temperature regulator is controlled by a computer. Common example waveforms include but are not limited to: sawtooth waveform, sinusoidal waveform. and square waveform.

In an embodiment of the current invention, a temperature regulator that is placed in good thermal contact with at least one of the electrophoretic chamber and the electrolyte solution in contact with the matrix is at least one of a thermoelectric heat pump (i.e. Peltier device), a heat exchanger connected to a recirculating actively temperature-controlled bath, and a temperature-controlled environmental chamber that encloses the electrophoretic chamber.

In an embodiment of the current invention, an illumination source is arranged proximate to an electrophoresis chamber and to a detector in a manner to provide directional illuminating electromagnetic radiation that is at least one of: transmission-illumination, side-illumination, and reflection-illumination. For said transmission-illumination, the direction of illuminating electromagnetic radiation is from the illumination source towards the matrix and also towards the detector. For said side-illumination, the direction of illuminating electromagnetic radiation is from the illumination source towards the matrix yet approximately perpendicular to a line between the center of the matrix and the center of the detector. For said reflection-illumination, the direction of illuminating electromagnetic radiation is from the illumination source towards the matrix, yet the detector is arranged to detect light emanating from the matrix back along a direction that is approximately opposite to the direction of illuminating electromagnetic radiation.

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A method of electrophoretically colliding reagents, comprising:
   providing a matrix that is a porous solid material having continuously interconnected pore regions that are filled with an electrolyte solution, said matrix and said electrolyte being suitable for performing electrophoresis;
   loading a first reagent in a first reagent-loading-region centered at a first spatial location in said matrix;
   loading a second reagent in a second reagent-loading-region centered at a second spatial location that is displaced from said first spatial location by a first displacement-distance in said matrix; and
   applying an electric field to said matrix loaded with said first reagent and said second reagent,
   wherein said applying said electric field causes electrophoretic propagation in said electrolyte solution through said continuously interconnected pore regions of at least a portion of said first reagent and electrophoretic propagation in said electrolyte solution through said continuously interconnected pore regions of at least a portion of said second reagent,
   wherein said electric field is applied for a first period of time sufficiently long that at least a portion of said first reagent collides with at least a portion of said second reagent to yield a first collision in a first collision-region centered at a first collision-location within said matrix as a consequence of said electrophoretic propagation, wherein a first electric field line of said electric field passes through said first reagent-loading-region and said second reagent-loading-region, wherein said first displacement-distance is sufficiently large that said first reagent-loading-region is separate from said second reagent-loading-region, wherein a first electrophoretic mobility of said at least a portion of said first reagent in said matrix of said porous solid material filled with said electrolyte solution is different from a second electrophoretic mobility of said at least a portion of said second reagent in said matrix of said porous solid material filled with said electrolyte solution, wherein said applying an electric field applies an electric field strength that is uniform and unidirectional in said matrix, wherein said first electric field line passes through said first spatial location and said second spatial location, wherein said applying said electric field is subsequent to said loading said matrix with said first reagent and said loading said matrix with said second reagent, wherein said applying said electric field causes an ionic electrical current in said electrolyte solution, wherein said electric field strength is sufficiently strong to cause said first collision in said first period of time, wherein said porous solid material comprises at least one of an electrophoretic gel, a polymeric gel, a crosslinked polymeric gel, an agarose gel, a polyacrylamide gel, a porous silicate glass, a nanoporous solid, a microporous solid, and an open-pore solid foam, wherein a characteristic pore size of said porous solid material is less than about 100 microns, wherein said electrolyte solution comprises an aqueous buffer solution having a prespecified buffer concentration and a prespecified buffer pH, wherein said matrix is shaped in the form of a three-dimensional prismatic slab having a slab thickness, wherein said matrix has a first well devoid of said porous solid material centered at said first spatial location, wherein said matrix has a second well devoid of said porous solid material centered at said second spatial location, wherein said first reagent-loading-region is limited by said first well, wherein said second reagent-loading-region is limited by said second well, wherein a maximum spatial dimension of said first well is less than a maximum spatial dimension of said three-dimensional prismatic slab, wherein a maximum spatial dimension of said second well is less than a maximum spatial dimension of said three-dimensional prismatic slab, wherein said loading said first well comprises fluidically injecting a first fluid containing said first reagent at a first reagent-concentration into said aqueous buffer solution in said first well, wherein said loading said second well comprises fluidically injecting a second fluid containing said second reagent at a second reagent-concentration into said aqueous buffer solution in said second well, and wherein said first and second fluids are miscible with water;

further comprising providing an electrophoretic chamber of a solid chamber-material suitable for receiving said matrix and suitable for filling with said electrolyte solution;

filling said electrophoretic chamber with said electrolyte solution;

immersing said matrix in said electrolyte solution within said electrophoretic chamber, wherein said solid chamber-material is electrically insulating, is impermeable to said electrolyte solution, and is non-reactive chemically with said electrolyte solution, said first reagent, and said second reagent, wherein said applying said electric field comprises applying a voltage between a first electrode in contact with said electrolyte solution and a second electrode in contact with said electrolyte solution inside said electrophoretic chamber, thereby causing an ionic electrical current to flow through said electrolyte solution within said matrix loaded with said first reagent and said second reagent, wherein said first electric field line lies along a straight line between said first spatial location and said second spatial location, wherein said first well in said three-dimensional prismatic slab in said matrix has a first well-shape that is a first rectangular prism, wherein said second well in said three-dimensional prismatic slab in said matrix has a second well-shape that is a second rectangular prism, wherein said fluidically injecting said first fluid containing said first reagent into said first well yields a first band of said first reagent, wherein said fluidically injecting said second fluid containing said second reagent into said second well yields a second band of said second reagent, wherein said first reagent has a first concentration inside said first band that is higher than outside said first well subsequent to said loading and prior to said applying said electric field, wherein said second reagent has a second concentration inside said second band that is higher than outside said second well subsequent to said loading and prior to said applying said electric field, wherein said first well-shape has a smallest spatial dimension along said first electric field line at said first spatial location, wherein said second well-shape has a smallest spatial dimension along said first electric field line at said second spatial location, wherein said applying said electric field causes electrophoretic propagation of at least one of at least a portion of said first band of said at least a portion of said first reagent and at least a portion of said second band of said at least a portion of said second reagent, wherein said electrophoretically colliding reagents comprises an electrophoretic band-collision of at least a portion of said first reagent and at least a portion of said second reagent at said first collision-location in said matrix immersed in said aqueous buffer solution, wherein a first reaction-product is produced by a first reaction that consumes at least a portion of a first reactant from among said portion of said first reagent and at least a portion of a second reactant from among said portion of said second reagent, wherein said first reaction occurs within said continuously interconnected pore regions filled with said electrolyte solution at said first collision-location within said matrix, wherein said first reaction-product is different from either of said first reactant and said second reactant, wherein said first reaction resulting from said electrophoretic band-collision yields a first reaction-product-band containing said first reaction-product at said first collision-location;

further comprising illuminating at least one of said first reagent, said second reagent, and said first reaction-product in said matrix with electromagnetic radiation; and detecting at least one of photoluminescence, chemiluminescence, electroluminescence, radioluminescence, bioluminescence, scattered electromagnetic radiation, reflected electromagnetic radiation, unabsorbed electromagnetic radiation, transmitted electromagnetic radiation, polarized electromagnetic radiation, frequency-shifted electromagnetic radiation, sum-frequency electromagnetic radiation, gamma electromagnetic radiation, fluorescent electromagnetic radiation, and phosphorescent electromagnetic radiation as a consequence of an interaction of said electromagnetic radiation with at least one of said first reagent, said second reagent, and said first reaction-product, wherein said illuminating with said electromagnetic radiation comprises photonic illumination that is at least one of single-wavelength light, multi-wavelength light, gamma-ray-wavelength light, x-ray-wavelength light, extreme ultraviolet light, deep ultraviolet light, ultraviolet light, visible light, full spectrum visible light, infrared light, far infrared light, extreme far infrared light, microwave light, intensity-controlled light, laser light, light-emitting-diode light, halogen light, optical-parametric-oscillator light, scanned-beam light, scanned-sheet light, wide-area light, polarized light, coherent light, incoherent light, directional light, focused light, collimated light, temporally intensity-modulated light, temporally polarization-modulated light, and spatially-uniform light, wherein said detecting is accomplished using a detector that is at least one of an image sensor, a digital array detector, a digital camera, a color digital video camera, a charge-coupled device (CCD) detector, a CMOS detector, a photodiode array detector, an avalanche photodiode detector, an avalanche photodiode array detector, a low-noise actively-cooled digital camera, a digital array detector sensitive to infrared light, a digital array detector sensitive to ultraviolet light, a digital array detector sensitive to visible light, a spectrometer, an ultraviolet-visible spectrometer, a Fourier transform infrared spectrometer, a Raman spectrometer, a spectrophotometer, an imaging spectrometer, a multi-spectral camera, a hyperspectral camera, a phosphor-optical digital array detector, and a fiber optic spectrometer; and further comprising constructing a space-time plot of said electrophoretic band-collision, wherein a first spatial axis of said space-time plot encodes distance along said electric field in said matrix, and a second spatial axis of said space-time plot encodes time elapsed subsequent to said applying said electric field, and wherein at least one of an intensity, a color, and a frequency from said detector is recorded on said space-time plot as a function of said first spatial axis and said second spatial axis.

2. The method according to claim 1, wherein said first reagent comprises a plurality of a first reagent-species, wherein said second reagent comprises a plurality of a second reagent-species, wherein said first reagent-species is different from said second reagent-species, wherein at least one of said first reagent-species and said second reagent-species has a minimum spatial dimension that is less than a characteristic pore size of said porous solid material, wherein said first reagent-species has said first electrophoretic mobility, wherein said second reagent-species has said second electrophoretic mobility, and wherein at least one of said first electrophoretic mobility and said second electrophoretic mobility is non-zero.

3. The method according to claim 1, wherein said electrophoretic propagation of said at least a portion of said first reagent and at least a portion of said second reagent is at least one of counter-propagating, uni-propagating, and co-propagating.

4. The method according to claim 1, wherein a first reaction-product is produced by a first reaction that consumes at least a portion of a first reactant from among said portion of said first reagent and at least a portion of a second reactant from among said portion of said second reagent;

wherein said first reaction occurs within said continuously interconnected pore regions filled with said electrolyte solution at said first collision-location within said matrix; and wherein said first reaction-product is different from either of said first reactant and said second reactant.

5. The method according to claim 4, further comprising loading said matrix with a third reagent in a third reagent-loading-region centered at a third spatial location;

wherein said third spatial location is along said first electric field line through said first and second spatial locations, wherein at least a portion of said third reagent collides with at least one of a portion of said first reagent, a portion of said second reagent, and a portion of said first reaction-product to yield a second collision in a second collision-region centered at a second collision-location, and wherein a second reaction-product is produced by a second reaction as a consequence of said second collision in said second collision-region.

6. The method according to claim 5, further comprising loading said matrix with a fourth reagent in a fourth reagent-loading-region centered at a fourth spatial location; and loading said matrix with a fifth reagent in a fifth reagent-loading-region centered at a fifth spatial location that is displaced from said fourth spatial location by a second displacement-distance;

wherein said applying said electric field causes electrophoretic propagation in said electrolyte solution through said continuously interconnected pore regions of at least one of a portion of said fourth reagent and a portion of said fifth reagent;

wherein said electric field is applied for a first period of time sufficiently long that at least a portion of said fourth reagent collides with at least a portion of said fifth reagent to yield a third collision in a third collision-region centered at a third collision-location within said matrix as a consequence of said electrophoretic propagation;

wherein a second electric field line of said electric field passes through said fourth reagent-loading-region and said fifth reagent-loading-region;

wherein said second displacement-distance is sufficiently large that said fourth reagent-loading-region is separate from said fifth reagent-loading-region;
wherein said first and said second electric field lines do not intersect; and
wherein a fourth electrophoretic mobility of said at least a portion of said fourth reagent in said matrix of said porous solid material filled with said electrolyte solution is different from a fifth electrophoretic mobility of said at least a portion of said fifth reagent in said matrix of said porous solid material filled with said electrolyte solution.

7. The method according to claim 6, wherein a third reaction-product is produced by a third reaction that consumes at least a portion of a fourth reactant from among said portion of said fourth reagent and at least a portion of a fifth reactant from among said portion of said fifth reagent;
wherein said third reaction occurs within said continuously interconnected pore regions filled with said electrolyte solution at said third collision-location within said matrix; and
wherein said third reaction-product is different from either of said fourth reactant and said fifth reactant.

8. The method according to claim 5, wherein a desired sequence of reaction is obtained by pre-designing said first reagent-loading-region centered at said first spatial location, said second reagent-loading-region centered at said second spatial location, and said third reagent-loading-region centered at said third spatial location to cause said first reaction-product to form and subsequently said first reaction-product and said third reagent to collide in said matrix.

9. The method according to claim 4, wherein said electric field causes said first reaction-product to propagate electrophoretically subsequent to said first reaction;
wherein said first reaction-product has a first reaction-product electrophoretic-mobility that is different from either of said first electrophoretic mobility and said second electrophoretic mobility; and
wherein said first reaction-product is spatially separated electrophoretically in said matrix as a consequence of said electric field subsequent to said colliding.

10. The method according to claim 4, further comprising providing a reaction-modifier species;
adding said reaction-modifier species to said electrolyte solution;
wherein said reaction-modifier species comprises at least one of a catalyst species, an enzymatic species, a ligand species, a chelating species, an energy-providing molecular species, a promoter species, and an inhibitor species;
wherein said reaction-modifier species is added at sufficient concentration to modify at least one of a rate of reaction of said first reaction and a yield of said first reaction-product of said first reaction.

11. The method according to claim 1, further comprising isolating and extracting said first reaction-product from said matrix subsequent to said first reaction.

12. The method according to claim 1, wherein the existence of said first reaction-product is detected by said detector.

13. The method according to claim 1, further comprising passivating said matrix with a passivation agent that facilitates electrophoretic propagation of at least one of said portion of said first reagent and said portion of said second reagent.

14. The method according to claim 1, further comprising creating a set of color-separated space-time plots from said space-time plot, wherein a first color-separated space-time plot of said set is created by selecting only a first color of a first reagent, a second color-separated space-time plot of said set is created by selecting only a second color of a second reagent, and a third color-separated space-time plot of said set is created by selecting only a third color of said first reaction-product.

15. The method according to claim 1, further comprising using recorded features on said space-time plot to determine at least one of a lifetime and an electrophoretic mobility of said first reaction-product resulting from said electrophoretic band-collision.

16. The method according to claim 15, further comprising determining a lifetime of said first reaction-product by fitting a time-dependent intensity profile of said first reaction-product using at least one of a Fermi-like function and a log-normal function.

17. An electrophoretic spectroscopic imaging device for real-time spatially-resolved spectroscopic imaging of reagents and reaction-products resulting from electrophoretic collisions of reagents, comprising:
an electrophoresis component comprising an electrophoretic chamber suitable to receive a matrix of a porous solid material filled with an electrolyte solution in which a first reagent and a second reagent are loaded in localized regions during operation that are spatially separate;
a pair of electrodes arranged to be proximate opposing ends of said matrix such that said matrix is arranged with at least a portion between said pair of electrodes and said pair of electrodes are structured to be electrically connected to a power supply such that at least a portion of said first and second reagents electrophoretically propagate as an ionic current that flows between said pair of electrodes and to collide as a consequence of applying an electric field between said pair of electrodes;
an illumination source arranged to illuminate said matrix loaded with said first and second reagents with electromagnetic radiation such that interaction of said electromagnetic radiation with at least a portion of said first and second reagents yields at least one of absorbed, transmitted, scattered, fluoresced, phosphoresced, and emitted light as a function of spatial position in said matrix;
a spectroscopic-imaging device configured to obtain at least one of image data and spectroscopic data from said at least one of absorbed, transmitted, scattered, fluoresced, phosphoresced, and emitted light at imaging times prior to, during, and subsequent to said electrophoretic collision; and
a computing device configured to receive and process said at least one of image data and spectroscopic data to provide information concerning at least one of a spatial location of said electrophoretic collision of said at least a portion of said first and second reagents, a change in concentration of at least a portion of said first and second reagents, a detection of the existence of a reaction-product resulting from said electrophoretic collision, a measurement of the concentration of a reaction-product resulting from said electrophoretic collision, a yield of a reaction-product resulting from said electrophoretic collision, an electrophoretic mobility of a reaction-product resulting from said electrophoretic collision, a rate constant associated with a reaction-product resulting from said electrophoretic collision, and a temporal stability of a reaction-product resulting from said electrophoretic collision, wherein said applying an electric field comprises applying a voltage across a first electrode immersed in said electrolyte solution and a second electrode immersed in said electrolyte solution thereby generating an ionic current that flows between said first electrode and said second electrode, and wherein said computing device is further configured to measure a space-time plot from said at least one of image data and spectroscopic data, wherein said computing device is further configured to construct said space-time plot of an electrophoretic band-collision, wherein a first spatial axis of said space-time plot encodes distance along said electric field in said matrix, and a second spatial axis of said space-time plot encodes time elapsed subsequent to said applying said electric field, and wherein at least one of an intensity, a color, and a frequency detected is recorded on said space-time plot as a function of said first spatial axis and said second spatial axis.

18. A device according to claim 17, further comprising:
a temperature regulator configured to control a temperature of said electrophoretic chamber, said matrix, said electrolyte solution, and said first and second reagents;
wherein said electric field is uniform in said matrix,
wherein said matrix of a porous solid material filled with an electrolyte solution is an electrophoretic gel filled with an aqueous buffer solution having a prespecified type, prespecified pH, and prespecified concentration,
wherein said electrophoretic gel defines a plurality of electrophoretic wells into which said first and second reagents are fluidically injected,
wherein said electrophoretic wells containing said first and second reagents lie along an electric field line of said electric field,
wherein said electrophoretic wells each have the shape of a rectangular prism,
wherein said electrophoretic propagation of said at least a portion of said first and second reagents is at least one of counter-propagating, uni-propagating, and co-propagating, and
wherein said reaction-product has at least one of a different spectroscopic property, a different fluorescence property, and a different propagation rate than either of said at least a portion of said first and second reagents.

19. A method of electrophoretically colliding reagents, comprising:
providing a matrix that is a porous solid material having continuously interconnected pore regions that are filled with an electrolyte solution, said matrix and said electrolyte being suitable for performing electrophoresis;
loading a first reagent in a first reagent-loading-region centered at a first spatial location in said matrix;
loading a second reagent in a second reagent-loading-region centered at a second spatial location that is displaced from said first spatial location by a first displacement-distance in said matrix; and
applying an electric field to said matrix loaded with said first reagent and said second reagent,
wherein said applying said electric field causes electrophoretic propagation in said electrolyte solution through said continuously interconnected pore regions of at least a portion of said first reagent and electrophoretic propagation in said electrolyte solution through said continuously interconnected pore regions of at least a portion of said second reagent,
wherein said electric field is applied for a first period of time sufficiently long that at least a portion of said first reagent collides with at least a portion of said second reagent to yield a first collision in a first collision-region centered at a first collision-location within said matrix as a consequence of said electrophoretic propagation,
wherein a first electric field line of said electric field passes through said first reagent-loading-region and said second reagent-loading-region,
wherein said first displacement-distance is sufficiently large that said first reagent-loading-region is separate from said second reagent-loading-region,
wherein a first electrophoretic mobility of said at least a portion of said first reagent in said matrix of said porous solid material filled with said electrolyte solution is different from a second electrophoretic mobility of said at least a portion of said second reagent in said matrix of said porous solid material filled with said electrolyte solution,
wherein said loading said first reagent in said first reagent-loading-region yields a first band of said first reagent,
wherein said loading said second reagent in said second reagent-loading-region yields a second band of said second reagent,
wherein said applying said electric field causes electrophoretic propagation of at least a portion of said first band or at least a portion of said second band to provide an electrophoretic band-collision,
the method further comprising constructing a space-time plot of said electrophoretic band-collision,
wherein a first spatial axis of said space-time plot encodes distance along said electric field in said matrix, and a second spatial axis of said space-time plot encodes time elapsed subsequent to said applying said electric field, and
wherein at least one of an intensity, a color, and a frequency detected is recorded on said space-time plot as a function of said first spatial axis and said second spatial axis.

20. The method according to claim 19, further comprising creating a set of color-separated space-time plots from said space-time plot, wherein a first color-separated space-time plot of said set is created by selecting only a first color of a first reagent, a second color-separated space-time plot of said set is created by selecting only a second color of a second reagent, and a third color-separated space-time plot of said set is created by selecting only a third color of a first reaction-product.

21. The method according to claim 19, further comprising using recorded features on said space-time plot to determine at least one of a lifetime and an electrophoretic mobility of a first reaction-product resulting from said electrophoretic band-collision.

22. The method according to claim 21, further comprising determining a lifetime of said first reaction-product by fitting a time-dependent intensity profile of said first reaction-product using at least one of a Fermi-like function and a log-normal function.

* * * * *